(12) United States Patent
Liu et al.

(10) Patent No.: US 11,873,292 B2
(45) Date of Patent: Jan. 16, 2024

(54) TRANS-INDOLINE CYCLOPROPYLAMINE CHEMICAL COMPOUND, AND METHOD FOR PREPARATION, PHARMACEUTICAL COMPOSITION, AND USE THEREOF

(71) Applicant: Shanghai Institute of Materia Medica, Chinese Academy of Sciences, Shanghai (CN)

(72) Inventors: Hong Liu, Shanghai (CN); Jia Li, Shanghai (CN); Wei Zhu, Shanghai (CN); Yubo Zhou, Shanghai (CN); Jiang Wang, Shanghai (CN); Mingbo Su, Shanghai (CN); Shuni Wang, Shanghai (CN); Wei Xu, Shanghai (CN); Chunpu Li, Shanghai (CN); Weijuan Kan, Shanghai (CN); Hualiang Jiang, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 264 days.

(21) Appl. No.: 16/306,751

(22) PCT Filed: Jun. 2, 2017

(86) PCT No.: PCT/CN2017/087081
§ 371 (c)(1),
(2) Date: Mar. 29, 2019

(87) PCT Pub. No.: WO2017/215464
PCT Pub. Date: Dec. 21, 2017

(65) Prior Publication Data
US 2019/0210998 A1     Jul. 11, 2019

(30) Foreign Application Priority Data
Jun. 3, 2016 (CN) .......................... 201610390628.6

(51) Int. Cl.
| | |
|---|---|
| *C07D 403/12* | (2006.01) |
| *C07D 215/58* | (2006.01) |
| *C07D 209/04* | (2006.01) |
| *C07D 215/00* | (2006.01) |
| *C07D 487/04* | (2006.01) |
| *C07D 209/08* | (2006.01) |
| *C07D 401/12* | (2006.01) |
| *C07D 405/12* | (2006.01) |
| *A61P 35/00* | (2006.01) |

(52) U.S. Cl.
CPC .......... *C07D 403/12* (2013.01); *A61P 35/00* (2018.01); *C07D 209/04* (2013.01); *C07D 209/08* (2013.01); *C07D 215/00* (2013.01); *C07D 215/58* (2013.01); *C07D 401/12* (2013.01); *C07D 405/12* (2013.01); *C07D 487/04* (2013.01); *Y02P 20/55* (2015.11)

(58) Field of Classification Search
CPC .. C07D 403/12; C07D 209/04; C07D 209/08; C07D 215/00; C07D 215/58; C07D 401/12; C07D 405/12; C07D 487/04; A61P 35/00; Y02P 20/55
See application file for complete search history.

(56) References Cited

FOREIGN PATENT DOCUMENTS

| CN | 105283177 A | 1/2016 |
|---|---|---|
| CN | 106045862 A | 10/2016 |
| WO | 2015/123408 A1 | 8/2015 |
| WO | 2017/215464 A1 | 12/2017 |

OTHER PUBLICATIONS

IUPAC Compendium of Chemical Terminology; Version 2.3.3 Feb. 24, 2014; p. 1164.*
Stazi, G., "LSD1 inhibitors: a patent review (2010-2015)." Expert Opinion on Therapeutic Patents 26.5 (2016): 565-580.*
International Preliminary Report on Patentability for Application No. PCT/CN2017/087081, dated Dec. 27, 2018.

* cited by examiner

*Primary Examiner* — John M Mauro
(74) *Attorney, Agent, or Firm* — Wolf, Greenfield & Sacks, P.C.

(57) ABSTRACT

The present invention relates to the fields of medicinal chemistry and pharmacotherapy, and specifically relates to the chemical compound of formula (I), and its racemate, R-isomer, S-isomer, pharmaceutically acceptable salt, and mixtures thereof, as well as its method for preparation, a pharmaceutical composition containing said chemical compound, and use as a lysine-specific demethylase 1 (LSD 1) inhibitor. The cyclopropylamine chemical compound to which the present invention relates may be used in the treatment of cancer.

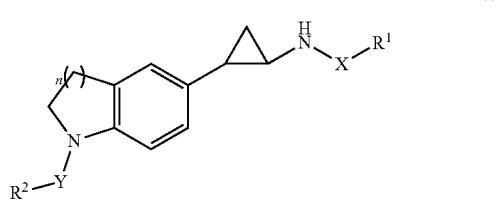

(I)

10 Claims, No Drawings

TRANS-INDOLINE CYCLOPROPYLAMINE CHEMICAL COMPOUND, AND METHOD FOR PREPARATION, PHARMACEUTICAL COMPOSITION, AND USE THEREOF

CROSS-REFERENCE TO RELATED APPLICATIONS

This Application is a national stage filing under 35 U.S.C. § 371 of International Patent Application Serial No. PCT/CN2017/087081, filed Jun. 2, 2017, which claims the benefit of priority to Chinese Patent Application Serial Number 201610390628.6, filed Jun. 3, 2016, the entire contents of each of which are incorporated by reference herein.

FIELD OF THE INVENTION

The present invention relates to the field of medicinal chemistry and pharmacotherapeutics, and in particular a class of fluorine-substituted cyclopropylamine compounds, the preparation thereof, pharmaceutical compositions containing the same, and use thereof as lysine-specific demethylase 1 (LSD1) inhibitors, in particular for the preparation of a medicament for the treatment of diseases such as cancer, leukemia and the like.

BACKGROUND OF THE INVENTION

Epigenetics is a branch of genetics that studies the heritable changes in gene expression by reversible modification of nucleotides or chromosomes without changing the DNA sequence of the gene. The regulatory mechanisms of epigenetics mainly include DNA methylation, histone modification, and non-coding RNA action, etc. In most cases, epigenetic information is stored by altering the chemical modification of cytosine and histones, and such changes in chemical structure will alter the structure of chromatin. Normal epigenetic processes play an important role in life activities such as embryonic development and cell differentiation. Studies have shown that the occurrence of many diseases relates to the abnormality of epigenetic modification. In recent years, epigenetics has become a research hotspot in the fields of biology and medicine. The research on epigenetics is of significance in processes of prevention and treatment of many human diseases.

LSD1 (also known as BHC110, p110b, and NPAO) was confirmed by Shi's group in 2004, of which the structure is highly conserved from yeast to humans. In cells, the demethylation ability of LSD1 is highly specific for genes, substrates, and environments, and produces different (or even opposite) effects on gene expression at different loci. The study found that LSD1 plays an important role in promoting normal cell differentiation, but LSD1 has also been found to be abnormally recruited, thus leading to inappropriate inhibition of downstream abnormal gene targets for leukemia-causing genes (e.g, MLL-AF9). In this case, LSD1 maintains the activity conferred by initial damage activity on leukemia stem cells (LSC), and the cellular effects downstream of LSD1 are also significantly different from normal cell states. No changes in gene expression were found at the most primitive hematopoietic stem cell (HSC) levels during normal hematopoiesis, which is consistent with observations of reduced blood cells induced by the completely opposite LSD1 depletion. Therefore, if LSD1 can produce controlled and reversible toxicity to normal hematopoietic cells, it can be used as a potential drug for the treatment of leukemia.

Therefore, the development of small-molecule LSD1 inhibitors of novel structure has important research significance for the treatment of diseases such as malignant tumors and leukemia.

SUMMARY OF THE INVENTION

The purpose of the present invention is to provide a small molecular LSD1 inhibitor of novel structure.

In the first aspect of the invention, a fluorine-substituted cyclopropylamine compound of the following formula I, and a racemate, R-isomer, S-isomer, pharmaceutically acceptable salt, or mixture thereof are provided:

Formula (I)

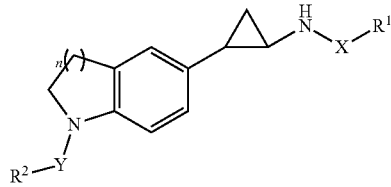

wherein:
n=1, 2;
X is none or $-(CH_2)_{1-4}$, $-CH(Ra)(CH_2)_{0-3}$, $-C(Ra)_2(CH_2)_{0-3}$, C3-C6 cycloalkane, carbonyl or carbonyl-oxo, wherein each Ra is independently C1-C4 alkyl;
Y is sulfonyl, carbonyl or carbonyl-oxo;
$R^1$ is selected from —H, substituted or unsubstituted C1-C12 alkyl, substituted or unsubstituted C3-C12 cycloalkyl, substituted or unsubstituted 3-12 membered heterocyclic group (which comprises monocyclic, cyclo, spiro or bridged ring), substituted or unsubstituted C6-C10 aryl, substituted or unsubstituted 5-12 membered aromatic heterocyclic group, wherein R1 has 0, 1, 2, or 3 substituents selected from the group consisting of halogen, aryl, heteroaryl, C1-C6 alkyl, —SO₂Ra, —NC(O)Ra, —CH₂C(O)ORa, —C(O)ORa, —C(O)Ra, —C(O)NRaRb, substituted amino, amino, carbamido, amide, sulfonamide, aralkyl and heteroarylalkyl; wherein said heterocyclic group comprises 1-3 heteroatoms selected from the group consisting of N, O and S;
each Ra is independently hydrogen, phenyl, phenylmethyl, 3,5-dimethylisoxazol-4-yl, 1,2-dimethyl-1H-imidazol-4-yl, C3-C7 cycloalkyl, C1-C6 alkyl, C1-C4 alkoxy, C1-C3 alkylamino or —NHPh;
Rb is hydrogen or C1-C3 alkyl, or when Ra and Rb are attached to the same atom,
Ra and Rb together form 5- or 6-membered heterocycloalkyl ring;
$R^2$ is selected from substituted or unsubstituted C1-C8 alkyl, substituted or unsubstituted C3-C12 cycloalkyl, substituted or unsubstituted C6-C10 aromatic ring or substituted or unsubstituted 3-12 membered aromatic heterocyclic ring containing 1-4 hetero atoms selected from oxygen, sulfur or nitrogen;
wherein the substituent is selected from the group consisting of deuterium, tritium, halogen, C1-C12 alkyl which is unsubstituted or substituted by 1-3 halogen, C1-C12 alkoxy which is unsubstituted or substituted by 1-3 halogens or phenyls, C2-C12 alkenyl which is unsubstituted or substituted by 1-3 halogens, C3-C6 cycloalkyl which is unsubstituted or substituted by 1-3 halogens, C1-C6 alkyl which is substituted by C1-C6 alkoxy, C1-C6 alkyl substituted by C3-C6 cycloalkyl, hydroxy, cyano, nitro, C1-C6 straight or branched hydroxyalkyl, amino group which is unsubstituted or substituted by 1 or 2 C1-C6 alkyls, carboxyl, hydrosulfuryl, or benzyl group which is unsubstituted or substituted by one or more substituents selected from the group consisting of carboxyl, C2-C6 ester group; or any two substituents on the substituted or unsubstituted alkyl, substituted or unsubstituted cycloalkyl, substituted benzene ring or substituted aromatic heterocyclic ring may be bonded together with the adjacent carbon or hetero atom to form a 5-7 membered heterocyclic ring comprising 1 to 3 heteroatoms selected from the group consisting of N, O and S, and the 5-7 membered heterocyclic ring is optionally substituted with a substituent selected from the group consisting of hydrogen, hydrogen isotopes, halogen, trifluoromethyl, methoxy, C1-C6 straight or branched alkyl which is unsubstituted or substituted with 1-3 halogen, C1-C6 straight or branched alkoxy which is unsubstituted or substituted with 1-3 halogen, or hydroxy;

in the present invention, the halogen is F, Cl, Br or I.

In another preferred embodiment, $R^1$ is selected from substituted or unsubstituted C3-C12 cycloalkyl, substituted or unsubstituted 3-10 membered heterocyclic group (which comprises monocyclic, cyclo, spiro or bridged ring), substituted or unsubstituted C6-C10 aryl, wherein R1 has 0, 1, 2, or 3 substituents selected from the group consisting of halogen, aryl, heteroaryl, C1-C6 alkyl, —SO$_2$Ra, —NC(O)Ra, —CH$_2$C(O)ORa, —C(O)ORa, —C(O)Ra, —C(O)NRaRb, substituted amino, amino, carbamido, amide, sulfonamide, aralkyl and heteroarylalkyl; wherein said heterocyclic ring comprises 1-3 heteroatoms selected from N or O.

In another preferred embodiment, the heterocyclic group contains 1 or 2 hetero atoms selected from N or O.

In another preferred embodiment, $R^2$ is selected from the group consisting of substituted or unsubstituted phenyl, substituted or unsubstituted naphthyl, substituted or unsubstituted 3-7 membered cycloalkyl; wherein "substituted" means that one or more hydrogen atoms on the substituent are substituted with a substituent selected from the group consisting of halogen, C1-4 alkyl, fluoro C1-4 alkyl, C1-4 alkoxy.

In another preferred embodiment, Y is sulfonyl or carbonyl.

In another preferred embodiment, the compound is the compound A1-A72 in the table.

In a second aspect of the invention, a lysine-specific demethylase 1 (LSD1) inhibitor is provided, and the inhibitor comprises a compound according to first aspect of the present invention, or ae enantiomer, diastereomer, racemate, and mixture thereof, and a pharmaceutically acceptable salt, crystalline hydrate, and solvate thereof.

In the third aspect of the present invention, a preparation method for compound (I) of the first aspect of the present invention is provided, which comprises the following steps:

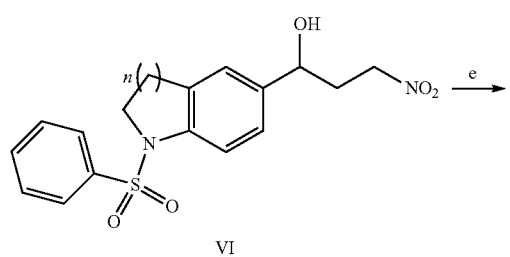

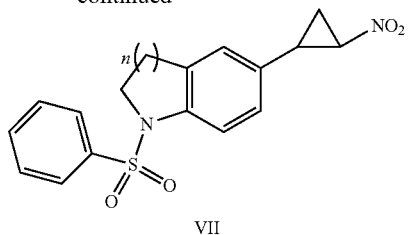

(e) in an inert solvent, using alcohol intermediate (VI) to carry out Mitsunobu reaction with nucleophilic reagent to give trans porphyrin nitrocyclopropane intermediate (VII); and preparing compound of formula (I) with a compound of formula (VII).

Wherein the groups are defined as in the first aspect of the present invention.

In the fourth aspect of the present invention, a preparation method for compound (I) of the first aspect of the present invention is provided, wherein the preparation comprises the following steps:

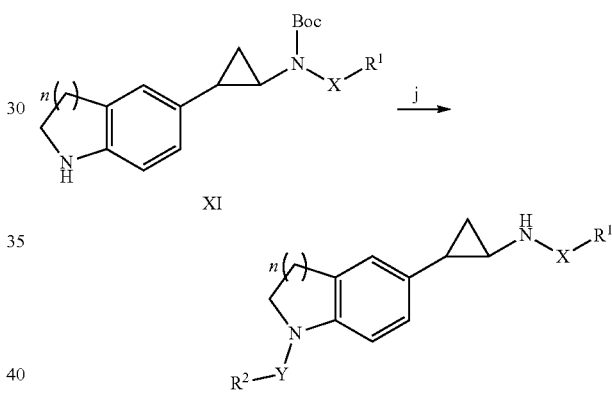

(j) in an inert solvent, reacting formula (XI) compound with acid chloride, and removing the protecting group to give the target product (I);

Wherein the groups are defined as in the first aspect of the present invention.

In the fifth aspect of the invention, a pharmaceutical composition is provided, comprising (A) a therapeutically effective amount of a compound according to the first aspect of the present invention, or a enantiomer, diastereomer, racemate and mixture thereof, and one or more of pharmaceutically acceptable salts, crystalline hydrates, and solvates thereof; and (B) a pharmaceutically acceptable carrier.

In the sixth aspect of the invention, a use of the compound of the first aspect of the present invention, or a enantiomer, diastereomer, racemate and mixture thereof, and a pharmaceutically acceptable salt, hydrate and solvate thereof is provided for the preparation of a medicine for the treatment or prevention of malignant tumor diseases associated with lysine-specific demethylase 1 (LSD1).

In another preferred embodiment, the disease is selected from the group consisting of brain cancer (glioma), glioblastoma, leukemia, Myelodysplastic Syndromes, Cowden's disease, cerebellar dysplastic ganglioneuroma, breast cancer, inflammatory breast cancer, Wilms' tumor, Ewing sarcoma, rhabdomyosarcoma, ependymoma, medulloblastoma, colon cancer, head and neck cancer, kidney cancer, lung cancer, liver cancer, melanoma, kidney cancer, ovarian cancer, pancreatic cancer, prostate cancer, sarcoma, osteosarcoma, bone and thyroid giant cell tumor.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through long-term and intensive research, the inventors has unexpectedly discovered that trans-indoline cyclopropylamine chemical compounds can be used as potent LSD1 inhibitors, and can also be used to prepare medicine for the treatment or prevention of lysine specifically targets demethylase 1 (LSD1) associated malignant neoplasms. The present invention is completed on this basis.

Terms

Unless otherwise specified, the terms used have the general meaning known by those skilled in the art.

In the present invention, the halogen refers to F, Cl, Br or I.

In the present invention, the term "C1-C12 alkyl" refers to linear or branched alkyl with 1 to 12 carbon atoms, including but not limited to methyl, ethyl, propyl, isopropyl, butyl, isobutyl, sec-butyl, tert-butyl, pentyl and hexyl, or the like; preferably ethyl, propyl, isopropyl, butyl, isobutyl, sec-butyl and tert-butyl.

In the present invention, the term "C1-C6 alkoxy" refers to a straight or branched chain alkoxy group having 1 to 6 carbon atoms, including but not limited to methoxy, ethoxy, propoxy, isopropoxy, butoxy, iso-butoxy, butoxy, or the like.

In the present invention, the term "C3-C12 cycloalkyl" refers to a cyclic alkyl group having 3 to 12 carbon atoms on the ring, including but not limited to cyclopropyl, cyclobutyl, cyclopentyl, cyclohexyl, cycloheptyl, cyclooctyl and cyclodecyl. The terms such as "C3-C8 cycloalkyl", "C3-C7 cycloalkyl", and "C3-C6 cycloalkyl" have similar meanings.

In the present invention, the term "C6-C10 aryl" refers to an aryl group having 6 to 10 carbon atoms and not comprising heteroatoms on the ring, such as phenyl, naphthyl and the like. The term "C6 aryl" has a similar meaning.

In the present invention, the term "3-12 membered heterocyclyl" refers to a saturated or unsaturated 3-12 membered ring group having 1 to 3 heteroatoms selected from oxygen, sulfur or nitrogen on the ring, such as oxepanyl. The term "3-7 membered heterocyclyl" has a similar meaning.

The term "3-12 membered heterocyclic ring" refers to a cyclic saturated or partially unsaturated non-aromatic group having 3-12 members, including monocyclic ring, bicyclic ring, spiro ring or bridged ring, wherein the heterocyclic ring comprises at least one ring atom selected from the group consisting of O, S and/or N.

The term "5-12 membered aromatic heterocyclic group" refers to cyclic aromatic groups having 5 to 12 members, wherein the heterocyclic ring comprises at least one ring atom selected from the group consisting of O, S and/or N.

In the present invention, the term "substituted" means that one or more hydrogen atoms on a particular group are replaced by a specific substituent. The specific substituent is a substituent which is correspondingly described in the foregoing, or a substituent which appears in each embodiment. Unless otherwise indicated, a substituted group may have a substituent selected from a particular group at any substitutable position of the group, wherein the substituents may be the same or different at each position. A cyclic substituent, such as a heterocycloalkyl group, may be attached to another ring, such as a cycloalkyl group, to form a spirobicyclic ring system, for example, two rings having a common carbon atom. Those skilled in the art will appreciate that the combinations of substituents contemplated by the present invention are those that are stable or chemically achievable. The substituents, for instance (but not limited to), $C_{1-8}$ alkyl, $C_{2-8}$ alkenyl, $C_{2-8}$ alkynyl, $C_{3-8}$ cycloalkyl, 3- to 12-membered heterocyclic, aryl, heteroaryl, halogen, hydroxy, carboxyl (—COOH), $C_{1-8}$ aldehyde group, $C_{2-10}$ acyl, $C_{2-10}$ ester group, amino, alkoxy and the like.

In particular, the expression "C1-Cn" means that the group has 1-n carbon atoms. For example, the expression C1-C12 means that the group has 1, 2, 3, 4, 5, 6, 7, 8, 9, 10, 11 or 12 carbon atoms; C6-C10 means that the group has 6, 7, 8, 9 or 10 carbon atoms.

The present invention, the term "pharmaceutically acceptable" component refers to substances which are suitable for applying to humans and/or animals without undue harmful side reactions (such as toxicity, stimulation or allergy), i.e., substances of reasonable benefit/risk ratio.

In the present invention, the term "effective amount" refers to an amount in which the therapeutic agents can treat, relieve or prevent the targeted disease, or exhibit detectable treatment or prevention effects. The exact effective amount for a subject will depend on the size and health condition of the subject, the nature and extent of the disorder, and the the therapeutic agent and/or therapeutic agent combination selected for administration. Therefore, it is useless to specify an accurate effective amount in advance. However, for a given situation, the effective amount may be determined by routine experiments, which can be determined by clinicians.

Compound of Formula (I)

The present invention provides a compound of formula (I):

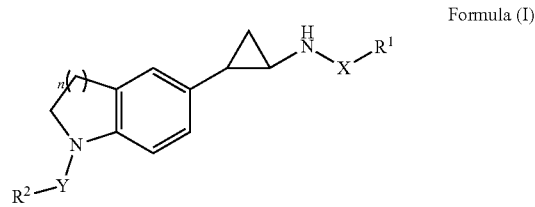

Formula (I)

In a preferred embodiment of the invention, $R^1$, $R^2$, X, Y, n are each independently the group shown in the compounds of Table 1.

In a more preferred embodiment of the present invention, the compounds of general formula (I) of the present invention are preferably specific compounds as follows:

TABLE 1

| No. | Name | Structure |
| --- | --- | --- |
| A1 | Trans-2-(1-(phenylsulfonyl)indolin-5-yl)cyclopropylamine | 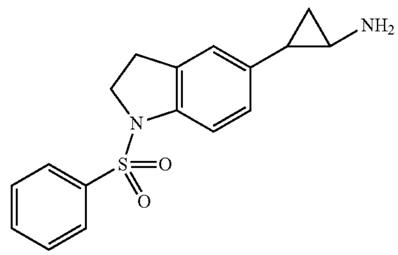 [SMILES: NC1CC1c1ccc2c(c1)CCN2S(=O)(=O)c1ccccc1] |
| A2 | trans-N-phenyl-2-(1-(phenylsulfonyl)indolin-5-yl)cyclopropylamine | 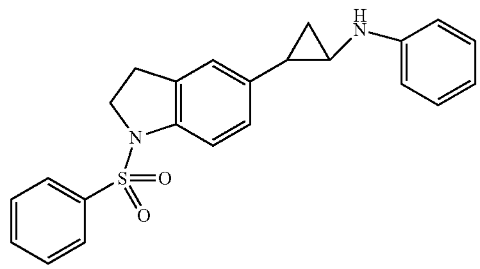 [SMILES: O=S(=O)(c1ccccc1)N1CCc2cc(C3CC3Nc3ccccc3)ccc21] |
| A3 | trans-N-benzyl-2-(1-(phenylsulfonyl)indolin-5-yl)cyclopropylamine | 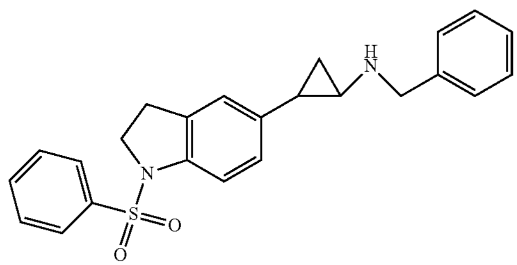 [SMILES: O=S(=O)(c1ccccc1)N1CCc2cc(C3CC3NCc3ccccc3)ccc21] |
| A4 | trans-N-(1-phenylethyl)-2-(1-(phenylsulfonyl)indolin-5-yl)cyclopropylamine | 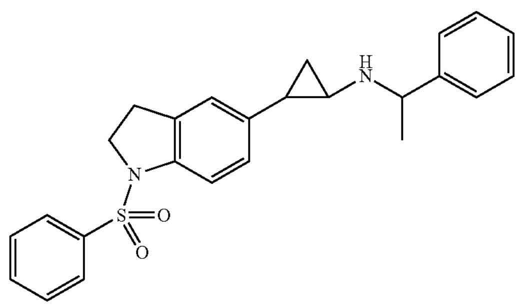 [SMILES: CC(NC1CC1c1ccc2c(c1)CCN2S(=O)(=O)c1ccccc1)c1ccccc1] |
| A5 | trans-N-(4-dimethylamino-benzyl)-2-(1-(phenylsulfonyl)indolin-5-yl)cyclopropylamine | 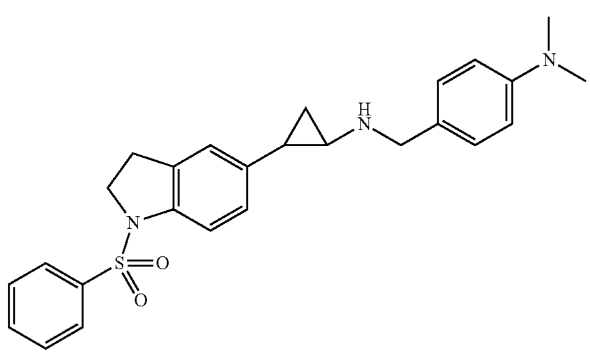 [SMILES: CN(C)c1ccc(CNC2CC2c2ccc3c(c2)CCN3S(=O)(=O)c2ccccc2)cc1] |

TABLE 1-continued

| No. | Name | Structure |
|---|---|---|
| A6 | trans-N-(4-pyridine-methylene)-2-(1-(phenylsulfonyl)indolin-5-yl)cyclopropylamine | 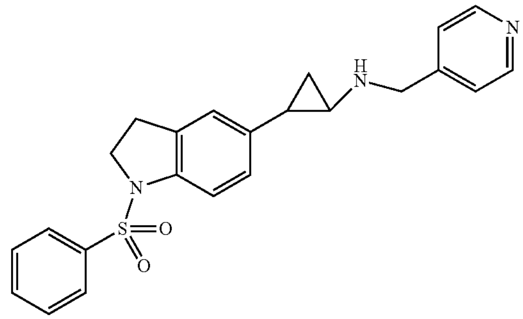 [SMILES: O=S(=O)(c1ccccc1)N1CCc2cc(C3CC3NCc3ccncc3)ccc21] |
| A7 | trans-N-(5-indolylmethylene)-2-(1-(phenylsulfonyl)indolin-5-yl)cyclopropylamine | 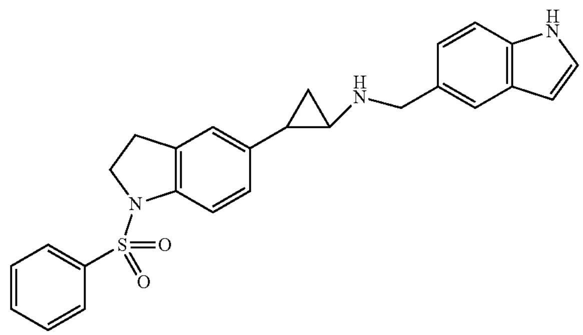 [SMILES: O=S(=O)(c1ccccc1)N1CCc2cc(C3CC3NCc3ccc4[nH]ccc4c3)ccc21] |
| A8 | trans-N-(3-indolylmethylene)-2-(1-(phenylsulfonyl)indolin-5-yl)cyclopropylamine | 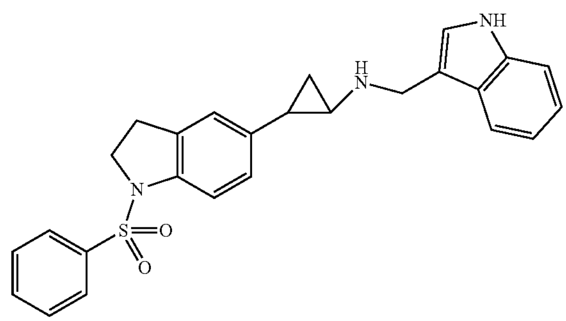 [SMILES: O=S(=O)(c1ccccc1)N1CCc2cc(C3CC3NCc3c[nH]c4ccccc34)ccc21] |
| A9 | trans-N-(2-(1-(phenylsulfonyl)indolin-5-yl)cyclopropyl)cyclohexylamine | 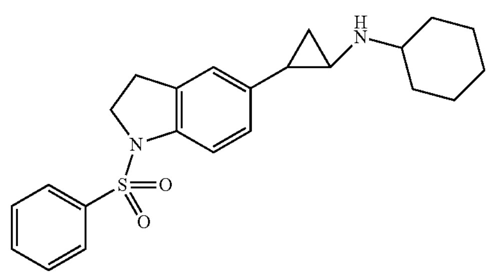 [SMILES: O=S(=O)(c1ccccc1)N1CCc2cc(C3CC3NC3CCCCC3)ccc21] |
| A10 | trans-N-cyclohexamethylene-2-(1-(phenylsulfonyl)indolin-5-yl)cyclopropylamine | 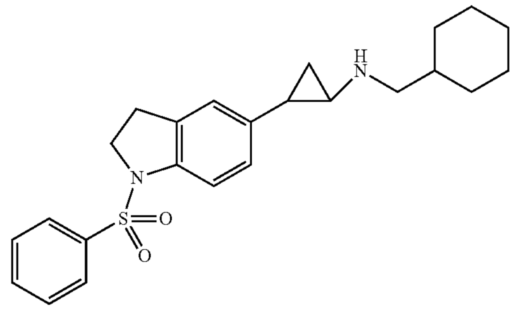 [SMILES: O=S(=O)(c1ccccc1)N1CCc2cc(C3CC3NCC3CCCCC3)ccc21] |

TABLE 1-continued

| No. | Name | Structure |
|---|---|---|
| A11 | trans-N-butyl-2-(1-(phenylsulfonyl)indolin-5-yl)cyclopropylamine | 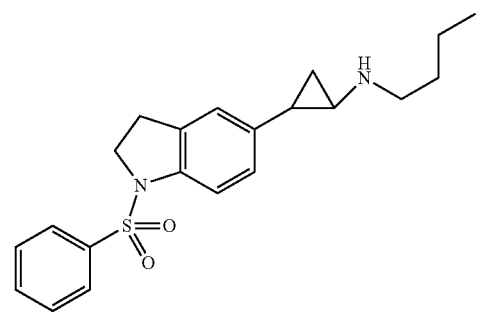 [SMILES: CCCCNC1CC1c1ccc2c(c1)CCN2S(=O)(=O)c1ccccc1] |
| A12 | trans-2-(1-(phenylsulfonyl)indolin-5-yl)-N-((tetrahydro-2H-pyran-4-yl)methyl)cyclopropylamine | 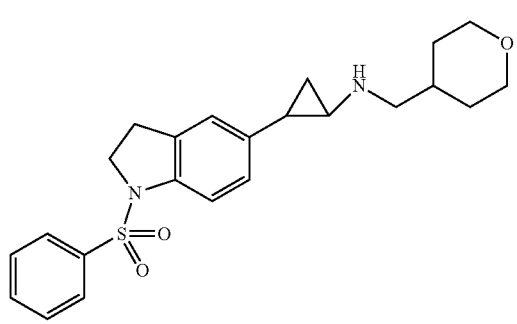 [SMILES: O=S(=O)(c1ccccc1)N1CCc2cc(C3CC3NCC3CCOCC3)ccc21] |
| A13 | trans-N-(2-(1-(phenylsulfonyl)indolin-5-yl)cyclopropyl)tetrahydro-2H-pyran-4-amine | 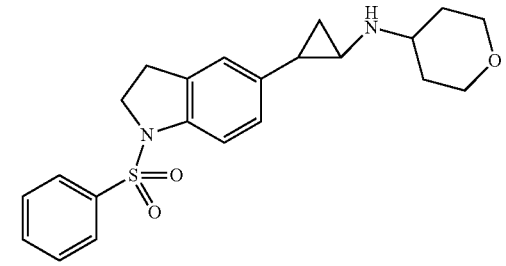 [SMILES: O=S(=O)(c1ccccc1)N1CCc2cc(C3CC3NC3CCOCC3)ccc21] |
| A14 | trans-N-(4-piperidinylmethylene)-2-(1-(phenylsulfonyl)indolin-5-yl)cyclopropylamine | 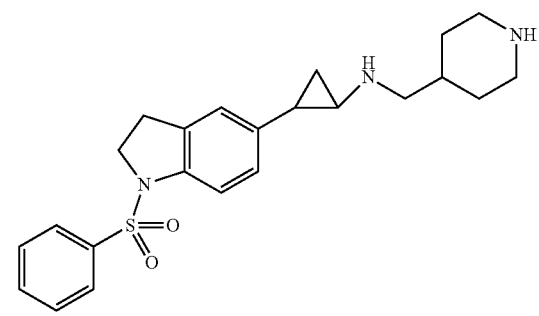 [SMILES: O=S(=O)(c1ccccc1)N1CCc2cc(C3CC3NCC3CCNCC3)ccc21] |
| A15 | trans-N-(4-piperidinyl)-2-(1-(phenylsulfonyl)indolin-5-yl)cyclopropylamine | 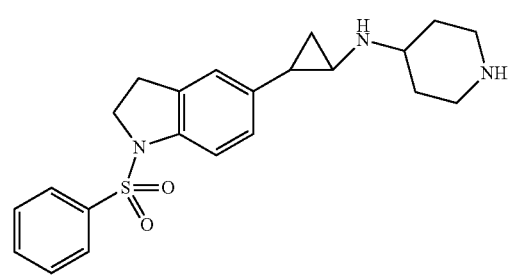 [SMILES: O=S(=O)(c1ccccc1)N1CCc2cc(C3CC3NC3CCNCC3)ccc21] |

TABLE 1-continued

| No. | Name | Structure |
|---|---|---|
| A16 | trans-N-(4-piperidinylethyl)-2-(1-(phenylsulfonyl)porphyrin-5-yl)cyclopropylamine | 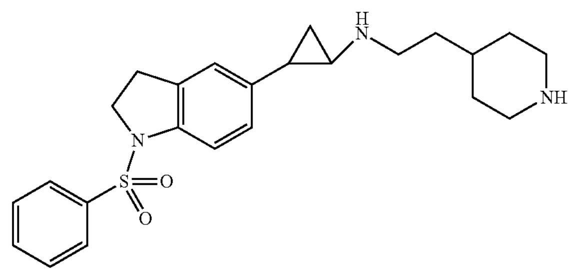 [SMILES: O=S(=O)(c1ccccc1)N1CCc2cc(C3CC3NCCC3CCNCC3)ccc21] |
| A17 | trans-N-(azetidin-3-ylmethyl)-2-(1-(phenylsulfonyl)indolin-5-yl)cyclopropylamine | 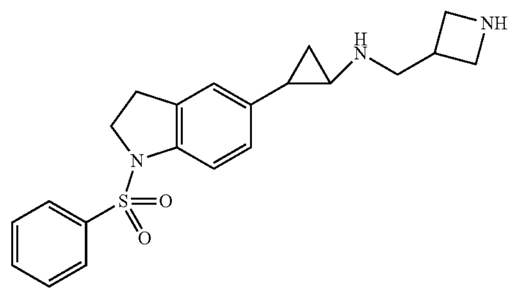 [SMILES: O=S(=O)(c1ccccc1)N1CCc2cc(C3CC3NCC3CNC3)ccc21] |
| A18 | trans-4-((2-(1-(phenylsulfonyl)indolin-5-yl)cyclopropylamino)methyl)cyclohexylamine | 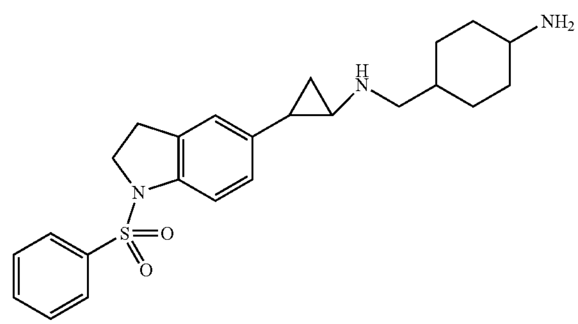 [SMILES: NC1CCC(CNC2CC2c2ccc3c(c2)CCN3S(=O)(=O)c2ccccc2)CC1] |
| A19 | trans-N1-(2-(1-(phenylsulfonyl)indolin-5-yl)cyclopropyl)cyclohexane-1,4-diamine | 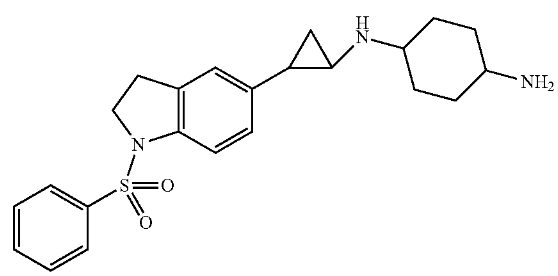 [SMILES: NC1CCC(NC2CC2c2ccc3c(c2)CCN3S(=O)(=O)c2ccccc2)CC1] |
| A20 | trans-N-(2-(1-(phenylsulfonyl)indolin-5-yl)cyclopropyl)-7-azaspiro[3.5]nonane-2-amine | 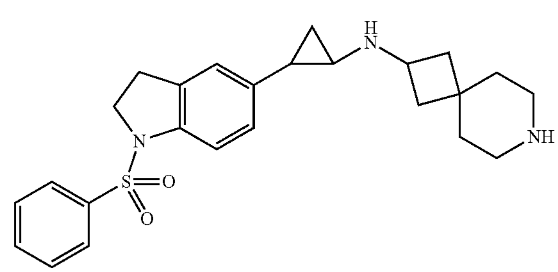 [SMILES: O=S(=O)(c1ccccc1)N1CCc2cc(C3CC3NC3CC4(CCNCC4)C3)ccc21] |

TABLE 1-continued

| No. | Name | Structure |
|---|---|---|
| A21 | trans-N-((4-methylpiperidin-4-yl)methyl)-2-(1-(phenylsulfonyl)indolin-5-yl)cyclopropylamine | 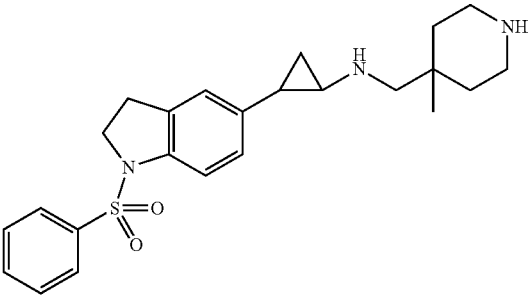 [SMILES: CC1(CNC2CC2c2ccc3c(c2)CCN3S(=O)(=O)c2ccccc2)CCNCC1] |
| A22 | trans-4-((2-(1-(phenylsulfonyl)indolin-5-yl)cyclopropylamino)methyl)piperidine-4-carboxylic acid | 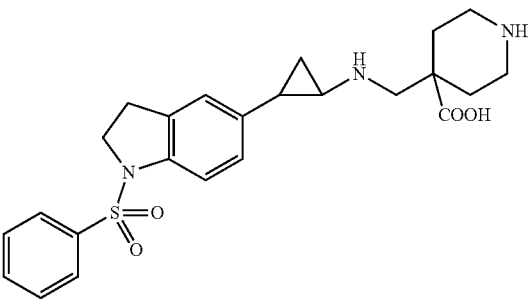 [SMILES: O=C(O)C1(CNC2CC2c2ccc3c(c2)CCN3S(=O)(=O)c2ccccc2)CCNCC1] |
| A23 | trans-N-((1-methylpiperidin-4-yl)methyl)-2-(1-(phenylsulfonyl)indolin-5-yl)cyclopropylamine | 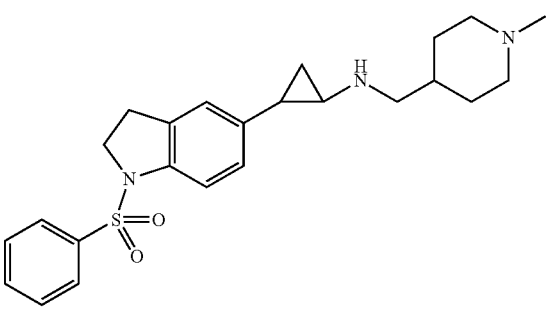 [SMILES: CN1CCC(CNC2CC2c2ccc3c(c2)CCN3S(=O)(=O)c2ccccc2)CC1] |
| A24 | trans-N-((1-benzylpiperidin-4-yl)methyl)-2-(1-(phenylsulfonyl)indolin-5-yl)cyclopropylamine | 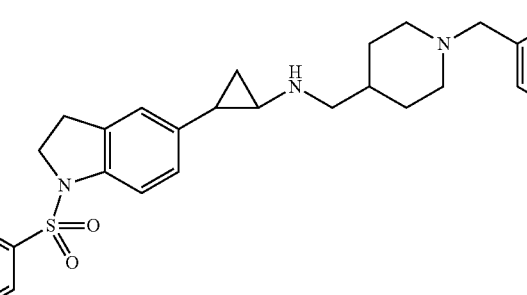 |
| A25 | Trans-tert-butyl 4-((4-((2-(1-(phenylsulfonyl))indolin-5-yl)cyclopropylamino)methyl)piperidin-1-yl)methyl)benzoate | 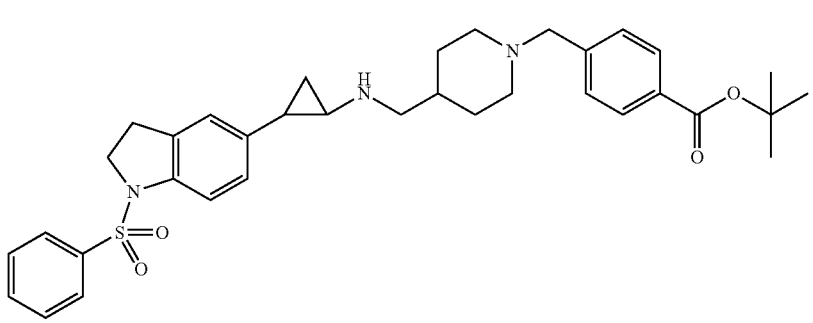 [SMILES: CC(C)(C)OC(=O)c1ccc(CN2CCC(CNC3CC3c3ccc4c(c3)CCN4S(=O)(=O)c3ccccc3)CC2)cc1] |

TABLE 1-continued

| No. | Name | Structure |
|---|---|---|
| A26 | Trans-4-((4-((2-(1-(phenylsulfonyl))indolin-5-yl)cyclopropylamino)methyl)piperidin-1-yl)methyl)benzoic acid | 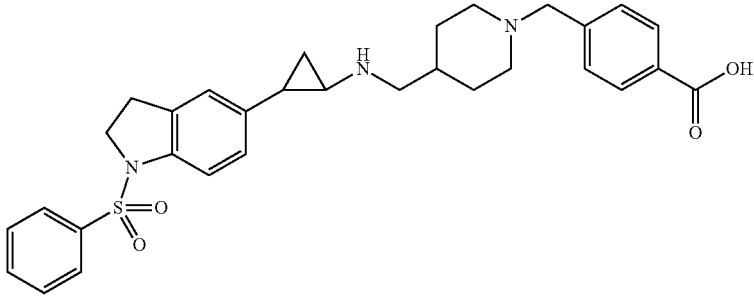 [SMILES: O=C(O)c1ccc(CN2CCC(CNC3CC3c3ccc4c(c3)CCN4S(=O)(=O)c3ccccc3)CC2)cc1] |
| A27 | Trans-tert-butyl 4-((2-(1-(phenylsulfonyl)indolin-5-yl)cyclopropylamino)methyl)piperidine-1-carboxylate | 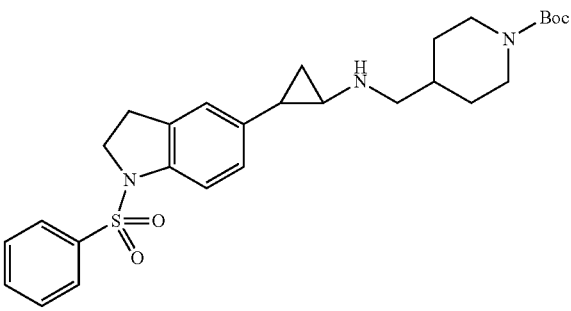 [SMILES: CC(C)(C)OC(=O)N1CCC(CNC2CC2c2ccc3c(c2)CCN3S(=O)(=O)c2ccccc2)CC1] |
| A28 | Trans-benzyl 4-((2-(1-(phenylsulfonyl)indolin-5-yl)cyclopropylamino)methyl)piperidine-1-carboxylate | 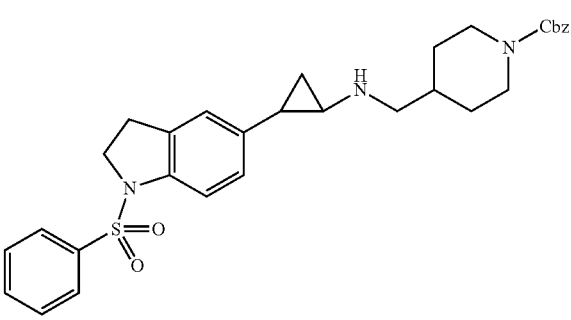 |
| A29 | Trans-tert-butyl 4-(2-(1-(phenylsulfonyl)indolin-5-yl)cyclopropylcarbamoyl)piperidine-1-carboxylate | 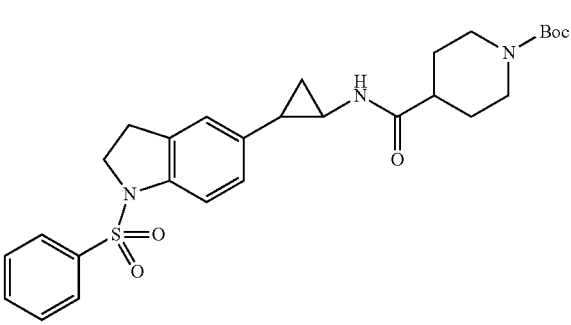 [SMILES: CC(C)(C)OC(=O)N1CCC(C(=O)NC2CC2c2ccc3c(c2)CCN3S(=O)(=O)c2ccccc2)CC1] |
| A30 | Trans-2-(1-(phenylsulfonyl)indolin-5-yl)-N-(1-(piperidin-4-yl)ethyl)cyclopropylamine | 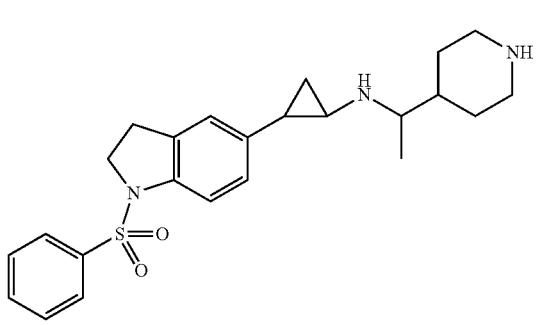 [SMILES: CC(NC1CC1c1ccc2c(c1)CCN2S(=O)(=O)c1ccccc1)C1CCNCC1] |

TABLE 1-continued

| No. | Name | Structure |
|---|---|---|
| A31 | Trans-2-(1-(phenylsulfonyl)indolin-5-yl)-N-(2-(piperidin-4-yl)propan-2-yl)cyclopropylamine | 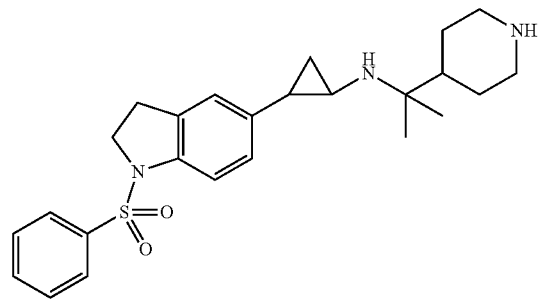 [SMILES: CC(C)(NC1CC1c1ccc2c(c1)CCN2S(=O)(=O)c1ccccc1)C1CCNCC1] |
| A32 | Trans-2-(1-(biphenyl-4-ylsulfonyl)indolin-5-yl)-N-(piperidin-4-ylmethyl)cyclopropylamine | 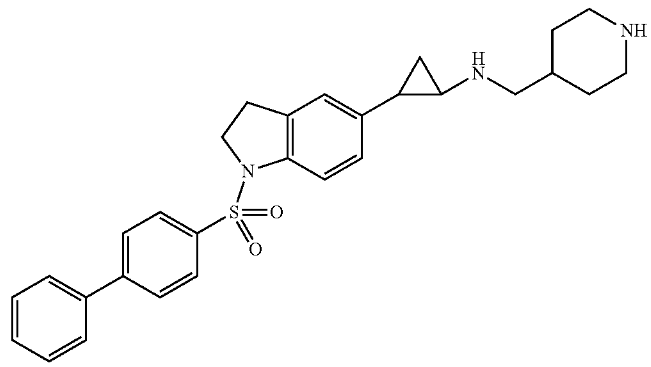 [SMILES: O=S(=O)(c1ccc(-c2ccccc2)cc1)N1CCc2cc(C3CC3NCC3CCNCC3)ccc21] |
| A33 | Trans-2-(1-(naphthalen-2-ylsulfonyl)indolin-5-yl)-N-(piperidin-4-ylmethyl)cyclopropylamine | 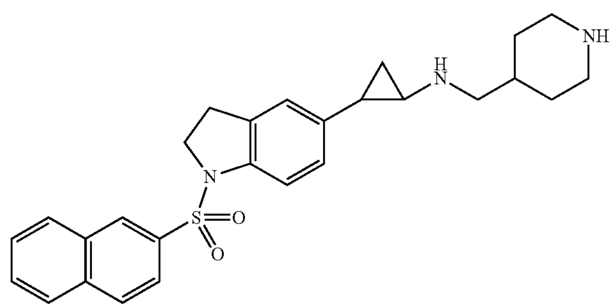 [SMILES: O=S(=O)(c1ccc2ccccc2c1)N1CCc2cc(C3CC3NCC3CCNCC3)ccc21] |
| A34 | trans-N-(piperidin-4-ylmethyl)-2-(1-(4-(trifluoromethyl)benzenesulfonyl)indolin-5-yl)cyclopropylamine | 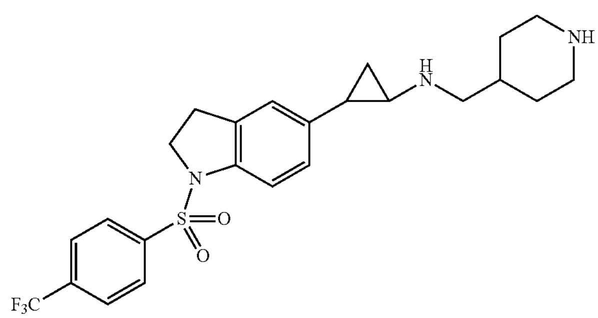 [SMILES: O=S(=O)(c1ccc(C(F)(F)F)cc1)N1CCc2cc(C3CC3NCC3CCNCC3)ccc21] |
| A35 | trans-N-(piperidin-4-ylmethyl)-2-(1-(3-(trifluoromethyl)benzenesulfonyl)indolin-5-yl)cyclopropylamine | 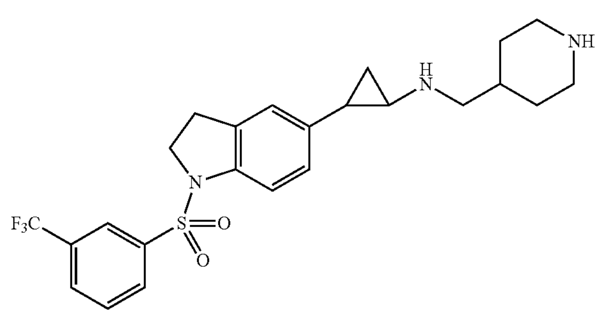 [SMILES: O=S(=O)(c1cccc(C(F)(F)F)c1)N1CCc2cc(C3CC3NCC3CCNCC3)ccc21] |

TABLE 1-continued

| No. | Name | Structure |
|---|---|---|
| A36 | trans-N-(piperidin-4-ylmethyl)-2-(1-(2-(trifluoromethyl)benzenesulfonyl)indolin-5-yl)cyclopropylamine | 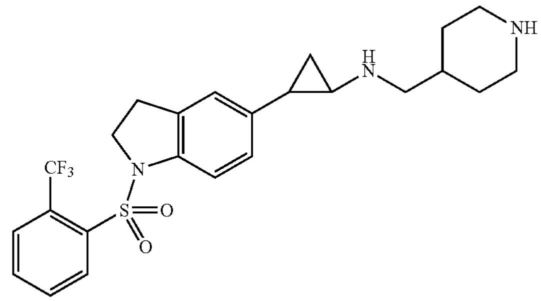 [SMILES: O=S(=O)(c1ccccc1C(F)(F)F)N1CCc2cc(C3CC3NCC3CCNCC3)ccc21] |
| A37 | trans-N-(piperidin-4-ylmethyl)-2-(1-(m-toluenesulfonyl)indolin-5-yl)cyclopropylamine | 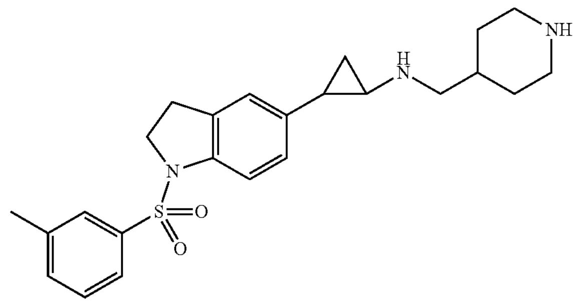 [SMILES: Cc1cccc(S(=O)(=O)N2CCc3cc(C4CC4NCC4CCNCC4)ccc32)c1] |
| A38 | trans-2-(1-(3-chlorobenzenesulfonyl)indolin-5-yl)-N-(piperidin-4-ylmethyl)cyclopropylamine | 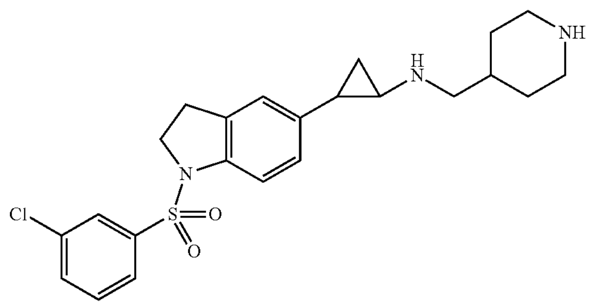 [SMILES: O=S(=O)(c1cccc(Cl)c1)N1CCc2cc(C3CC3NCC3CCNCC3)ccc21] |
| A39 | trans-2-(1-(3-methoxybenzenesulfonyl)indolin-5-yl)-N-(piperidin-4-ylmethyl)cyclopropylamine | 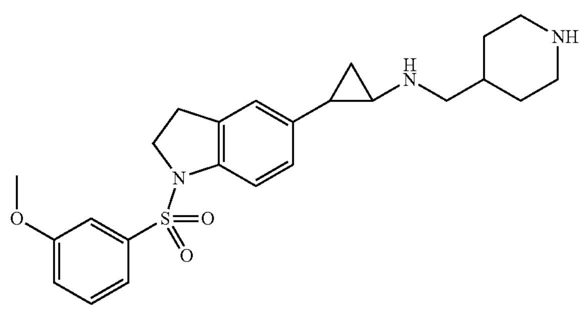 [SMILES: COc1cccc(S(=O)(=O)N2CCc3cc(C4CC4NCC4CCNCC4)ccc32)c1] |
| A40 | Trans-2-(1-(methylsulfonyl)indolin-5-yl)-N-(piperidin-4-ylmethyl)cyclopropylamine | 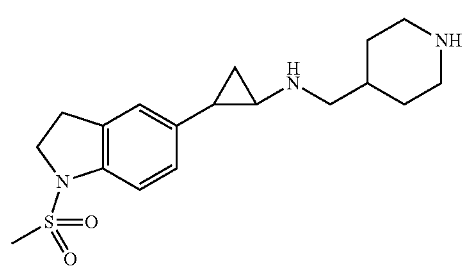 [SMILES: CS(=O)(=O)N1CCc2cc(C3CC3NCC3CCNCC3)ccc21] |

TABLE 1-continued

| No. | Name |
|---|---|
| A41 | trans-N-(piperidin-4-ylmethyl)-2-(1-(propylsulfonyl)indolin-5-yl)cyclopropylamine |
| A42 | trans-N-(piperidin-4-ylmethyl)-2-(1-(trifluoromethanesulfonyl)indolin-5-yl)cyclopropylamine |
| A43 | trans-2-(1-(cyclohexylsulfonyl)indolin-5-yl)-N-(piperidin-4-ylmethyl)cyclopropylamine |
| A44 | trans-2-(1-(tert-butylsulfonyl)indolin-5-yl)-N-(piperidin-4-ylmethyl)cyclopropylamine |
| A45 | trans-phenyl(5-(2-(piperidin-4-ylmethylamino)cyclopropyl)indolin-1-yl)methanone |

TABLE 1-continued

| No. | Name |
|---|---|
| A46 | Trans-naphthalen-2-yl(5-(2-(piperidin-4-ylmethylamino)cyclopropyl)indolin-1-yl)methanone |
| A47 | Trans-biphenyl-4-yl(5-(2-(piperidin-4-ylmethylamino)cyclopropyl)indolin-1-yl)methanone |
| A48 | Trans-(5-(2-(piperidin-4-ylmethylamino)cyclopropyl)indolin-1-yl)(3-(trifluoromethyl)phenyl)methanone |
| A49 | Trans-2-phenyl-1-(5-(2-(piperidin-4-ylmethylamino)cyclopropyl)indolin-1-yl)ethanone |
| A50 | Trans-benzyl-5-(2-(piperidin-4-ylmethylamino)cyclopropyl)indoline-1-carboxylate |

TABLE 1-continued

| No. | Name | Structure |
|---|---|---|
| A51 | Trans-1-(5-(2-(piperidin-4-ylmethylamino)cyclopropyl)indolin-1-yl)ethanone | 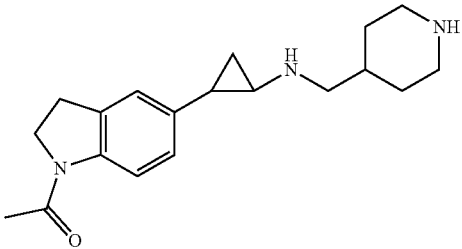 [SMILES: CC(=O)N1CCc2cc(C3CC3NCC3CCNCC3)ccc21] |
| A52 | Trans-2,2,2-trifluoro-1-(5-(2-(piperidin-4-ylmethylamino)cyclopropyl)indolin-1-yl)ethanone | 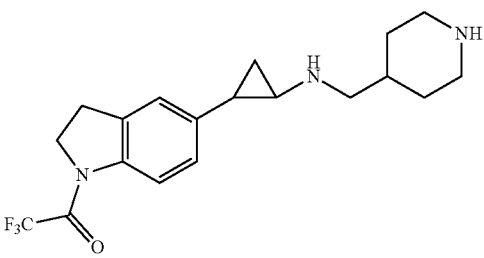 |
| A53 | Trans-1-(5-(2-(piperidin-4-ylmethylamino)cyclopropyl)indolin-1-yl)propan-1-one | 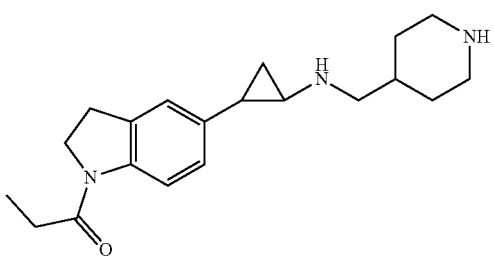 [SMILES: CCC(=O)N1CCc2cc(C3CC3NCC3CCNCC3)ccc21] |
| A54 | Trans-1-(5-(2-(piperidin-4-ylmethylamino)cyclopropyl)indolin-1-yl)butan-1-one | 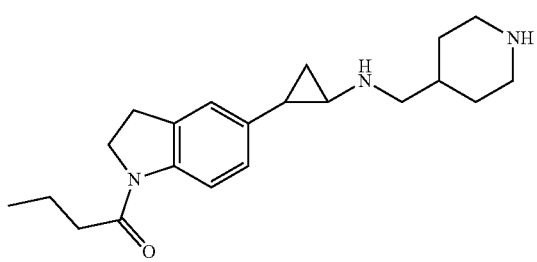 [SMILES: CCCC(=O)N1CCc2cc(C3CC3NCC3CCNCC3)ccc21] |
| A55 | Trans-1-(5-(2-(piperidin-4-ylmethylamino)cyclopropyl)indolin-1-yl)pentan-1-one | 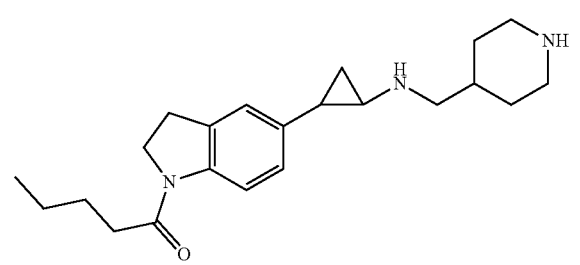 [SMILES: CCCCC(=O)N1CCc2cc(C3CC3NCC3CCNCC3)ccc21] |
| A56 | Trans-3-methoxy-1-(5-(2-(piperidin-4-ylmethylamino)cyclopropyl)indolin-1-yl)propan-1-one | 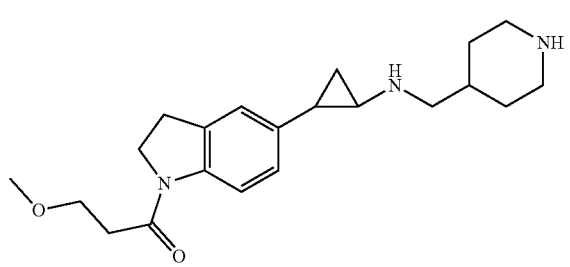 [SMILES: COCCC(=O)N1CCc2cc(C3CC3NCC3CCNCC3)ccc21] |

TABLE 1-continued

| No. | Name |
|---|---|
| A57 | Trans-2-methyl-1-(5-(2-(piperidin-4-ylmethylamino)cyclopropyl)indolin-1-yl)propan-1-one |
| A58 | Trans-2,2-dimethyl-1-(5-(2-(piperidin-4-ylmethylamino)cyclopropyl)indolin-1-yl)propan-1-one |
| A59 | Trans-cyclohexyl (5-(2-(piperidin-4-ylmethylamino)cyclopropyl)indolin-1-yl)methanone |
| A60 | Trans-cycloheptyl (5-(2-(piperidin-4-ylmethylamino)cyclopropyl)indolin-1-yl)methanone |
| A61 | Trans-cyclopentyl (5-(2-(piperidin-4-ylmethylamino)cyclopropyl)indolin-1-yl)methanone |

TABLE 1-continued

| No. | Name | Structure |
|---|---|---|
| A62 | Trans-cyclobutyl (5-(2-(piperidin-4-ylmethylamino) cyclopropyl)indolin-1-yl)methanone | 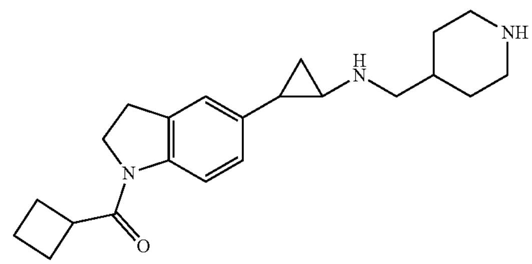 [SMILES: O=C(C1CCC1)N1CCc2cc(C3CC3NCC3CCNCC3)ccc21] |
| A63 | Trans-cyclopropyl (5-(2-(piperidin-4-ylmethylamino) cyclopropyl)indolin-1-yl)methanone | 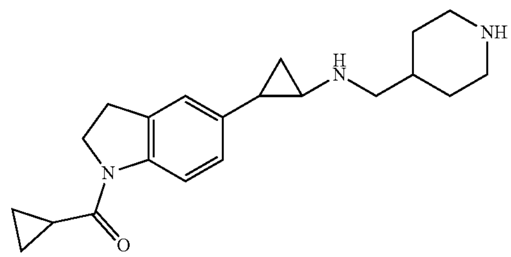 [SMILES: O=C(C1CC1)N1CCc2cc(C3CC3NCC3CCNCC3)ccc21] |
| A64 | trans-N-(2-(1-(phenylsulfonyl)-1,2, 3,4-tetrahydroquinolin-6-yl) cyclopropyl)aniline | 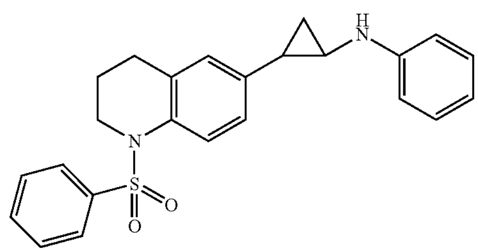 [SMILES: O=S(=O)(c1ccccc1)N1CCCc2cc(C3CC3Nc3ccccc3)ccc21] |
| A65 | trans-N-benzyl-2-(1-(phenylsulfonyl)- 1,2,3,4-tetrahydroquinolin-6-yl) cyclopropylamine | 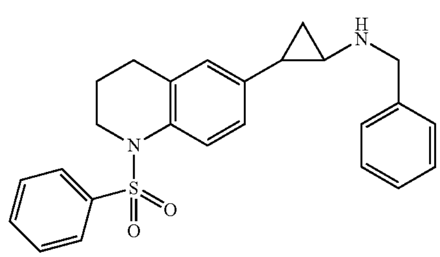 [SMILES: O=S(=O)(c1ccccc1)N1CCCc2cc(C3CC3NCc3ccccc3)ccc21] |
| A66 | trans-N-(2-(1-(phenylsulfonyl)-1,2, 3,4-tetrahydroquinolin-6-yl) cyclopropyl)piperidin-4-amine | 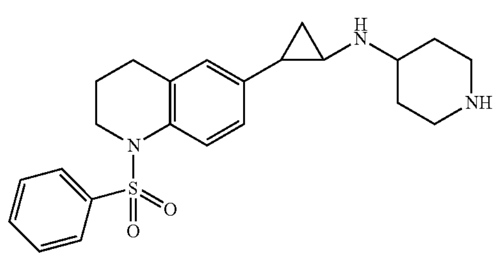 [SMILES: O=S(=O)(c1ccccc1)N1CCCc2cc(C3CC3NC3CCNCC3)ccc21] |
| A67 | Trans-2-(1-(phenylsulfonyl)-1,2,3, 4-tetrahydroquinolin-6-yl)-N-(piperidin- 4-ylmethyl)cyclopropylamine | 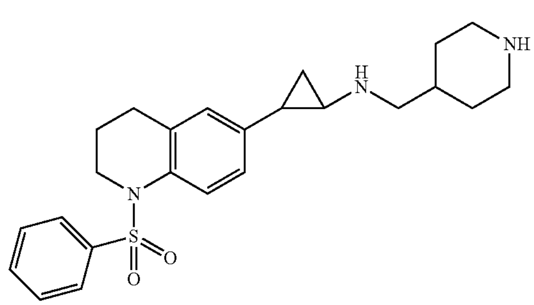 [SMILES: O=S(=O)(c1ccccc1)N1CCCc2cc(C3CC3NCC3CCNCC3)ccc21] |

TABLE 1-continued

| No. | Name |
|---|---|
| A68 | trans-N-(piperidin-4-ylmethyl)-2-(1-(propylsulfonyl)-1,2,3,4-tetrahydroquinolin-6-yl)cyclopropylamine |
| A69 | trans-2-(1-(cyclohexylsulfonyl)-1,2,3,4-tetrahydroquinolin-6-yl)-N-(piperidin-4-ylmethyl)cyclopropylamine |
| A70 | trans-phenyl(6-(2-(piperidin-4-ylmethylamino)cyclopropyl)-3,4-dihydroquinolin-1(2H)-yl)methanone |
| A71 | trans-1-(6-(2-(piperidin-4-ylmethylamino)cyclopropyl)-3,4-dihydroquinolin-1(2H)-yl)butan-1-one |
| A72 | trans-cyclohexyl(6-(2-(piperidin-4-ylmethylamino)cyclopropyl)-3,4-dihydroquinolin-1(2H)-yl)methanone |

The compounds of the invention have asymmetric centers, chiral axes and chiral planes, thus may exist in the form of racemates, R-isomers or S-isomers. Those skilled in the art will be able to provide the R-isomer and/or the S-isomer by seperating the racemate by conventional techniques.

The present invention further provides a pharmaceutically acceptable salt of a compound of formula I, for example, a conventional pharmaceutically acceptable salt formed by a compound of formula I with an inorganic or organic acid. For example, conventional pharmaceutically acceptable salts may be prepared by reacting a compound of formula I with an inorganic mineral acid, such as hydrochloric acid, hydrobromic acid, sulfuric acid, nitric acid, aminosulfonic acid and phosphoric acid, and the like, and organic acids include citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-anilinesulfonic acid, 2-acetoxybenzoic acid and isethionic acid; or sodium, potassium, calcium, aluminum or ammonium salts of the compound of formula I with an inorganic base; or a salt formed by compound of formula I with an organic base, such as methanamine salt, ethylamine salt or ethanolamine salt.

The Preparation of Compound of Formula I

Another aspect of the present invention provides a process for the preparation of a compound of formula I, which is carried out according to the following scheme 1:

The compound of the formula (I) can be prepared by the method shown in the following Scheme 1. An intermediate (III) is obtained by using indoline or 1,2,3,4-tetrahydroquinoline(II) as a starting material to react with benzenesulfonyl chloride. Then intermediate (IV) is provided by Friedel-Crafts acylation with chloropropionyl chloride, which is then nitrated with sodium nitrite to give intermediate (V). The obtained intermediate is reduced by sodium borohydride to obtain an alcohol intermediate (VI), followed by Mitsunobu reaction in a trans molecule to obtain a trans porphyrin nitrocyclopropane intermediate (VII), and then reduced with zinc hydride powder to provide intermediate (VIII). Intermediate (IX) is obtained from intermediate (VIII) through reductive amination, coupling and condensation, which is then protected by t-butoxycarbonyl to give intermediate (X). Intermediate (XI) is obtained by removing benzenesulfonyl group under magnesium reduction conditions. Finally, the salt-formed target product (I) is obtained through reaction with an acid chloride and removal of the protecting group in a dioxane hydrochloride solution.

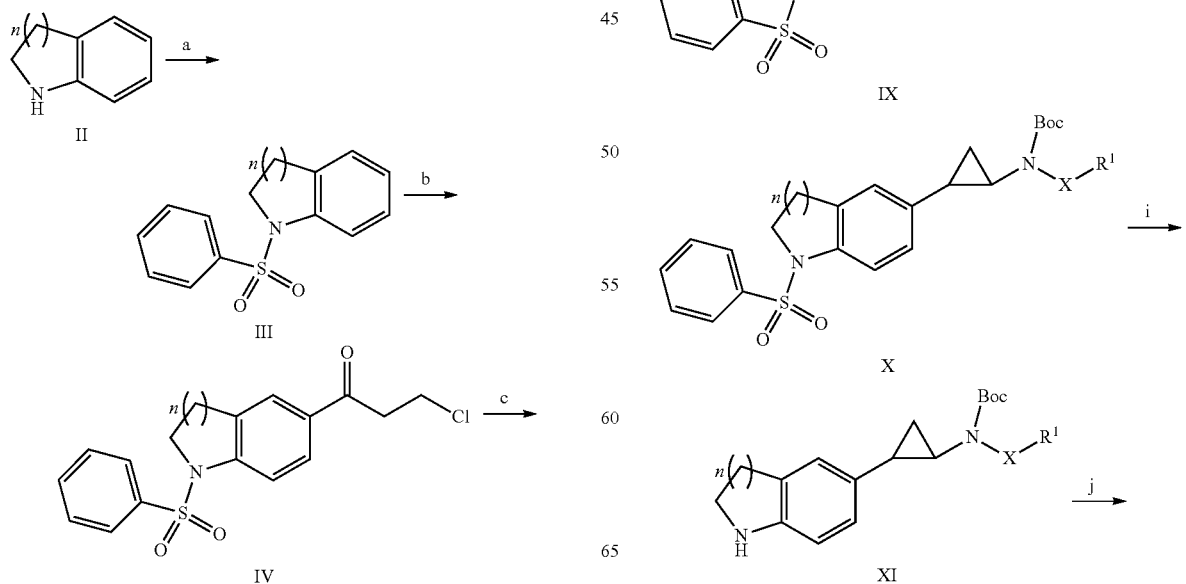

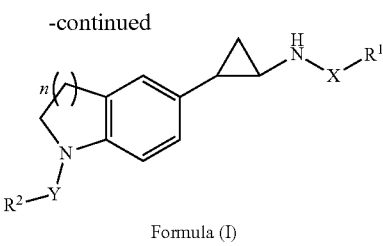

Formula (I)

Pharmaceutical Composition and the Administration Thereof

Since the compound of the present invention has excellent lysine-specific demethylase 1 (LSD1) inhibitory activity, the compound of the present invention and various crystal forms, pharmaceutically acceptable inorganic or organic salts, hydrates or solvates thereof, and a pharmaceutical composition containing the compound of the present invention as a main active ingredient can be used for the treatment, prevention, and alleviation of diseases associated with lysine-specific demethylase 1 (LSD1) activity. According to the prior art, the compound of the present invention can be used in drugs for prevention and treatment of metabolic diseases such as hyperlipidemia, hypercholesterolemia, hypertriglyceridemia, fatty liver deformation, atherosclerosis, obesity, and the like. The compound disclosed in the present invention can also be used in the treatment of brain cancer (glioma), glioblastoma, leukemia, Myelodysplastic Syndromes, Cowden's disease, cerebellar dysplastic ganglioneuroma, breast cancer, inflammatory breast cancer, Wilms' tumor, Ewing sarcoma, rhabdomyosarcoma, ependymoma, medulloblastoma, colon cancer, head and neck cancer, kidney cancer, lung cancer, liver cancer, melanoma, kidney cancer, ovarian cancer, pancreatic cancer, prostate cancer, sarcoma, osteosarcoma, bone and thyroid giant cell tumor, etc.

The pharmaceutical composition of the invention comprises the compound of the present invention or the pharmaceutically acceptable salts thereof in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 0.05-200 mg of the compound of the invention per dose, preferably, 0.1 mg-100 mg of the compound of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administered alone, or in combination with any other pharmaceutically acceptable compounds.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 5-500 mg. The compounds and pharmaceutical compositions of the present invention can be administered via mouth, nose, skin, lungs or gastrointestinal tract, most preferably via mouth. The most preferred daily dose is 0.01-200 mg/kg body weight in one dose, or 0.01-100 mg/kg body weight in divided doses. Regardless of the method of administration, the individual's optimal dose should be determined based on the specific treatment. Usually, the most suitable dose is found by starting at a small dose, and gradually increasing the dose. Of course, the particular dose should also depend on various factors, such as the route of administration, patient healthy status, which are well within the skills of an experienced physician.

Compared with the Prior Art, the Main Advantages of the Present Invention Includes (1) a lysine-specific demethylase 1 (LSD1) inhibitor compound and derivatives thereof with novel structure are provided, and the preparation method thereof possesses advantages, such as mild reaction conditions, abundant raw material resources, easy operation and post-treatment, and good selectivity, etc. The compounds described have excellent lysine-specific demethylase 1 (LSD1) inhibitory activity.

(2) an LSD1 inhibitor is provided which exhibits excellent LSD1 inhibitory activity and tumor cell inhibitory activity in vitro.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1 Trans-2-(1-(phenylsulfonyl)indolin-5-yl)cyclopropylamine (A1)

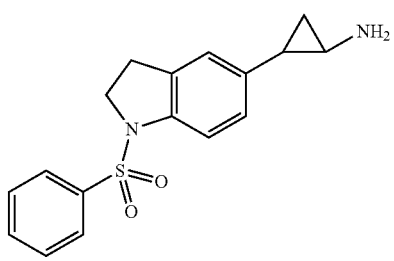 [SMILES: NC1CC1c1ccc2c(c1)CCN2S(=O)(=O)c1ccccc1]

1.1 Synthesis of 1-(phenylsulfonyl)indoline

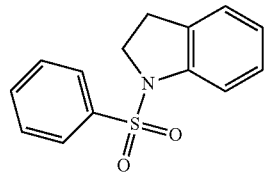 [SMILES: O=S(=O)(c1ccccc1)N1CCc2ccccc21]

In an ice-bath, triethylamine (163 mL, 1.17 mol) was added to a solution of indoline (100 g, 839.18 mmol) in dichloromethane (1 L) under stirring, and then benzene sulfonyl chloride (128 mL, 1.01 mol) was added slowly dropwise. After one hour, it was slowly warmed to room temperature and stirred overnight. After verified by TLC that the reaction was completed, deionized water (200 mL) was slowly added under an ice bath. The organic layer was washed successively with deionized water (1.0 L), saturated aqueous sodium bicarbonate (1.0 L) and saturated brine (1.0 L) for one time. The obtained organic layer was dried over anhydrous sodium sulfate and concentrated under reduced pressure to provide a crude product. Finally, the crude product was purified through recrystallization with ethanol under heating to afford an intermediate (201 g, 92% yield). $^1$H NMR (400 MHz, DMSO) δ 7.82 (d, J=7.7 Hz, 2H), 7.67 (d, J=7.4 Hz, 1H), 7.57 (t, J=7.7 Hz, 2H), 7.49 (d, J=8.1 Hz, 1H), 7.20 (t, J=7.8 Hz, 1H), 7.15 (d, J=7.4 Hz, 1H), 6.98 (t, J=7.4 Hz, 1H), 3.92 (t, J=8.4 Hz, 2H), 2.89 (t, J=8.4 Hz, 2H). LRMS [M+H]$^+$: 260.0.

1.2 Synthesis of 3-Chloro-1-(1-(phenylsulfonyl)indolin-5-yl)propan-1-one

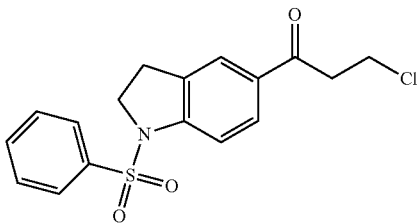 [SMILES: O=C(CCCl)c1ccc2c(c1)CCN2S(=O)(=O)c1ccccc1]

In an ice bath, 3-chloropropionyl chloride (81 mL, 848.36 mmol) was slowly added dropwise to the reaction liquid of aluminum trichloride (113 g, 848.36 mmol) in 1,2-dichloroethane (1.0 L) under stirring. After 1 hour, the intermediate 1-(phenylsulfonyl)indoline (200 g, 771.24 mmol) was added portionwise and then warmed to room temperature for six hours. After verified by TLC that the reaction was completed, the reaction solution was slowly poured into 1.0 L of ice-water mixture (ice cubes were added during the process so as to prevent the temperature from being too high). The organic layer was washed successively with deionized water (1.0 L), saturated aqueous sodium bicarbonate (1.0 L) and saturated brine (1.0 L) for one time. The obtained organic layer was dried over anhydrous sodium sulfate and concentrated under reduced pressure to provide a crude product. Finally, the crude product was crushed, smashed and added into ethanol (700 mL) and stirred overnight to obtain a solid 3-chloro-1-(1-(phenylsulfonyl)indolin-5-yl)propan-1-one (263 g, 97% yield). $^1$H NMR (400 MHz, DMSO) δ 7.91-

7.86 (m, 3H), 7.79 (s, 1H), 7.72 (t, J=7.4 Hz, 1H), 7.61 (t, J=7.8 Hz, 2H), 7.56 (d, J=8.5 Hz, 1H), 4.01 (t, J=8.6 Hz, 2H), 3.89 (t, J=6.3 Hz, 2H), 3.46 (t, J=6.3 Hz, 2H), 3.05 (t, J=8.5 Hz, 2H). LRMS [M+H]⁺: 350.0.

1.3 Synthesis of 3-nitro-1-(1-(phenylsulfonyl)indolin-5-yl)propan-1-one

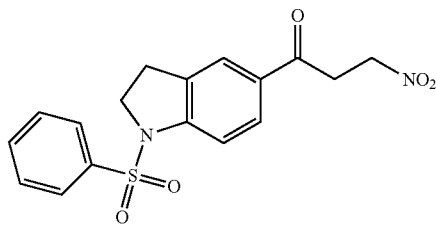 [SMILES: O=C(CC[N+](=O)[O-])c1ccc2c(c1)CCN2S(=O)(=O)c1ccccc1]

At room temperature, to the intermediate 3-chloro-1-(1-(phenylsulfonyl)indolin-5-yl)propan-1-one (260 g, 743.21 mmol) in DMF (750 mL), sodium nitrite (102.6 g, 1.49 mol) and benzenetriol (30.9 g, 245.26 mmol) were added in portions. After 24 hours, the reaction was filtered to obtain a solid, which was then added into 700 mL deionized water and stirred for 2 hr. The filtered solid was dried to give the intermediate 3-nitro-1-(1-(phenylsulfonyl)indolin-5-yl)propan-1-one (258 g, 96% yield). ¹H NMR (400 MHz, DMSO) δ 7.93-7.89 (m, 3H), 7.81 (s, 1H), 7.72 (t, J=7.4 Hz, 1H), 7.65-7.57 (m, 3H), 4.89-4.78 (m, 2H), 4.01 (t, J=8.6 Hz, 2H), 3.63 (t, J=5.6 Hz, 2H), 3.06 (t, J=8.5 Hz, 2H).

1.4 Synthesis of 3-nitro-1-(1-(phenylsulfonyl)indolin-5-yl)propan-1-ol

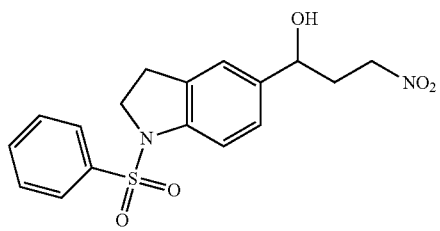 [SMILES: O=[N+]([O-])CCC(O)c1ccc2c(c1)CCN2S(=O)(=O)c1ccccc1]

The intermediate 3-nitro-1-(1-(phenylsulfonyl)indolin-5-yl)propan-1-one (250 g, 693.70 mmol) was dispersed in THF (750 mL)/H₂O (750 mL). In an ice bath, sodium borohydride (31.5 g, 832.44 mmol) was added portionwise to the reaction mixture with stirring. After verified by TLC that the reaction was completed, the reaction was quenched by slowly adding saturated ammonium chloride solution under stirring in an ice-bath. The reaction mixture was extracted twice with dichloromethane (750 mL), and the obtained organic layers were combined and washed once with brine, dried over anhydrous sodium sulfate, and concentrated under reduced pressure to give a viscous liquid 3-nitro-1-(1-(phenylsulfonyl)indolin-5-yl)propan-1-ol (231 g, 92% yield). ¹H NMR (400 MHz, DMSO) δ 7.84-7.78 (m, 2H), 7.68 (t, J=7.4 Hz, 1H), 7.57 (t, J=7.7 Hz, 2H), 7.44 (d, J=8.3 Hz, 1H), 7.16 (d, J=8.3 Hz, 1H), 7.13 (s, 1H), 5.48 (d, J=4.4 Hz, 1H), 4.63-4.49 (m, 3H), 3.92 (t, J=8.4 Hz, 2H), 2.89 (t, J=8.4 Hz, 2H), 2.23-2.06 (m, 2H). LRMS [M−H]⁻: 361.1.

1.5 Synthesis of trans-5-(2-nitrocyclopropyl)-1-(phenylsulfonyl)indoline

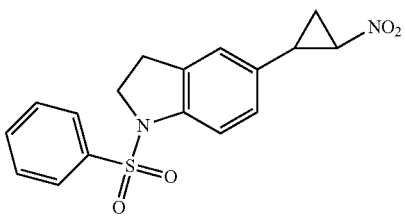 [SMILES: O=[N+]([O-])C1CC1c1ccc2c(c1)CCN2S(=O)(=O)c1ccccc1]

Triphenylphosphine (17.37 g, 66.23 mmol) was dissolved in 200 mL of anhydrous tetrahydrofuran under argon protection. Under an ice-bath, a solution of DBAD (15.25 g, 66.23 mmol) in tetrahydrofuran (100 mL) was added to the reaction mixture dropwise, and the mixture was stirred for 1 hour to precipitate white solids. A solution of 3-nitro-1-(1-(phenylsulfonyl)indolin-5-yl)propan-1-ol (16 g, 44.15 mmol) in tetrahydrofuran (100 mL) was slowly added to this mixture, and warmed slowly to room temperature for 3 hours. After verified by TLC that the reaction was completed, 300 mL of deionized water was added and extracted three times with ethyl acetate (200 mL). The obtained organic layers were combined and washed once with saturated brine, dried over anhydrous sodium sulfate and concentrated under reduced pressure. The obtained crude product was separated by column chromatography (EA/PE=1/6-1/3) and purified by recrystallization from isopropyl alcohol to provide white solids trans-5-(2-nitrocyclopropyl)-1-(phenylsulfonyl)indoline (7.3 g, 48%). ¹H NMR (400 MHz, DMSO) δ 7.80 (dd, J=8.4, 1.2 Hz, 2H), 7.71-7.65 (m, 1H), 7.57 (t, J=7.7 Hz, 2H), 7.39 (d, J=8.3 Hz, 1H), 7.11 (dd, J=8.4, 1.6 Hz, 1H), 7.04 (s, 1H), 4.70 (ddd, J=7.1, 3.8, 3.1 Hz, 1H), 3.90 (t, J=8.4 Hz, 2H), 3.07 (ddd, J=10.9, 8.0, 2.9 Hz, 1H), 2.87 (t, J=8.4 Hz, 2H), 2.14-2.06 (m, 1H), 1.76 (ddd, J=7.9, 7.3, 6.3 Hz, 1H). LRMS [M+H]⁺: 345.1.

1.6 Synthesis of trans-2-(1-(phenylsulfonyl)indolin-5-yl)cyclopropylamine (A1)

To a solution of trans-5-(2-nitrocyclopropyl)-1-(phenylsulfonyl)indoline (1.0 g, 2.90 mmol) in THF (30 mL), zinc powder (1.9 g, 29.04 mmol) was added. In an ice-bath, 2M aqueous hydrochloric acid (15 mL) was slowly added dropwise to the reaction liquid, slowly warmed to room temperature and stirred overnight. After verified by TLC that the reaction was completed, the mixture was filtered to obtain the filtrate, and the residue was washed with dichloromethane. The filtrate was neutralized with 1M aqueous sodium hydroxide solution (30 mL) to participate white solids. The filtrate was obtaine again, and the residue was washed with dichloromethane. Saturated sodium hydrogencarbonate solution was added into the filtrate and the mixture was extracted three times with dichloromethane (80 mL). The combined organic layer was washed once with saturated brine, dried over anhydrous sodium sulfate and concentrated under reduced pressure, and purified by column chromatography (MeOH/DCM=1/50-1/20) to provide a liquid. The resulting product was dissolved in 10 mL of dioxane solution. At room temperature, dihydrogen chloride solution was slowly added dropwise to the reaction solution with stirring, and the solution became turbid. After stirred overnight, a solid was precipitated from the reaction mixture, and then filtered to provide a yellow solid A1 (670 mg, 66% yield). $^1$H NMR (400 MHz, DMSO) δ 8.60 (s, 2H), 7.81-7.76 (m, 2H), 7.67 (t, J=7.4 Hz, 1H), 7.56 (t, J=7.7 Hz, 2H), 7.38 (d, J=8.3 Hz, 1H), 7.01 (d, J=8.3 Hz, 1H), 6.92 (s, 1H), 3.89 (t, J=8.4 Hz, 2H), 3.56 (s, 1H), 2.84 (t, J=8.4 Hz, 2H), 2.68 (dt, J=7.9, 4.1 Hz, 1H), 2.32-2.24 (m, 1H), 1.39-1.31 (m, 1H), 1.10 (dd, J=13.9, 6.3 Hz, 1H). mp 190-193° C. LRMS [M+H]$^+$: 315.1.

Example 2 trans-N-phenyl-2-(1-(phenylsulfonyl) indolin-5-yl)cyclopropylamine (A2)

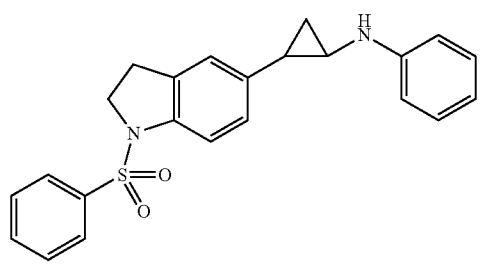 [SMILES: O=S(=O)(c1ccccc1)N1CCc2cc(C3CC3Nc3ccccc3)ccc21]

A1 (200 mg, 0.57 mmol) was dissolved in dichloromethane (20 mL), and 1 M aqueous sodium hydroxide solution (20 mL) was added for neutralization. The resulting liquid was extracted three times with dichloromethane (20 mL), and the combined organic layer was washed once with saturated brine. The resulting organic solution was dried over anhydrous sodium sulfate, and concentrated under reduced pressure to provide a pale yellow liquid. The liquid was re-dissolved into 4 mL of dimethyl sulfoxide, and iodobenzene (175 mg, 0.86 mmol), cuprous iodide (11 mg, 0.057 mmol) and L-valine (13 mg, 0.114 mmol) were added successively. The resulting reaction solution was heated and stirred in a 90° C. oil bath overnight under argon atmosphere. After verified by TLC that the reaction was completed, ethyl acetate was added for dilution, and washed three times with deionized water. The obtained organic layer was washed with saturated brine, dried over anhydrous sodium sulfate and concentrated under reduced pressure, and purified by column chromatography (MeOH/DCM=1/50-1/20) to provide a viscous liquid. The obtained product was dissolved in 10 mL of methanol, a solution of dioxane hydrochloride (5 mL) was slowly added dropwise, and the mixture was stirred overnight. After verified by TLC that the reaction was completed, ethyl acetate (20 mL) was added and concentrated under reduced pressure to provide a yellow solid A2 (131 mg, 54%). $^1$H NMR (500 MHz, Deuterium Oxide) δ 7.75 (dd, J=7.4, 2.1 Hz, 2H), 7.66-7.60 (m, 1H), 7.56 (t, J=7.4 Hz, 2H), 7.09-7.00 (m, 3H), 6.92 (dd, J=7.5, 2.0 Hz, 1H), 6.71 (tt, J=7.4, 1.9 Hz, 1H), 6.64-6.55 (m, 3H), 4.70 (s, 1H), 4.55 (dt, J=12.5, 8.5 Hz, 1H), 4.18 (ddd, J=12.4, 9.1, 2.3 Hz, 1H), 3.07 (ddd, J=18.9, 8.8, 2.3 Hz, 1H), 2.94 (ddd, J=18.6, 9.1, 8.1 Hz, 1H), 2.83 (q, J=7.1 Hz, 1H), 2.02 (q, J=7.0 Hz, 1H), 1.08 (td, J=7.0, 5.0 Hz, 1H), 0.78 (td, J=7.1, 5.0 Hz, 1H). LRMS [M+H]$^+$: 391.1.

Example 3 trans-N-benzyl-2-(1-(phenylsulfonyl) indolin-5-yl)cyclopropylamine (A3)

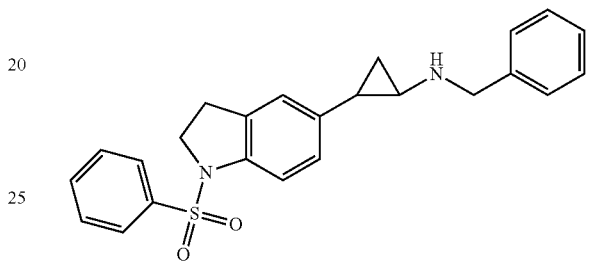

A1 (200 mg, 0.57 mmol) was dissolved in dichloromethane (20 mL), and 1 M aqueous sodium hydroxide solution (20 mL) was added for neutralization. The resulting liquid was extracted three times with dichloromethane (20 mL), and the combined organic layer was washed once with saturated brine. The resulting organic solution was dried over anhydrous sodium sulfate, and concentrated under reduced pressure to provide a pale yellow liquid. The liquid was re-dissolved in 10 mL of methanol, and benzaldehyde (41 mg, 0.38 mmol) and glacial acetic acid (44 μL, 0.76 mmol) were added successively. The resulting reaction solution was stirred under reflux for 10 minutes under argon protection. After the reaction solution was cooled to room temperature, sodium cyanoborohydride (45 mg, 0.76 mmol) was slowly added. After stirred to react for 24 hrs, saturated sodium hydrogencarbonate solution was added slowly to quench the reaction, and the mixture was extracted three times with dichloromethane (20 mL). The combined organic layer was washed successively with 10% aqueous acetic acid solution (20 mL), 1 M aqueous sodium hydroxide solution (20 mL) and saturated brine, dried over anhydrous sodium sulfate and concentrated under reduced pressure, and purified by column chromatography (MeOH/DCM=1/50-1/20) to provide a viscous liquid. The obtained product was dissolved in 10 mL of methanol, a solution of dioxane hydrochloride (5 mL) was slowly added dropwise, and the mixture was stirred overnight. After verified by TLC that the reaction was completed, ethyl acetate (20 mL) was added and concentrated under reduced pressure to provide a yellow solid A3 (137 mg, 55%). $^1$H NMR (400 MHz, MeOD) δ 7.79 (d, J=7.5 Hz, 2H), 7.63 (t, J=7.5 Hz, 1H), 7.53-7.41 (m, 8H), 6.96 (d, J=7.8 Hz, 1H), 6.85 (s, 1H), 4.35 (d, J=2.4 Hz, 2H), 3.93 (t, J=8.4 Hz, 2H), 2.93-2.87 (m, 1H), 2.84 (t, J=8.4 Hz, 2H), 2.33 (ddd, J=9.7, 6.5, 3.2 Hz, 1H), 0.91-0.88 (m, 2H). mp 92-94° C. LRMS [M+H]$^+$: 405.0.

Example 4 trans-N-(1-phenylethyl)-2-(1-(phenylsulfonyl)indolin-5-yl)cyclopropylamine (A4)

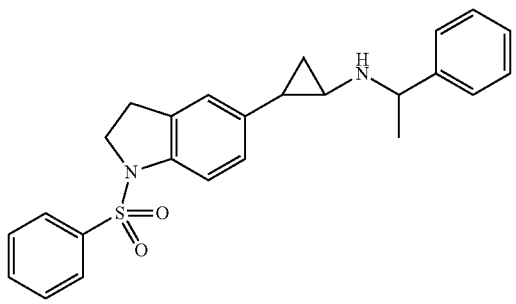 [SMILES: CC(NC1CC1c1ccc2c(c1)CCN2S(=O)(=O)c1ccccc1)c1ccccc1]

The benzaldehyde was replaced with acetophenone, while the remaining raw materials, reagents and preparation methods were the same as those in Example 3 to obtain the product A4, yield 42%. $^1$H NMR (500 MHz, Deuterium Oxide) δ 7.81 (dd, J=7.4, 2.0 Hz, 4H), 7.62 (ddt, J=9.5, 6.6, 2.2 Hz, 2H), 7.58-7.52 (m, 4H), 7.39-7.26 (m, 8H), 7.22 (ddt, J=7.5, 6.0, 2.1 Hz, 2H), 7.06-6.98 (m, 4H), 6.58 (d, J=7.4 Hz, 2H), 4.70 (s, 2H), 4.49 (ddd, J=12.6, 8.6, 2.0 Hz, 2H), 4.17 (q, J=6.9 Hz, 2H), 4.14-4.04 (m, 2H), 3.06 (dt, J=18.8, 8.9 Hz, 2H), 3.01-2.93 (m, 3H), 2.92 (d, J=7.0 Hz, 1H), 2.01 (q, J=7.1 Hz, 2H), 1.51 (d, J=6.8 Hz, 6H), 1.04 (td, J=7.0, 5.0 Hz, 2H), 0.84 (td, J=7.0, 4.9 Hz, 2H). LRMS [M+H]$^+$: 419.2.

Example 5 trans-N-(4-dimethylamino-benzyl)-2-(1-(phenylsulfonyl)indolin-5-yl)cyclopropylamine (A5)

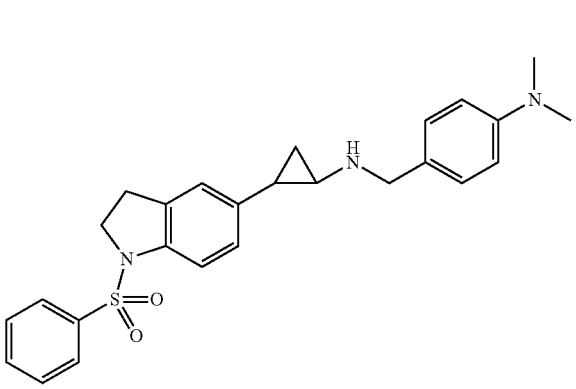 [SMILES: CN(C)c1ccc(CNC2CC2c2ccc3c(c2)CCN3S(=O)(=O)c2ccccc2)cc1]

The benzaldehyde was replaced with 4-N,N-dimethylbenzaldehyde, while the remaining raw materials, reagents and preparation methods were the same as those in Example 3 to obtain the product A5, yield 41%. $^1$H NMR (400 MHz, MeOD) δ7.81 (d, J=7.6 Hz, 2H), 7.70-7.63 (m, 3H), 7.58-7.49 (m, 5H), 6.99 (d, J=8.8 Hz, 1H), 6.91 (s, 1H), 4.43 (d, J=2.4 Hz, 2H), 3.95 (t, J=8.5 Hz, 2H), 3.25 (d, J=1.8 Hz, 6H), 2.97-2.91 (m, 1H), 2.86 (t, J=8.4 Hz, 2H), 2.44-2.37 (m, 1H), 1.52-1.45 (m, 1H), 1.38-1.34 (m, 1H). mp 145-147° C. LRMS [M+H]$^+$: 448.1.

Example 6 trans-N-(4-pyridine-methylene)-2-(1-(phenylsulfonyl)indolin-5-yl)cyclopropylamine (A6)

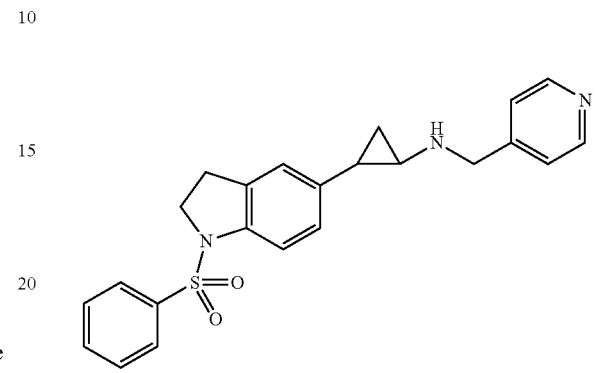

The benzaldehyde was replaced with 4-pyridinecarboxaldehyde, while the remaining raw materials, reagents and preparation methods were the same as those in Example 3 to obtain the product A6, yield 52%. $^1$H NMR (400 MHz, MeOD) δ 8.98-8.92 (m, 2H), 8.23 (d, J=6.3 Hz, 2H), 7.79 (d, J=7.5 Hz, 2H), 7.63 (t, J=7.5 Hz, 1H), 7.51 (dd, J=13.0, 5.3 Hz, 3H), 7.02 (d, J=8.1 Hz, 1H), 6.94 (s, 1H), 4.75 (s, 2H), 3.93 (t, J=8.4 Hz, 2H), 3.07 (dt, J=7.8, 3.8 Hz, 1H), 2.85 (t, J=8.4 Hz, 2H), 2.56 (ddd, J=10.4, 6.5, 3.7 Hz, 1H), 1.66-1.58 (m, 1H), 1.42-1.35 (m, 1H). mp 80-81° C. LRMS [M+H]$^+$: 406.1.

Example 7 trans-N-(5-indolylmethylene)-2-(1-(phenylsulfonyl)indolin-5-yl)cyclopropylamine (A7)

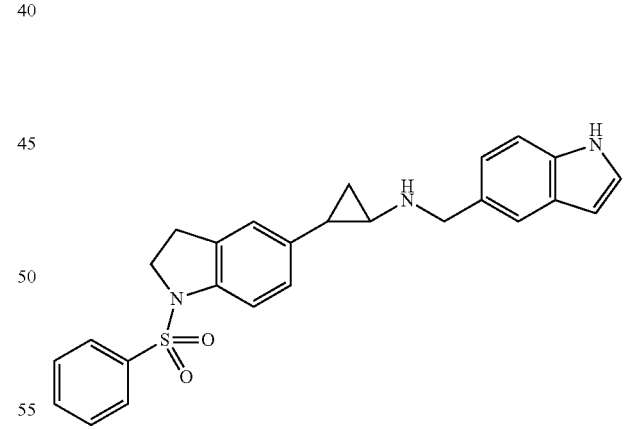

The benzaldehyde was replaced with 5-indoleformaldehyde, while the remaining raw materials, reagents and preparation methods were the same as those in Example 3 to obtain the product A7, yield 57%. $^1$H NMR (400 MHz, DMSO) δ 9.64 (s, 1H), 9.50 (s, 1H), 7.78 (t, J=6.8 Hz, 2H), 7.71-7.64 (m, 2H), 7.60-7.52 (m, 3H), 7.39 (dd, J=5.4, 2.7 Hz, 1H), 7.35 (d, J=8.2 Hz, 1H), 7.21 (d, J=8.3 Hz, 1H), 7.09 (d, J=6.5 Hz, 1H), 6.94 (d, J=8.2 Hz, 1H), 6.81 (s, 1H), 4.28 (s, 2H), 3.89 (t, J=8.4 Hz, 2H), 2.81 (t, 2H), 2.76 (d, J=5.4 Hz, 1H), 2.40-2.33 (m, 1H), 1.47-1.41 (m, 1H), 1.22-1.15 (m, 1H). mp>300° C. LRMS [M+H]$^+$: 444.2.

Example 8 trans-N-(3-indolylmethylene)-2-(1-(phenylsulfonyl)indolin-5-yl)cyclopropylamine (A8)

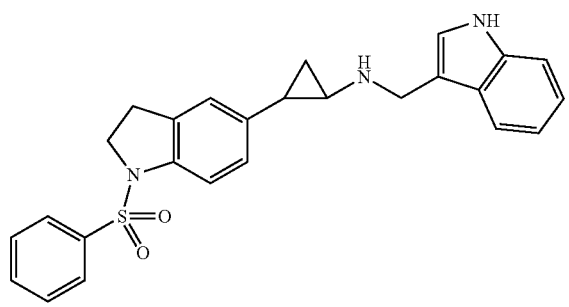 [SMILES: O=S(=O)(c1ccccc1)N1CCc2cc(C3CC3NCc3c[nH]c4ccccc34)ccc21]

The benzaldehyde was replaced with 3-indoleformaldehyde, while the remaining raw materials, reagents and preparation methods were the same as those in Example 3 to obtain the product A8, yield 48%. $^1$H NMR (400 MHz, MeOD) δ 7.81 (d, J=7.6 Hz, 2H), 7.64 (d, J=7.6 Hz, 1H), 7.61 (d, J=7.8 Hz, 1H), 7.55-7.48 (m, 3H), 7.46 (s, 1H), 7.42 (d, J=8.2 Hz, 1H), 7.15 (t, J=7.6 Hz, 1H), 6.98 (t, J=7.6 Hz, 1H), 6.92 (d, J=8.0 Hz, 1H), 6.74 (s, 1H), 4.58 (s, 2H), 3.94 (t, J=8.4 Hz, 2H), 2.91 (dt, J=8.1, 4.1 Hz, 1H), 2.83 (t, J=8.4 Hz, 2H), 2.31 (ddd, J=10.2, 6.8, 3.4 Hz, 1H), 1.48-1.33 (m, 2H). mp 123-124° C. LRMS [M+H]$^+$: 443.8.

Example 9 trans-N-(2-(1-(phenylsulfonyl)indolin-5-yl)cyclopropyl)cyclohexylamine (A9)

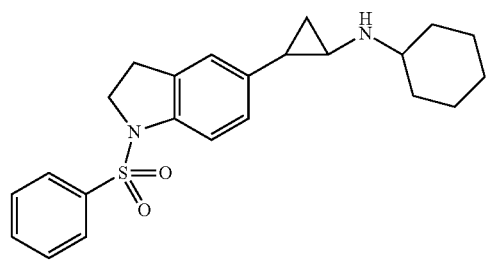 [SMILES: O=S(=O)(c1ccccc1)N1CCc2cc(C3CC3NC3CCCCC3)ccc21]

The benzaldehyde was replaced with cyclohexanone, while the remaining raw materials, reagents and preparation methods were the same as those in Example 3 to obtain the product A9, yield 48%. $^1$H NMR (500 MHz, Deuterium Oxide) δ 7.81 (dd, J=7.5, 2.0 Hz, 2H), 7.66-7.52 (m, 3H), 7.01-6.93 (m, 2H), 6.58 (d, J=7.5 Hz, 1H), 4.49 (ddd, J=12.5, 6.0, 4.5 Hz, 1H), 4.02 (dt, J=12.6, 8.7 Hz, 1H), 3.02-2.95 (m, 2H), 2.79 (q, J=7.0 Hz, 1H), 2.35 (p, J=6.9 Hz, 1H), 2.10 (dq, J=12.7, 7.0 Hz, 2H), 1.98 (q, J=7.1 Hz, 1H), 1.74 (dt, J=12.7, 7.0 Hz, 2H), 1.60 (ddd, J=12.7, 7.0, 5.7 Hz, 2H), 1.42 (dq, J=12.6, 6.9 Hz, 2H), 1.30 (dq, J=12.7, 6.9 Hz, 2H), 1.02 (td, J=7.0, 5.0 Hz, 1H), 0.81 (td, J=7.0, 5.0 Hz, 1H). LRMS [M+H]$^+$: 397.2.

Example trans-N-cyclohexylmethylene-2-(1-(phenylsulfonyl)indolin-5-yl)cyclopropylamine (A10)

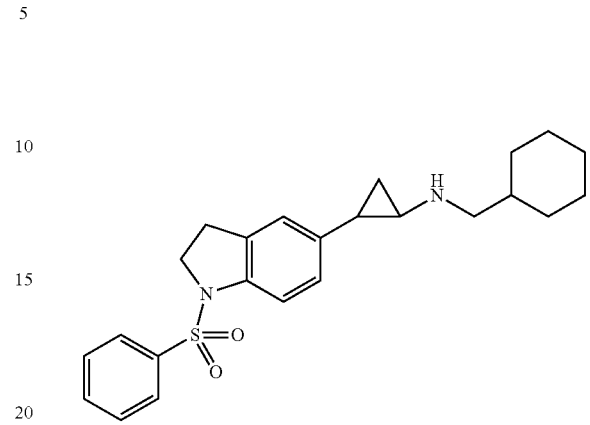

The benzaldehyde was replaced with cyclohexane formaldehyde, while the remaining raw materials, reagents and preparation methods were the same as those in Example 3 to obtain the product A10, yield 43%. $^1$H NMR (400 MHz, MeOD) δ 7.78 (d, J=7.5 Hz, 2H), 7.62 (t, J=7.4 Hz, 1H), 7.54-7.46 (m, 3H), 7.04 (d, J=8.4 Hz, 1H), 6.94 (s, 1H), 3.93 (t, J=8.4 Hz, 2H), 3.02 (d, J=7.2 Hz, 2H), 2.92-2.81 (m, 3H), 2.40 (ddd, J=10.4, 6.7, 3.6 Hz, 1H), 1.80 (d, J=11.8 Hz, 4H), 1.75-1.67 (m, 2H), 1.48-1.40 (m, 1H), 1.35-1.20 (m, 4H), 1.11-0.98 (m, 2H). mp 140-145° C. LRMS [M+H]$^+$: 411.1.

Example 11 trans-N-butyl-2-(1-(phenylsulfonyl)indolin-5-yl)cyclopropylamine (A11)

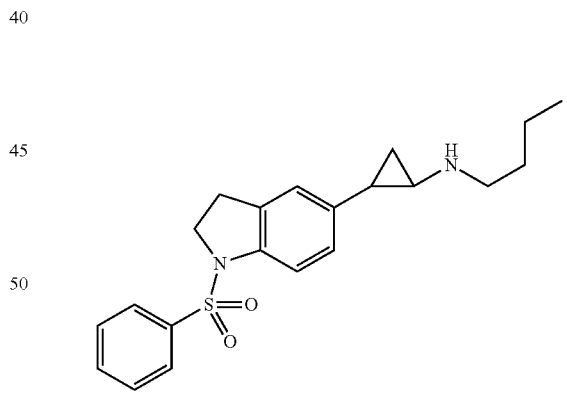

The benzaldehyde was replaced with butyraldehyde, while the remaining raw materials, reagents and preparation methods were the same as those in Example 3 to obtain the product A11, yield 39%. $^1$H NMR (500 MHz, Deuterium Oxide) δ 7.81 (dd, J=7.4, 2.0 Hz, 2H), 7.66-7.58 (m, 1H), 7.57 (d, J=7.3 Hz, 2H), 6.98 (s, 2H), 6.61-6.55 (m, 1H), 4.70 (s, 1H), 4.49 (ddd, J=12.6, 6.3, 4.3 Hz, 1H), 4.02 (dt, J=12.4, 8.8 Hz, 1H), 3.03-2.91 (m, 3H), 2.89 (ddd, J=12.4, 9.6, 2.5 Hz, 1H), 2.76 (q, J=7.0 Hz, 1H), 1.98 (q, J=7.1 Hz, 1H), 1.58-1.42 (m, 2H), 1.37-1.17 (m, 2H), 1.07-0.94 (m, 4H), 0.80 (td, J=7.0, 5.0 Hz, 1H). LRMS [M+H]$^+$: 371.2.

Example 12 trans-2-(1-(phenylsulfonyl)indolin-5-yl)-N-((tetrahydro-2H-pyran-4-yl)methyl)cyclopropylamine (A12)

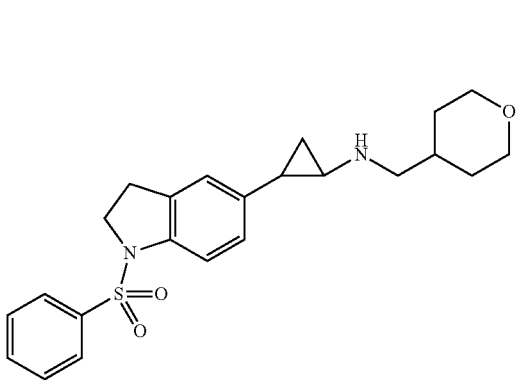 [SMILES: O=S(=O)(c1ccccc1)N1CCc2cc(C3CC3NCC3CCOCC3)ccc21]

The benzaldehyde was replaced with 4-tetrahydropyran-aldehyde, while the remaining raw materials, reagents and preparation methods were the same as those in Example 3 to obtain the product A12, yield 53%. $^1$H NMR (500 MHz, Deuterium Oxide) δ 7.81 (dd, J=7.4, 2.1 Hz, 2H), 7.66-7.52 (m, 3H), 6.97 (d, J=6.7 Hz, 2H), 6.61-6.55 (m, 1H), 4.70 (s, 1H), 4.49 (ddd, J=12.5, 6.1, 4.2 Hz, 1H), 4.03 (dt, J=12.6, 8.8 Hz, 1H), 3.87 (dt, J=11.5, 7.0 Hz, 2H), 3.47 (dt, J=11.5, 6.9 Hz, 2H), 3.02-2.95 (m, 2H), 2.78 (q, J=7.1 Hz, 1H), 2.47 (d, J=6.7 Hz, 2H), 1.98 (q, J=7.1 Hz, 1H), 1.70-1.53 (m, 3H), 1.25 (dq, J=13.3, 6.8 Hz, 2H), 1.01 (td, J=6.9, 5.0 Hz, 1H), 0.82 (td, J=7.0, 5.0 Hz, 1H). LRMS [M+H]$^+$: 413.2.

Example 13 trans-N-(2-(1-(phenylsulfonyl)indolin-5-yl)cyclopropyl)tetrahydro-2H-pyran-4-amine (A13)

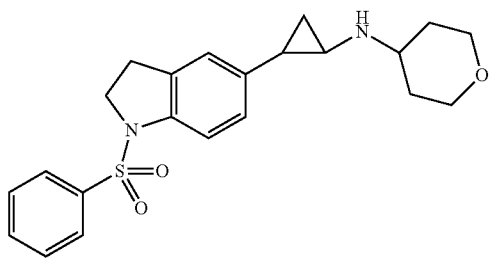 [SMILES: O=S(=O)(c1ccccc1)N1CCc2cc(C3CC3NC3CCOCC3)ccc21]

The benzaldehyde was replaced with 4-tetrahydropyrone, while the remaining raw materials, reagents and preparation methods were the same as those in Example 3 to obtain the product A13, yield 48%. $^1$H NMR (500 MHz, Deuterium Oxide) δ 7.80 (dd, J=7.4, 2.1 Hz, 2H), 7.66-7.52 (m, 3H), 7.03-6.95 (m, 2H), 6.58 (d, J=7.4 Hz, 1H), 4.70 (s, 1H), 4.53 (ddd, J=12.6, 9.0, 7.6 Hz, 1H), 4.12 (ddd, J=12.3, 9.2, 2.8 Hz, 1H), 3.88 (dt, J=11.5, 7.0 Hz, 2H), 3.49 (dt, J=11.4, 7.1 Hz, 2H), 3.07-2.79 (m, 4H), 2.08 (dq, J=14.0, 7.1 Hz, 2H), 1.98 (q, J=7.0 Hz, 1H), 1.67 (dq, J=14.0, 7.1 Hz, 2H), 1.02 (td, J=7.0, 5.0 Hz, 1H), 0.80 (td, J=7.0, 4.9 Hz, 1H). LRMS [M+H]$^+$: 399.2.

Example 14 trans-N-(4-piperidinylmethylene)-2-(1-(phenylsulfonyl)indolin-5-yl)cyclopropylamine (A14)

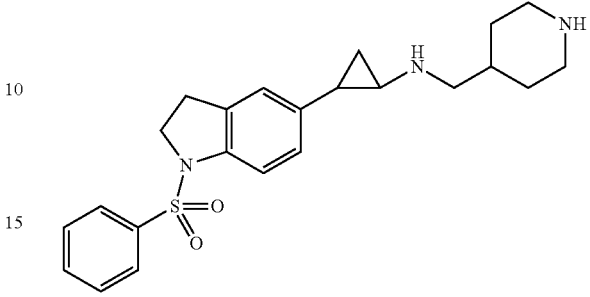

A27 (100 mg, 0.195 mmol) was dissolved in methanol (5 mL), and a solution of dioxane hydrochloride (2 mL) was added under stirring at room temperature. After the reaction was stirred overnight, 10 mL of ethyl acetate was added and concentrated under increased pressure to give the salt product A14 (78 mg, 83%). $^1$H NMR (400 MHz, MeOD) δ 7.80 (d, J=7.5 Hz, 2H), 7.64 (t, J=7.6 Hz, 1H), 7.55-7.48 (m, 3H), 7.08 (d, J=8.2 Hz, 1H), 6.99 (s, 1H), 3.94 (t, J=8.4 Hz, 2H), 3.46 (d, J=12.7 Hz, 2H), 3.19 (d, J=6.9 Hz, 2H), 3.06 (t, J=11.8 Hz, 2H), 2.97 (dt, J=7.8, 4.0 Hz, 1H), 2.87 (t, J=8.4 Hz, 2H), 2.55 (ddd, J=10.3, 6.7, 3.7 Hz, 1H), 2.21-2.14 (m, 1H), 2.08 (d, J=12.7 Hz, 2H), 1.64-1.50 (m, 3H), 1.39-1.30 (m, 1H). mp 179-181° C. LRMS [M+H]$^+$: 412.1

Example 15 trans-N-(4-piperidinyl)-2-(1-(phenylsulfonyl)indolin-5-yl)cyclopropylamine (A15)

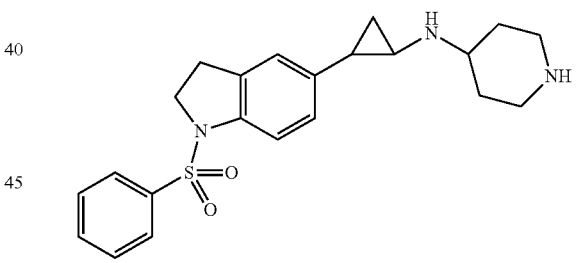

A1 (200 mg, 0.57 mmol) was dissolved in dichloromethane (20 mL), and 1 M aqueous sodium hydroxide solution (20 mL) was added for neutralization. The resulting liquid was extracted three times with dichloromethane (20 mL), and the combined organic layer was washed once with saturated brine. The resulting organic solution was dried over anhydrous sodium sulfate, and concentrated under reduced pressure to provide a pale yellow liquid. The liquid was re-dissolved in 10 mL of dichloroethane, and N-tert-butoxycarbonyl-4-piperidone (76 mg, 0.38 mmol) and glacial acetic acid (44 μL, 0.76 mmol) were added successively. Sodium triacetoxyborohydride (161 mg, 0.76 mmol) was slowly added under argon protection. After stirred at room temperature overnight, saturated sodium hydrogencarbonate solution was added slowly to quench the reaction, and the mixture was extracted three times with dichloromethane (20 mL). The combined organic layer was washed successively with 10% aqueous acetic acid solution (20 mL), 1 M aqueous sodium hydroxide solution (20 mL) and saturated brine, dried over anhydrous sodium sulfate and concentrated under reduced pressure, and purified by column chromatography (MeOH/DCM=1/50-1/20) to provide a viscous liquid. The obtained product was dissolved in 10 mL of methanol, a solution of dioxane hydrochloride (5 mL) was slowly added dropwise, and the mixture was stirred overnight. After verified by TLC that the reaction was completed, ethyl acetate (20 mL) was added and concentrated under reduced pressure to provide a yellow solid A15 (81 mg, 45%). $^1$H NMR (400 MHz, MeOD) δ 7.81 (d, J=7.7 Hz, 2H), 7.64 (t, J=7.5 Hz, 1H), 7.56-7.49 (m, 3H), 7.06 (d, J=8.1 Hz, 1H), 6.97 (s, 1H), 3.95 (t, J=8.4 Hz, 2H), 3.23-3.13 (m, 1H), 2.94 (dt, J=7.7, 3.9 Hz, 1H), 2.87 (t, J=8.4 Hz, 2H), 2.44 (ddd, J=10.2, 6.6, 3.7 Hz, 1H), 2.38-2.28 (m, 2H), 2.19 (d, J=11.5 Hz, 2H), 1.66-1.46 (m, 5H), 1.38 (dd, J=14.3, 7.0 Hz, 1H). mp>300° C. LRMS [M+H]$^+$: 412.2.

Example 16 trans-N-(4-piperidinylethyl)-2-(1-(phenylsulfonyl)indolin-5-yl)cyclopropylamine (A16)

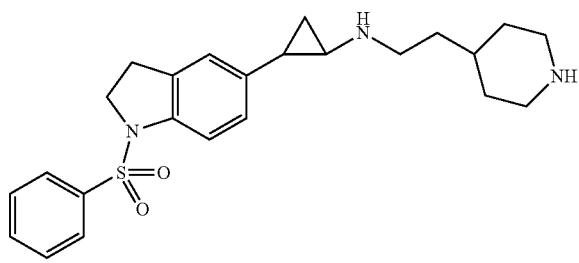 [SMILES: O=S(=O)(c1ccccc1)N1CCc2cc(C3CC3NCCC3CCNCC3)ccc21]

N-tert-butoxycarbonylpiperidine-4-carbaldehyde was replaced by 4-tert-butoxycarbonylpiperidine acetaldehyde, while the remaining raw materials, reagents and preparation methods were the same as those in Example 14 to obtain the product A16, yield 57%. $^1$H NMR (400 MHz, MeOD) δ 7.82-7.78 (m, 2H), 7.64 (t, J=7.2 Hz, 1H), 7.56-7.48 (m, 3H), 7.07 (d, J=8.3 Hz, 1H), 6.98 (s, 1H), 3.94 (t, J=8.4 Hz, 2H), 3.42 (d, J 32 12.7 Hz, 3H), 3.29-3.21 (m, 2H), 3.01 (t, J=11.9 Hz, 2H), 2.97-2.90 (m, 1H), 2.87 (t, J=8.4 Hz, 2H), 2.48 (ddd, J=10.2, 6.6, 3.4 Hz, 1H), 2.00 (d, J=10.1 Hz, 2H), 1.90-1.61 (m, 2H), 1.53-1.38 (m, 3H), 1.35 (dd, J=14.1, 7.2 Hz, 1H). mp 64-65° C. LRMS [M+H]$^+$: 426.2.

Example 17 trans-N-(azetidin-3-ylmethyl)-2-(1-(phenylsulfonyl)indolin-5-yl)cyclopropylamine (A17)

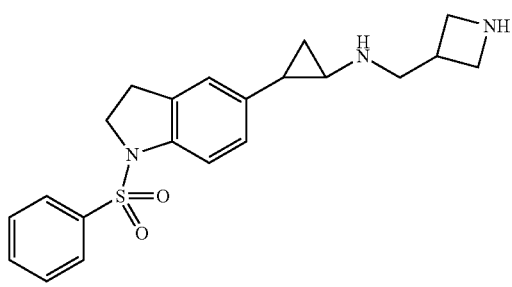 [SMILES: O=S(=O)(c1ccccc1)N1CCc2cc(C3CC3NCC3CNC3)ccc21]

N-tert-butoxycarbonylpiperidine-4-carbaldehyde was replaced by 3-tert-butoxycarbonyl acridinium formaldehyde, while the remaining raw materials, reagents and preparation methods were the same as those in Example 14 to obtain the product A17, yield 48%. $^1$H NMR (400 MHz, MeOD) δ 7.83-7.77 (m, 2H), 7.64 (t, J=7.4 Hz, 1H), 7.53 (dt, J=13.0, 6.7 Hz, 3H), 7.11-7.05 (m, 1H), 7.00 (d, J=6.6 Hz, 1H), 4.26-4.04 (m, 1H), 3.97-3.91 (m, 3H), 3.43 (d, J=5.2 Hz, 2H), 3.24 (t, J=5.9 Hz, 1H), 3.02 (dt, J=25.5, 12.8 Hz, 1H), 2.86 (t, J=8.3 Hz, 2H), 2.77 (s, 1H), 2.69-2.50 (m, 1H), 1.68-1.57 (m, 1H), 1.41-1.26 (m, 2H). mp 145-148° C. LRMS [M+H]$^+$: 384.2.

Example 18 trans-4-((2-(1-(phenylsulfonyl)indolin-5-yl)cyclopropylamino)methyl)cyclohexylamine (A18)

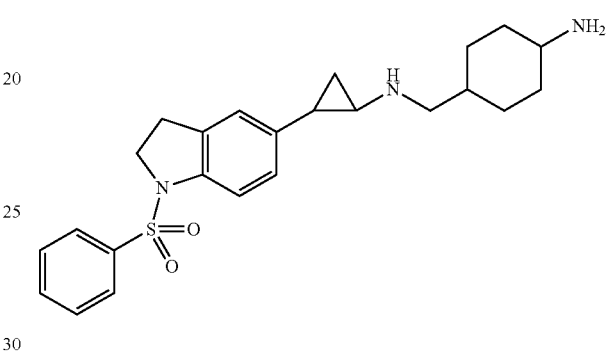

N-tert-butoxycarbonylpiperidine-4-carbaldehyde was replaced by 1-tert-butoxycarbonylcyclohexylamine-4-carbaldehyde, while the remaining raw materials, reagents and preparation methods were the same as those in Example 14 to obtain the product A18, yield 42%. $^1$H NMR (400 MHz, MeOD) δ 7.80 (d, J=7.8 Hz, 2H), 7.64 (t, J=7.4 Hz, 1H), 7.57-7.48 (m, 3H), 7.07 (d, J=8.2 Hz, 1H), 6.98 (s, 1H), 3.94 (t, J=8.4 Hz, 2H), 3.10 (d, J=7.0 Hz, 2H), 2.94 (dt, J=7.7, 3.9 Hz, 1H), 2.86 (t, J=8.3 Hz, 2H), 2.52 (ddd, J=10.2, 6.5, 3.6 Hz, 1H), 2.12 (d, J=9.9 Hz, 2H), 2.00 (d, J=11.7 Hz, 2H), 1.89-1.75 (m, 2H), 1.59-1.40 (m, 3H), 1.36-1.18 (m, 3H). mp 172-175° C. LRMS [M+H]$^+$: 426.2.

Example 19 trans-N1-(2-(1-(phenylsulfonyl)indolin-5-yl)cyclopropyl)cyclohexane-1,4-diamine (A19)

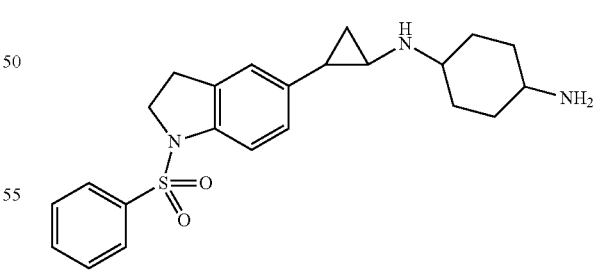

A1 (200 mg, 0.57 mmol) was dissolved in dichloromethane (20 mL), and 1 M aqueous sodium hydroxide solution (20 mL) was added for neutralization. The resulting liquid was extracted three times with dichloromethane (20 mL), and the combined organic layer was washed once with saturated brine. The resulting organic solution was dried over anhydrous sodium sulfate, and concentrated under reduced pressure to provide a pale yellow liquid. This liquid was redissolved in 10 mL of methanol, and 4-N-Boc-aminocyclohexanone (81 mg, 0.38 mmol) and 200 mg of molecular sieves were added to the solution, and the reaction was stirred for 10 minutes. Glacial acetic acid (44 µL, 0.76 mmol) was added under ice-cooling, and the mixture was slowly warmed to room temperature for 3 hours. Thereafter, the reaction solution was placed under −30° C. for cooling, sodium borohydride (18 mg, 0.45 mmol) was added portionwise, and the mixture was slowly returned to room temperature for 3 hours. Saturated sodium hydrogencarbonate solution was added slowly to quench the reaction, and the mixture was extracted three times with dichloromethane (20 mL). The combined organic layer was washed successively with 10% aqueous acetic acid solution (20 mL), 1 M aqueous sodium hydroxide solution (20 mL) and saturated brine, dried over anhydrous sodium sulfate and concentrated under reduced pressure, and purified by column chromatography (MeOH/DCM=1/50-1/20) to provide a viscous liquid. The obtained product was dissolved in 10 mL of methanol, a solution of dioxane hydrochloride (5 mL) was slowly added dropwise, and the mixture was stirred overnight. After verified by TLC that the reaction was completed, ethyl acetate (20 mL) was added and concentrated under reduced pressure to provide a yellow solid A19 (63 mg, 34%). $^1$H NMR (400 MHz, MeOD) δ 7.81 (d, J=7.5 Hz, 2H), 7.64 (t, J=7.3 Hz, 1H), 7.56-7.49 (m, 3H), 7.06 (d, J=8.2 Hz, 1H), 6.97 (s, 1H), 3.95 (t, J=8.3 Hz, 2H), 3.22-3.14 (m, 1H), 2.98-2.91 (m, 1H), 2.87 (t, J=8.3 Hz, 2H), 2.48-2.41 (m, 1H), 2.39-2.28 (m, 2H), 2.19 (d, J=11.1 Hz, 2H), 1.68-1.47 (m, 5H), 1.45-1.32 (m, 2H). mp>300° C. LRMS [M+H]$^+$: 412.2.

Example 20 trans-N-(2-(1-(phenylsulfonyl)indolin-5-yl)cyclopropyl)-7-azaspiro[3.5]nonane-2-amine (A20)

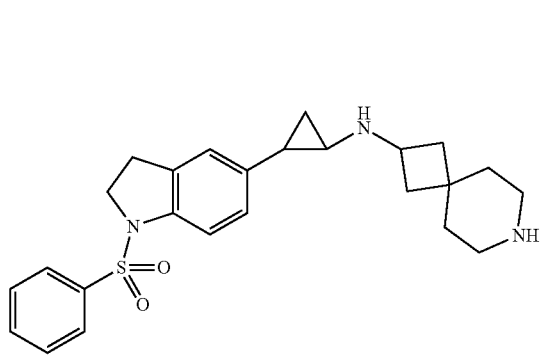 [SMILES: O=S(=O)(c1ccccc1)N1CCc2cc(C3CC3NC3CC4(CCNCC4)C3)ccc21]

N-tert-butoxycarbonylpiperidin-4-one was replaced with tert-butyl 2-oxo-7-azaspiro[3.5]nonane-7-carboxylate, while the remaining raw materials, reagents and preparation methods were the same as those in Example 15 to obtain the product A20, yield 40%. $^1$H NMR (400 MHz, CD$_3$OD) δ 7.77 (dd, J=8.3, 1.1 Hz, 2H), 7.61 (t, J=7.5 Hz, 1H), 7.52-7.45 (m, 3H), 7.03 (d, J=8.3 Hz, 1H), 6.95 (s, 1H), 4.04-3.95 (m, 1H), 3.91 (t, J=8.4 Hz, 2H), 3.19-3.14 (m, 2H), 3.13-3.08 (m, 2H), 2.84 (t, J=8.4 Hz, 2H), 2.81-2.77 (m, 1H), 2.50-2.37 (m, 3H), 2.18 (td, J=12.5, 8.6 Hz, 2H), 1.94-1.87 (m, 4H), 1.48 (ddd, J=10.8, 6.7, 4.4 Hz, 1H), 1.32-1.26 (m, 1H). mp 161-164° C. LRMS [M+H]$^+$: 438.2.

Example 21 trans-N-((4-methylpiperidin-4-yl)methyl)-2-(1-(phenylsulfonyl)indolin-5-yl)cyclopropylamine A21)

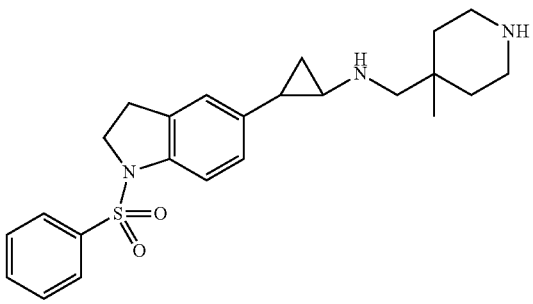 [SMILES: CC1(CNC2CC2c2ccc3c(c2)CCN3S(=O)(=O)c2ccccc2)CCNCC1]

N-tert-butoxycarbonylpiperidine-4-carbaldehyde was replaced by 4-methyl-N-tert-butoxycarbonylpiperidine-4-carbaldehyde, while the remaining raw materials, reagents and preparation methods were the same as those in Example 14 to obtain the product A21, yield 56%. $^1$H NMR (400 MHz, MeOD) δ 7.80 (d, J=7.5 Hz, 2H), 7.64 (t, J=7.4 Hz, 1H), 7.56-7.49 (m, 3H), 7.09 (d, J=8.4 Hz, 1H), 7.01 (s, 1H), 3.95 (t, J=8.4 Hz, 2H), 3.30 (d, J=5.0 Hz, 1H), 3.27 (s, 2H), 3.26-3.19 (m, 2H), 3.03 (dt, J=7.6, 3.9 Hz, 1H), 2.87 (t, J=8.3 Hz, 2H), 2.68-2.58 (m, 1H), 1.91-1.81 (m, 2H), 1.77 (dt, J=9.4, 4.4 Hz, 2H), 1.67-1.59 (m, 1H), 1.35 (dd, J=14.1, 7.0 Hz, 1H), 1.32-1.20 (m, 4H). mp 137-138° C. LRMS [M+H]$^+$: 426.3.

Example 22 trans-4-((2-(1-(phenylsulfonyl)indolin-5-yl)cyclopropylamino)methyl)piperidine-4-carboxylic acid (A22)

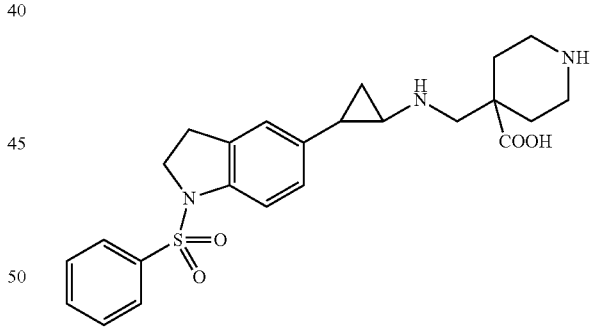

N-tert-butoxycarbonylpiperidine-4-carbaldehyde was replaced by 4-carboxylic acid-N-tert-butoxycarbonylpiperidine-4-carbaldehyde, while the remaining raw materials, reagents and preparation methods were the same as those in Example 14 to obtain the product A22, yield 51%. $^1$H NMR (500 MHz, Deuterium Oxide) δ 7.84-7.77 (m, 2H), 7.66-7.52 (m, 3H), 7.02-6.94 (m, 2H), 6.58 (d, J=7.5 Hz, 1H), 4.70 (s, 2H), 4.54-4.45 (m, 1H), 4.02 (dt, J=12.5, 8.7 Hz, 1H), 3.15 (dt, J=12.4, 6.9 Hz, 2H), 3.01-2.94 (m, 2H), 2.92-2.75 (m, 3H), 2.70 (s, 2H), 2.36 (dt, J=13.2, 7.2 Hz, 2H), 1.94 (q, J=7.0 Hz, 1H), 1.77 (dt, J=13.3, 7.1 Hz, 2H), 1.03 (td, J=7.0, 5.0 Hz, 1H), 0.80 (td, J=6.9, 5.0 Hz, 1H). LRMS [M+H]$^+$: 456.2.

Example 23 trans-N-((1-methylpiperidin-4-yl)methyl)-2-(1-(phenylsulfonyl)indolin-5-yl)cyclopropylamine (A23)

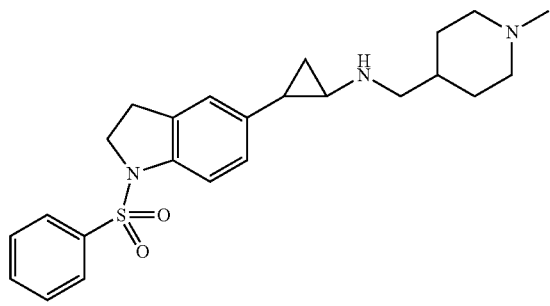 [SMILES: CN1CCC(CNC2CC2c2ccc3c(c2)CCN3S(=O)(=O)c2ccccc2)CC1]

N-tert-butoxycarbonylpiperidine-4-carbaldehyde was replaced by
N-methylpiperidine-4-carbaldehyde, while the remaining raw materials, reagents and preparation methods were the same as those in Example 14 to obtain the product A23, yield 56%. $^1$H NMR (500 MHz, Deuterium Oxide) δ 7.81 (dd, J=7.5, 2.0 Hz, 2H), 7.66-7.52 (m, 3H), 6.97 (d, J=6.6 Hz, 2H), 6.58 (dt, J=7.5, 1.1 Hz, 1H), 4.70 (s, 1H), 4.49 (ddd, J=12.5, 6.0, 4.5 Hz, 1H), 4.02 (dt, J=12.5, 8.7 Hz, 1H), 3.11 (dt, J=12.5, 7.1 Hz, 2H), 3.02-2.95 (m, 2H), 2.78 (q, J=7.0 Hz, 1H), 2.47 (d, J=7.0 Hz, 2H), 2.31-2.22 (m, 2H), 2.25 (s, 4H), 1.97 (q, J=6.9 Hz, 1H), 1.73 (dq, J=14.1, 7.1 Hz, 2H), 1.42 (dq, J=13.9, 7.1 Hz, 2H), 1.23 (hept, J=7.0 Hz, 1H), 1.01 (td, J=7.0, 5.0 Hz, 1H), 0.82 (td, J=7.1, 5.0 Hz, 1H). LRMS [M+H]$^+$: 426.2.

Example 24 trans-N-((1-benzylpiperidin-4-yl)methyl)-2-(1-(phenylsulfonyl)indolin-5-yl)cyclopropylamine (A24)

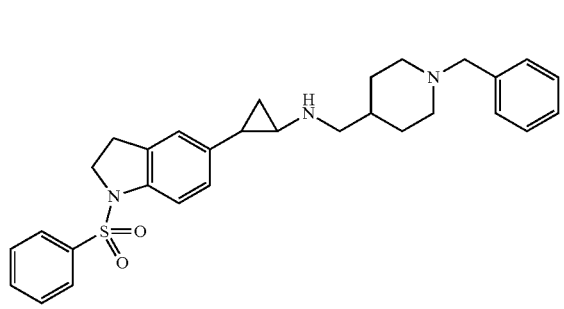 [SMILES: O=S(=O)(c1ccccc1)N1CCc2cc(C3CC3NCC3CCN(Cc4ccccc4)CC3)ccc21]

The preparation was carried out by the same manner as in Example 14 to give the product A24, yield 37%. $^1$H NMR (400 MHz, MeOD) δ 7.80 (d, J=7.5 Hz, 2H), 7.64 (t, J=7.4 Hz, 1H), 7.60-7.56 (m, 2H), 7.55-7.49 (m, 6H), 7.07 (d, J=8.3 Hz, 1H), 6.98 (s, 1H), 4.35 (s, 2H), 3.94 (t, J=8.4 Hz, 2H), 3.55 (d, J=12.6 Hz, 2H), 3.17 (d, J=6.8 Hz, 2H), 3.10 (t, J=11.9 Hz, 2H), 2.96 (dt, J=7.8, 4.0 Hz, 1H), 2.86 (t, J=8.4 Hz, 2H), 2.53 (ddd, J=10.1, 6.5, 3.6 Hz, 1H), 2.11 (d, J=14.4 Hz, 2H), 1.65 (dd, J=26.3, 12.8 Hz, 2H), 1.59-1.52 (m, 1H), 1.34 (dd, J=14.1, 7.1 Hz, 1H). mp 181-183° C. LRMS [M+H]$^+$: 502.3.

Example 25 Trans-tert-butyl 4-((4-(2-(1-(phenylsulfonyl))indolin-5-yl)cyclopropylamino)methyl)piperidin-1-yl)methyl) benzoate (A25)

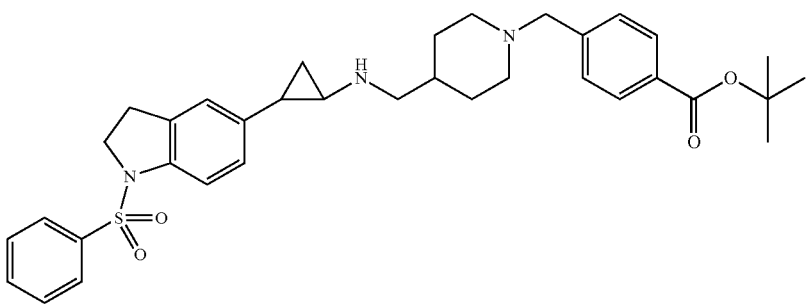 [SMILES: CC(C)(C)OC(=O)c1ccc(CN2CCC(CNC3CC3c3ccc4c(c3)CCN4S(=O)(=O)c3ccccc3)CC2)cc1]

The preparation was carried out by the same manner as in Example 14 to give the product A25, yield 48%. $^1$H NMR (400 MHz, MeOD) δ 7.93 (d, J=8.0 Hz, 2H), 7.77 (d, J=7.4 Hz, 2H), 7.62 (t, J=7.4 Hz, 1H), 7.52-7.46 (m, 3H), 7.44 (d, J=8.1 Hz, 2H), 6.93 (d, J=8.1 Hz, 1H), 6.81 (s, 1H), 3.91 (t, J=8.3 Hz, 2H), 3.59 (s, 2H), 2.91 (d, J=12.2 Hz, 2H), 2.78 (t, J=8.3 Hz, 2H), 2.58 (d, J=6.8 Hz, 2H), 2.26-2.19 (m, 1H), 2.04 (t, J=11.9 Hz, 2H), 1.85 (ddd, J=9.4, 6.2, 3.1 Hz, 1H), 1.81-1.70 (m, 2H), 1.61 (s, 9H), 1.56-1.49 (m, 1H), 1.31-1.23 (m, 2H), 1.03 (dt, J=9.5, 4.7 Hz, 1H), 0.95 (dd, J=12.6, 5.6 Hz, 1H). mp 62-65° C. LRMS [M+H]$^+$: 602.2.

Example 26 Trans-4-((4-(2-(1-(phenylsulfonyl))indolin-5-yl)cyclopropylamino)methyl)piperidin-1-yl) methyl)benzoic acid (A26)

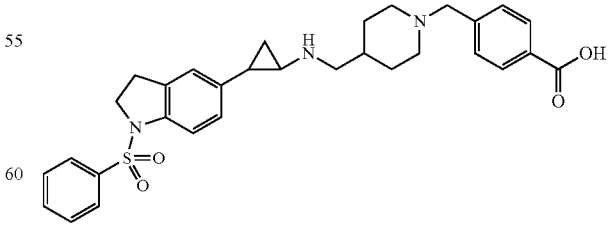

A25 (80 mg, 0.132 mmol) was dispersed in 1 M hydrochloric acid (5 mL), and the reaction liquid was heated for 2 hours under 90° C. The supernatant was poured out when it is hot, and 10 mL of acetonitrile was added and concentrated under reduced pressure to give the salt-formed product A26 (63 mg, 70%). ¹H NMR (400 MHz, CD₃OD) δ 8.15-8.08 (m, 3H), 7.77 (d, J=7.0 Hz, 2H), 7.70 (s, 2H), 7.61 (t, J=7.2 Hz, 1H), 7.51-7.47 (m, 2H), 7.04 (d, J=7.4 Hz, 1H), 6.96 (s, 1H), 4.41 (s, 2H), 3.91 (t, J=7.3 Hz, 2H), 3.53 (s, 2H), 3.15 (s, 4H), 2.90 (s, 1H), 2.83 (t, J=8.1 Hz, 1H), 2.52 (s, 1H), 2.13-2.01 (m, 2H), 1.66 (s, 3H), 1.54 (s, 1H), 1.32 (s, 1H). mp 190-192° C. LRMS [M+H]⁺: 546.2

Example 27 Trans-tert-butyl 4-((2-(1-(phenylsulfonyl)indolin-5-yl)cyclopropylamino)methyl)piperidine-1-carboxylate (A27)

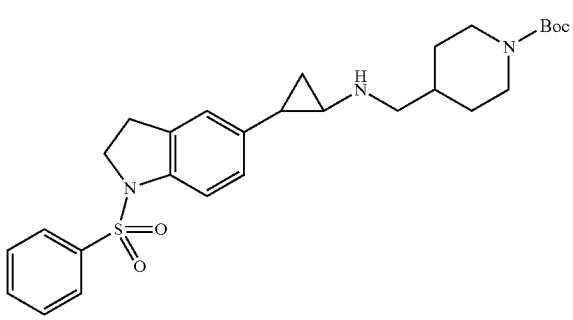 [SMILES: CC(C)(C)OC(=O)N1CCC(CNC2CC2c2ccc3c(c2)CCN3S(=O)(=O)c2ccccc2)CC1]

A1 (200 mg, 0.57 mmol) was dispersed in dichloromethane (20 mL), and 1 M aqueous sodium hydroxide solution (20 mL) was added for neutralization. The resulting liquid was extracted three times with dichloromethane (20 mL), and the combined organic layer was washed once with saturated brine. The resulting organic solution was dried over anhydrous sodium sulfate, and concentrated under reduced pressure to provide a pale yellow liquid. The liquid was re-dissolved in 10 mL of methanol, and 1-tert-butoxycarbonylpiperidine-4-carbaldehyde (81 mg, 0.38 mmol) and glacial acetic acid (44 µL, 0.76 mmol) were added successively. The resulting reaction solution was stirred under reflux for 10 minutes under argon protection. After the reaction solution was cooled to room temperature, sodium cyanoborohydride (45 mg, 0.76 mmol) was slowly added. After stirred for 24 hrs, saturated sodium hydrogencarbonate solution was added slowly to quench the reaction, and the mixture was extracted three times with dichloromethane (20 mL). The combined organic layer was washed successively with 10% aqueous acetic acid solution (20 mL), 1 M aqueous sodium hydroxide solution (20 mL) and saturated brine, dried over anhydrous sodium sulfate and concentrated under reduced pressure, and purified by column chromatography (MeOH/DCM=1/50-1/20) to provide a viscous liquid, A22 (83 mg, 43% yield). ¹H NMR (400 MHz, CDCl₃) δ 7.77 (d, J=7.5 Hz, 2H), 7.53 (dd, J=14.8, 7.8 Hz, 2H), 7.44 (d, J=7.9 Hz, 2H), 6.86 (d, J=8.5 Hz, 1H), 6.74 (s, 1H), 4.09 (s, 2H), 3.89 (t, J=8.4 Hz, 2H), 2.81 (t, J=8.4 Hz, 2H), 2.73-2.62 (m, 2H), 2.59 (d, J=6.7 Hz, 2H), 2.27-2.20 (m, 1H), 1.79 (ddd, J=9.0, 5.7, 2.9 Hz, 1H), 1.65 (s, 2H), 1.61-1.54 (m, 1H), 1.45 (s, 9H), 1.08 (qd, J=12.5, 4.5 Hz, 2H), 1.00 (dt, J=9.3, 4.7 Hz, 1H), 0.87 (dd, J=12.3, 5.7 Hz, 1H). mp 60-61° C. LRMS [M+Na]⁺: 534.1.

Example 28 Trans-benzyl 4-((2-(1-(phenylsulfonyl)indolin-5-yl)cyclopropylamino)methyl)piperidine-1-carboxylate (A28)

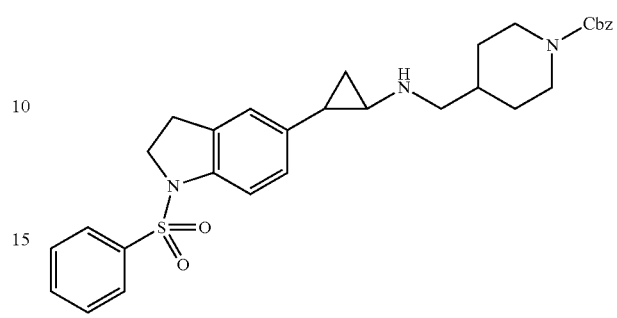

The preparation was carried out in the same manner as in Example 14 to give the product A28, and the compound A28 was prepared in a similar manner to the compound A3, yield 46%. ¹H NMR (400 MHz, MeOD) δ 7.80 (d, J=7.4 Hz, 2H), 7.63 (t, J=7.5 Hz, 1H), 7.56-7.48 (m, 3H), 7.39-7.30 (m, 5H), 7.06 (d, J=8.5 Hz, 1H), 6.96 (s, 1H), 5.13 (s, 2H), 4.21 (d, J=12.8 Hz, 2H), 3.94 (t, J=8.4 Hz, 2H), 3.11 (d, J=7.0 Hz, 2H), 2.97-2.81 (m, 5H), 2.43 (s, 1H), 1.80 (d, J=12.2 Hz, 2H), 1.53-1.44 (m, 1H), 1.37-1.17 (m, 4H). mp 90-92° C. LRMS [M+H]⁺: 546.0.

Example 29 Trans-tert-butyl 4-(2-(1-(phenylsulfonyl)indolin-5-yl)cyclopropylcarbamoyl)piperidine-1-carboxylate (A29)

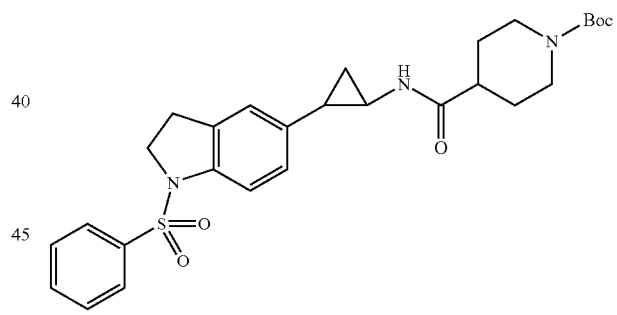

A1 (100 mg, 0.29 mmol), 1-tert-butoxycarbonyl-4-piperidinecarboxylic acid (98 mg, 0.43 mmol) and HATU (163 mg, 0.43 mmol) were dispersed in 8 mL of dichloromethane. Triethylamine (120 µL, 0.86 mmol) was added to the reaction liquid, which was stirred at room temperature overnight. After verified by TLC that the reaction was completed, the reaction liquid was diluted with methylene chloride (20 mL), and washed successively with 10% aqueous acetic acid, deionized water, saturated sodium hydrogen carbonate and brine, and dried over anhydrous sodium sulfate. The organic phase was concentrated under reduced pressure and purified by column chromatography (EA/PE=1/2-1/1) to provide a white solid A29 (93 mg, 62%). ¹H NMR (400 MHz, CDCl₃) δ 7.75 (d, J=7.6 Hz, 2H), 7.56-7.50 (m, 2H), 7.42 (t, J=7.7 Hz, 2H), 6.97 (d, J=8.5 Hz, 1H), 6.94 (s, 1H), 4.11 (s, 2H), 3.88 (t, J=8.4 Hz, 2H), 2.81 (t, J=8.4 Hz, 2H), 2.78-2.65 (m, 3H), 2.18 (ddd, J=15.0, 7.6, 3.6 Hz, 1H), 1.94 (ddd, J=9.5, 6.3, 3.3 Hz, 1H), 1.77 (d, J=12.7 Hz, 2H), 1.69

(s, 1H), 1.61 (ddd, J=16.5, 12.5, 4.4 Hz, 2H), 1.44 (s, 9H), 1.15 (dd, J=13.4, 6.4 Hz, 1H), 1.11-1.03 (m, 1H). mp 146-148° C. LRMS [M+Na]+: 548.2.

Example 30 Trans-2-(1-(phenylsulfonyl)indolin-5-yl)-N-(1-(piperidin-4-yl)ethyl)cyclopropylamine (A30)

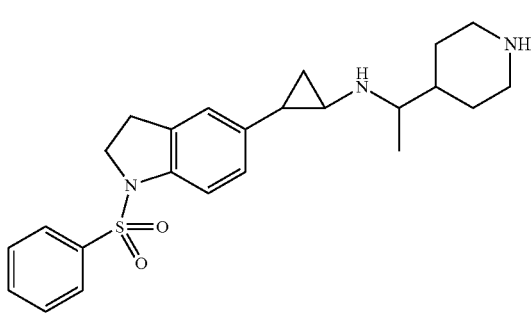 [SMILES: CC(NC1CC1c1ccc2c(c1)CCN2S(=O)(=O)c1ccccc1)C1CCNCC1]

The preparation was carried out by the same manner as in Example 14 to give the product A30, yield 41%. $^1$H NMR (500 MHz, Deuterium Oxide) δ 7.84-7.78 (m, 2H), 7.66-7.52 (m, 3H), 6.98 (d, J=6.6 Hz, 2H), 6.58 (dt, J=7.5, 1.1 Hz, 1H), 4.70 (s, 2H), 4.49 (ddd, J=12.5, 6.1, 4.3 Hz, 1H), 4.02 (dt, J=12.4, 8.6 Hz, 1H), 3.14 (dt, J=12.5, 7.1 Hz, 2H), 3.02-2.95 (m, 2H), 2.85 (q, J=7.1 Hz, 1H), 2.73 (dt, J=12.5, 7.0 Hz, 2H), 2.59 (p, J=6.8 Hz, 1H), 2.00 (q, J=6.9 Hz, 1H), 1.72 (dq, J=11.8, 6.6, 6.1 Hz, 2H), 1.36-1.18 (m, 6H), 1.03 (td, J=7.0, 5.0 Hz, 1H), 0.81 (td, J=7.0, 5.0 Hz, 1H). LRMS [M+H]+: 426.2.

Example 31 Trans-2-(1-(phenylsulfonyl)indolin-5-yl)-N-(2-(piperidin-4-yl)propan-2-yl)cyclopropylamine (A31)

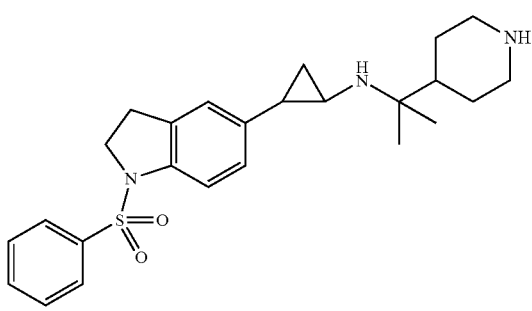 [SMILES: CC(C)(NC1CC1c1ccc2c(c1)CCN2S(=O)(=O)c1ccccc1)C1CCNCC1]

$^1$H NMR (500 MHz, Deuterium Oxide) δ 7.81 (dd, J=7.5, 2.0 Hz, 2H), 7.66-7.52 (m, 3H), 7.04 (dd, J=7.5, 2.0 Hz, 1H), 6.97 (d, J=2.0 Hz, 1H), 6.58 (d, J=7.5 Hz, 1H), 4.70 (s, 2H), 4.49 (ddd, J=12.7, 6.3, 4.3 Hz, 1H), 4.03 (dt, J=12.5, 8.7 Hz, 1H), 3.17-2.94 (m, 5H), 2.74 (dt, J=12.5, 7.1 Hz, 2H), 1.99 (q, J=7.1 Hz, 1H), 1.81-1.68 (m, 3H), 1.33-1.24 (m, 2H), 1.16 (s, 6H), 0.98 (td, J=7.0, 4.9 Hz, 1H), 0.82 (td, J=7.0, 5.0 Hz, 1H). LRMS [M+H]+: 440.2.

Example 32 Trans-2-(1-(biphenyl-4-ylsulfonyl)indolin-5-yl)-N-(piperidin-4-ylmethyl)cyclopropylamine (A32)

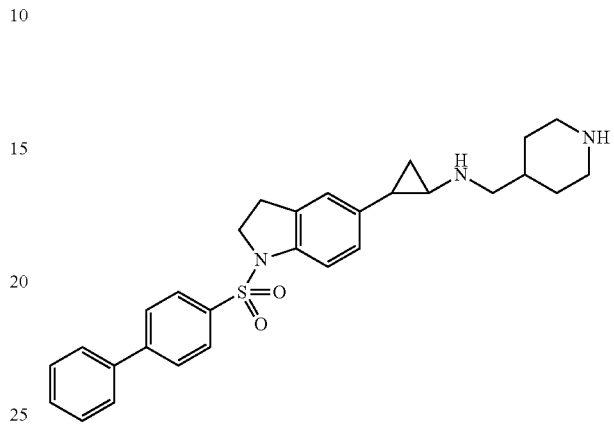

32.1 tert-butyl-trans-4-((tert-butoxycarbonyl(2-(1-(phenylsulfonyl)indolin-5-yl)cyclo-propyl)amino)methyl)piperidine-1-carboxylate

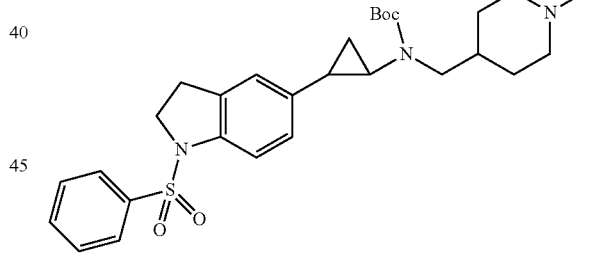

A27 (960 mg, 1.95 mmol) was dissolved in 30 mL of dichloromethane, and then Boc$_2$O (614 mg, 2.81 mmol) and triethylamine (390 μL, 2.81 mmol) were successively added, and the mixture was stirred at room temperature for eight hours. After verified by TLC that the reaction was completed, the reaction liquid was concentrated under reduced pressure and purified by column chromatography (EA/PE=1/8-1/4) to give a white solid tert-butyl-trans-4-((tert-butoxycarbonyl) (2-(1-(benzenesulfonyl)indolin-5-yl)cyclo-propyl)amino)methyl)piperidine-1-carboxylate (1.08 g, 94% yield). $^1$H NMR (400 MHz, CDCl$_3$) δ 7.78 (d, J=7.6 Hz, 2H), 7.59-7.53 (m, 2H), 7.44 (t, J=7.8 Hz, 2H), 6.97 (d, J=8.4 Hz, 1H), 6.83 (s, 1H), 4.17-4.01 (m, 2H), 3.91 (t, J=8.4 Hz, 2H), 3.29 (s, 1H), 3.02 (s, 1H), 2.84 (t, J=8.3 Hz, 2H), 2.74-2.56 (m, 3H), 2.03 (s, 1H), 1.82 (s, 1H), 1.62 (t, J=13.0 Hz, 2H), 1.46 (s, 9H), 1.41 (s, 9H), 1.23-1.08 (m, 4H). mp 68-70° C. LRMS [M+Na]+: 634.2.

32.2 tert-butyl-trans-4-((tert-butoxycarbonyl(2-(indolin-5-yl)cyclopropyl)amino)methyl)piperidine-1-carboxylate

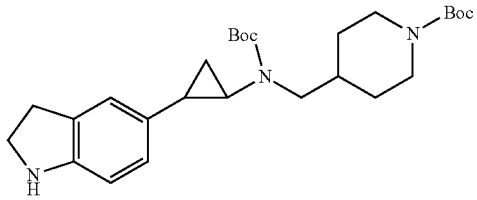 [SMILES: CC(C)(C)OC(=O)N1CCC(CN(C(=O)OC(C)(C)C)C2CC2c2ccc3c(c2)CCN3)CC1]

In an ice bath, magnesium powder (794 mg, 32.69 mmol) was added to the tert-butyl-trans-4-((tert-butoxycarbonyl(2-(1-(phenylsulfonyl)indolin-5-yl)cyclo-propyl)amino)methyl)piperidine-1-carboxylate (1.0 g, 1.63 mmol) in MeOH (50 mL) with stirring, and the reaction was slowly warmed to room temperature and stirred overnight. After verified by TLC that the reaction was completed, the reaction was quenched by slowly adding saturated ammonium chloride solution with stirring in an ice-bath. After the reaction mixture was extracted three times with dichloromethane (50 mL), the organic layer was combined and washed once successively with saturated aqueous sodium hydrogen carbonate and brine. The resulting organic solution was dried over anhydrous sodium sulfate, and concentrated under reduced pressure to give a pale red oil tert-butyl trans-4-((tert-butoxycarbonyl(2-(indolin-5-yl) cyclopropyl)amino)methyl)piperidine-1-carboxylate (741 mg, 96% yield). $^1$H NMR (400 MHz, CDCl$_3$) δ 6.86 (s, 1H), 6.77 (d, J=7.9 Hz, 1H), 6.51 (d, J=7.9 Hz, 1H), 4.17-3.96 (m, 2H), 3.48 (t, J=8.3 Hz, 2H), 3.22 (bs, 1H), 3.07 (bs, 1H), 2.94 (t, J=8.3 Hz, 2H), 2.64 (bs, 2H), 2.58-2.53 (m, 1H), 2.06-1.93 (m, 1H), 1.82 (bs, 1H), 1.59 (t, J=9.4 Hz, 2H), 1.43 (s, 9H), 1.41 (s, 9H), 1.18-1.06 (m, 4H). LRMS [M+H]$^+$: 472.2.

32.3 Synthesis of Trans-2-(1-(biphenyl-4-ylsulfonyl)indolin-5-yl)-N-(piperidin-4-ylmethyl)cyclopropylamine (A32)

At room temperature, biphenylsulfonyl chloride (121 mg, 0.48 mmol) and triethylamine (66 μL, 0.48 mmol) were added into tert-butyl trans-4-((tert-butoxycarbonyl(2-(indoline-5-yl)cyclopropyl)amino)methyl)piperidine-1-carboxylate (150 mg, 0.32 mmol) in dichloromethane (8 mL), and the reaction was stirred overnight. After verified by TLC that the reaction was completed, it was diluted with 20 mL of dichloromethane, and washed once successively with deionized water, saturated aqueous sodium hydrogen carbonate solution and saturated brine. The obtained organic solution was dried over anhydrous sodium sulfate and concentrated under reduced pressure, and then purified by column chromatography (EA/PE=1/8-1/4). The obtained solid was dissolved in 10 mL of methanol, a solution of dioxane hydrochloride (5 mL) was slowly added dropwise, and the mixture was stirred overnight. After verified by TLC that the reaction was completed, ethyl acetate (20 mL) was added and concentrated under reduced pressure to provide solid A32 (81 mg, 52%). $^1$H NMR (400 MHz, CD$_3$OD) δ 7.83 (d, J=8.4 Hz, 2H), 7.70 (d, J=8.4 Hz, 2H), 7.59 (d, J=7.1 Hz, 2H), 7.54 (d, J=8.3 Hz, 1H), 7.44 (t, J=7.3 Hz, 2H), 7.38 (t, J=7.2 Hz, 1H), 7.07 (d, J=8.3 Hz, 1H), 6.97 (s, 1H), 3.94 (t, J=8.4 Hz, 2H), 3.43 (d, J=12.8 Hz, 2H), 3.15 (d, J=6.9 Hz, 2H), 3.03 (t, J=12.1 Hz, 2H), 2.94 (dt, J=7.4, 3.7 Hz, 1H), 2.88 (t, J=8.4 Hz, 2H), 2.54 (ddd, J=10.0, 6.4, 3.3 Hz, 1H), 2.16 (d, J=2.9 Hz, 1H), 2.05 (d, J=13.8 Hz, 2H), 1.61-1.48 (m, 3H), 1.31 (dd, J=14.2, 7.0 Hz, 1H). mp 182-185° C. LRMS [M+H]$^+$: 488.2.

Example 33 Trans-2-(1-(naphthalen-2-ylsulfonyl)indolin-5-yl)-N-(piperidin-4-ylmethyl)cyclopropylamine (A33)

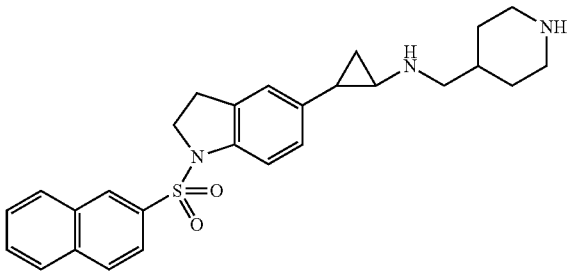 [SMILES: O=S(=O)(c1ccc2ccccc2c1)N1CCc2cc(C3CC3NCC3CCNCC3)ccc21]

The preparation was carried out by the same manner as in Example 32 to give the product A33, yield 41%. $^1$H NMR (400 MHz, CD$_3$OD) δ 8.40 (s, 1H), 7.98 (d, J=7.8 Hz, 1H), 7.95-7.89 (m, 2H), 7.70 (dd, J=8.7, 1.8 Hz, 1H), 7.68-7.56 (m, 3H), 7.07 (d, J=8.4 Hz, 1H), 6.92 (s, 1H), 3.99 (t, J=8.4 Hz, 2H), 3.42 (d, J=12.9 Hz, 2H), 3.14 (d, J=6.9 Hz, 2H), 3.02 (t, J=12.1 Hz, 2H), 2.92 (dt, J=7.6, 3.9 Hz, 1H), 2.82 (t, J=8.4 Hz, 2H), 2.51 (ddd, J=10.1, 6.5, 3.5 Hz, 1H), 2.19-2.08 (m, 1H), 2.04 (d, J=14.0 Hz, 2H), 1.60-1.45 (m, 3H), 1.30 (dd, J=13.1, 5.8 Hz, 1H). mp 162-164° C. LRMS [M+H]$^+$: 462.2.

Example 34 trans-N-(piperidin-4-ylmethyl)-2-(1-(4-(trifluoromethyl)benzenesulfonyl)indolin-5-yl)cyclopropylamine (A34)

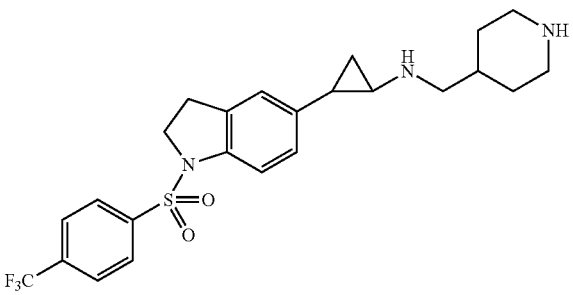 [SMILES: O=S(=O)(c1ccc(C(F)(F)F)cc1)N1CCc2cc(C3CC3NCC3CCNCC3)ccc21]

The preparation was carried out by the same manner as in Example 32 to give the product A34, yield 53%. $^1$H NMR (400 MHz, MeOD) δ 8.02 (d, J=8.2 Hz, 2H), 7.85 (d, J=8.3 Hz, 2H), 7.55 (d, J=8.3 Hz, 1H), 7.10 (d, J=8.4 Hz, 1H), 7.01 (s, 1H), 4.00 (t, J=8.4 Hz, 2H), 3.46 (d, J=13.1 Hz, 2H), 3.19 (d, J=7.0 Hz, 2H), 3.06 (td, J=12.9, 2.1 Hz, 2H), 2.98 (dt, J=7.8, 4.1 Hz, 1H), 2.91 (t, J=8.4 Hz, 2H), 2.55 (ddd, J=10.1, 6.6, 3.5 Hz, 1H), 2.22-2.12 (m, 1H), 2.08 (d, J=14.1 Hz, 2H), 1.65-1.51 (m, 3H), 1.36 (dd, J=14.3, 6.8 Hz, 1H). mp 217-221° C. LRMS [M+H]$^+$: 480.2.

Example 35 trans-N-(piperidin-4-ylmethyl)-2-(1-(3-(trifluoromethyl)benzenesulfonyl)indolin-5-yl)cyclopropylamine (A35)

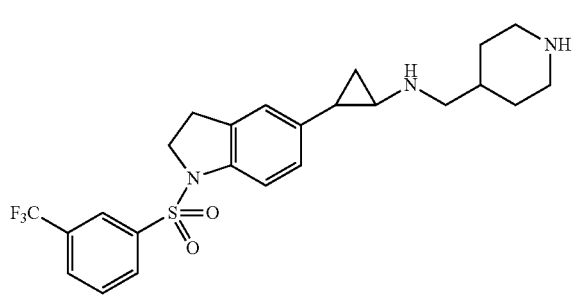 [SMILES: O=S(=O)(c1cccc(C(F)(F)F)c1)N1CCc2cc(C3CC3NCC3CCNCC3)ccc21]

The preparation was carried out by the same manner as in Example 32 to give the product A35, yield 47%. $^1$H NMR (400 MHz, MeOD) δ 8.09 (d, J=7.6 Hz, 1H), 7.99-7.95 (m, 2H), 7.76 (t, J=7.8 Hz, 1H), 7.56 (d, J=8.1 Hz, 1H), 7.12 (d, J=8.1 Hz, 1H), 7.01 (s, 1H), 3.98 (t, J=8.2 Hz, 2H), 3.46 (d, J=12.1 Hz, 2H), 3.19 (d, J=5.4 Hz, 2H), 3.06 (t, J=12.5 Hz, 2H), 2.98 (s, 1H), 2.86 (t, J=8.2 Hz, 2H), 2.61-2.54 (m, 1H), 2.18 (s, 1H), 2.08 (d, J=13.4 Hz, 2H), 1.58 (d, J=7.6 Hz, 3H), 1.38-1.29 (m, 1H). mp 200-203° C. LRMS [M+H]$^+$: 480.2.

Example 36 trans-N-(piperidin-4-ylmethyl)-2-(1-(2-(trifluoromethyl)benzenesulfonyl)indolin-5-yl)cyclopropylamine (A36)

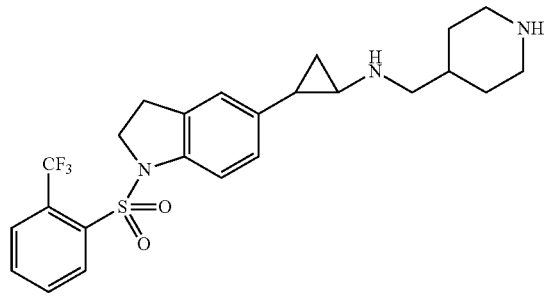 [SMILES: O=S(=O)(c1ccccc1C(F)(F)F)N1CCc2cc(C3CC3NCC3CCNCC3)ccc21]

The preparation was carried out by the same manner as in Example 32 to give the product A36, yield 38%. $^1$H NMR (500 MHz, Deuterium Oxide) δ 8.07-8.00 (m, 1H), 7.84-7.76 (m, 1H), 7.69-7.63 (m, 2H), 6.99 (d, J=2.0 Hz, 1H), 6.92 (dd, J=7.5, 2.0 Hz, 1H), 6.58 (d, J=7.5 Hz, 1H), 4.70 (s, 2H), 4.55 (ddd, J=12.5, 8.4, 1.6 Hz, 1H), 4.18 (ddd, J=12.4, 9.6, 7.9 Hz, 1H), 3.19-3.05 (m, 3H), 2.98 (ddd, J=18.7, 8.1, 1.7 Hz, 1H), 2.79-2.67 (m, 3H), 2.47 (d, J=6.9 Hz, 2H), 1.92 (q, J=7.0 Hz, 1H), 1.66 (dq, J=14.0, 7.0 Hz, 2H), 1.39-1.28 (m, 2H), 1.21 (hept, J=6.9 Hz, 1H), 1.02 (td, J=7.0, 5.0 Hz, 1H), 0.79 (td, J=7.1, 5.0 Hz, 1H). LRMS [M+H]$^+$: 480.2.

Example 37 trans-N-(piperidin-4-ylmethyl)-2-(1-(m-toluenesulfonyl)indolin-5-yl)cyclopropylamine (A37)

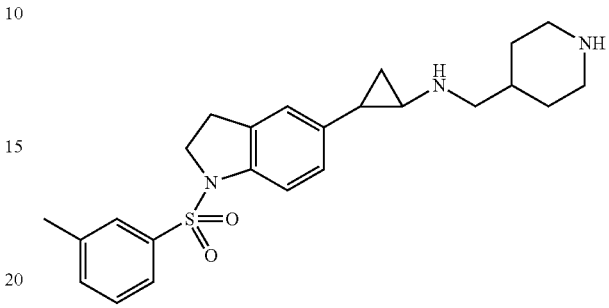

The preparation was carried out by the same manner as in Example 32 to give the product A37, yield 48%. $^1$H NMR (500 MHz, Deuterium Oxide) δ 7.78 (dt, J=7.3, 2.0 Hz, 1H), 7.71 (t, J=2.0 Hz, 1H), 7.61 (dt, J=7.5, 2.0 Hz, 1H), 7.54 (t, J=7.4 Hz, 1H), 7.00-6.94 (m, 2H), 6.58 (dt, J=7.3, 1.0 Hz, 1H), 4.70 (s, 2H), 4.49 (ddd, J=12.5, 6.1, 4.5 Hz, 1H), 4.02 (dt, J=12.5, 8.7 Hz, 1H), 3.14 (dt, J=12.5, 7.1 Hz, 2H), 3.02-2.95 (m, 2H), 2.82-2.69 (m, 3H), 2.47 (d, J=6.9 Hz, 2H), 2.42 (s, 3H), 1.97 (q, J=7.0 Hz, 1H), 1.69 (dq, J=13.8, 7.0 Hz, 2H), 1.39-1.18 (m, 3H), 1.01 (td, J=7.0, 5.0 Hz, 1H), 0.81 (td, J=7.1, 5.0 Hz, 1H). LRMS [M+H]$^+$: 426.2.

Example 38 trans-2-(1-(3-chlorobenzenesulfonyl)indolin-5-yl)-N-(piperidin-4-ylmethyl)cyclopropylamine (A38)

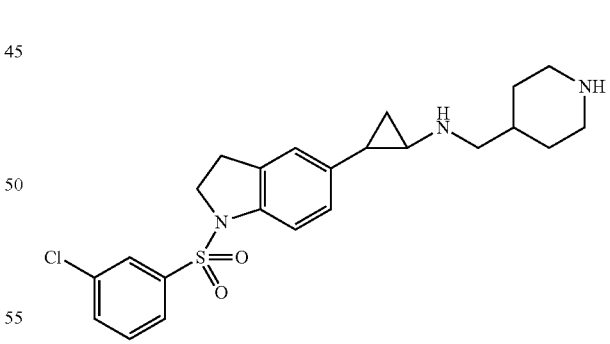

The preparation was carried out by the same manner as in Example 32 to give the product A38, yield 38%. $^1$H NMR (400 MHz, MeOD) δ 7.77 (t, J=1.8 Hz, 1H), 7.76-7.73 (m, 1H), 7.66 (ddd, J=8.0, 2.0, 0.9 Hz, 1H), 7.55-7.50 (m, 2H), 7.11 (d, J=8.4 Hz, 1H), 7.02 (s, 1H), 3.96 (t, J=8.4 Hz, 2H), 3.46 (d, J=13.1 Hz, 2H), 3.19 (d, J=6.9 Hz, 2H), 3.06 (t, J=11.8 Hz, 2H), 2.99 (dt, J=7.7, 4.0 Hz, 1H), 2.90 (t, J=8.4 Hz, 2H), 2.58 (ddd, J=10.0, 6.4, 3.3 Hz, 1H), 2.23-2.14 (m, 1H), 2.09 (d, J=14.9 Hz, 2H), 1.64-1.53 (m, 3H), 1.36 (dd, J=14.2, 6.9 Hz, 1H). mp 165-169° C. LRMS [M+H]$^+$: 446.2.

Example 39 trans-2-(1-(3-methoxybenzenesulfonyl)indolin-5-yl)-N-(piperidin-4-ylmethyl)cyclopropylamine (A39)

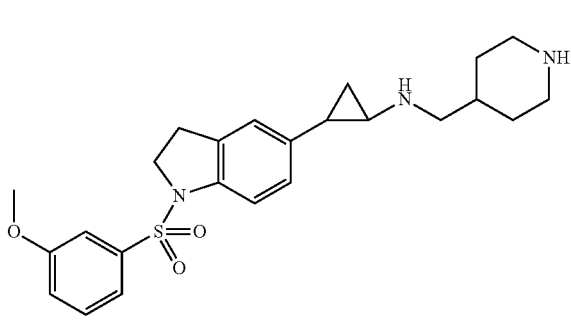 [SMILES: COc1cccc(S(=O)(=O)N2CCc3cc(C4CC4NCC4CCNCC4)ccc32)c1]

The preparation was carried out by the same manner as in Example 32 to give the product A39, yield 51%. $^1$H NMR (400 MHz, MeOD) δ 7.54 (d, J=8.0 Hz, 1H), 7.43 (t, J=7.9 Hz, 1H), 7.36 (d, J=7.5 Hz, 1H), 7.23 (s, 1H), 7.19 (d, J=7.8 Hz, 1H), 7.09 (d, J=7.8 Hz, 1H), 7.00 (s, 1H), 3.93 (t, J=8.1 Hz, 2H), 3.77 (s, 3H), 3.47 (d, J=11.7 Hz, 2H), 3.19 (d, J=4.4 Hz, 2H), 3.06 (t, J=12.6 Hz, 2H), 2.98 (s, 1H), 2.86 (t, J=8.2 Hz, 2H), 2.57 (s, 1H), 2.19 (s, 1H), 2.09 (d, J=13.6 Hz, 2H), 1.65-1.53 (m, 3H), 1.35 (dd, J=11.8, 7.6 Hz, 1H). mp 170-174° C. LRMS [M+H]$^+$: 442.2.

Example 40 Trans-2-(1-(methylsulfonyl)indolin-5-yl)-N-(piperidin-4-ylmethyl)cyclopropylamine (A40)

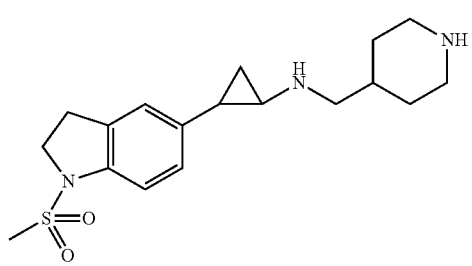 [SMILES: CS(=O)(=O)N1CCc2cc(C3CC3NCC3CCNCC3)ccc21]

The preparation was carried out by the same manner as in Example 32 to give the product A40, yield 48%. $^1$H NMR (400 MHz, MeOD) δ 7.31 (d, J=8.3 Hz, 1H), 7.14 (s, 1H), 7.07 (d, J=8.3 Hz, 1H), 3.98 (t, J=8.5 Hz, 2H), 3.47 (d, J=13.1 Hz, 2H), 3.21 (d, J=6.9 Hz, 2H), 3.15 (t, J=8.5 Hz, 2H), 3.07 (t, J=11.7 Hz, 2H), 3.06-2.94 (m, 1H), 2.90 (s, 3H), 2.63-2.57 (m, 1H), 2.19 (s, 1H), 2.10 (d, J=14.2 Hz, 2H), 1.66-1.51 (m, 3H), 1.38 (dd, J=14.2, 6.9 Hz, 1H). mp 203-206° C. LRMS [M+H]$^+$: 350.1.

Example 41 trans-N-(piperidin-4-ylmethyl)-2-(1-(propylsulfonyl)indolin-5-yl)cyclopropylamine (A41)

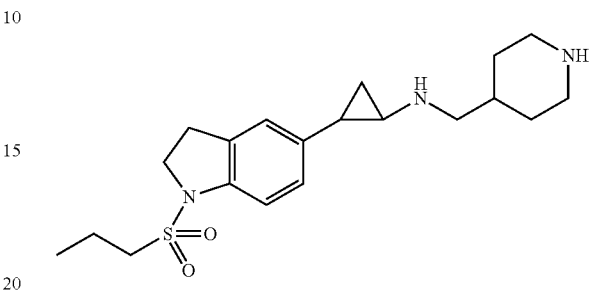

The preparation was carried out by the same manner as in Example 32 to give the product A41, yield 39%. $^1$H NMR (400 MHz, MeOD) δ 7.29 (d, J=8.3 Hz, 1H), 7.12 (s, 1H), 7.05 (d, J=8.4 Hz, 1H), 4.02 (t, J=8.5 Hz, 2H), 3.47 (d, J=13.0 Hz, 2H), 3.21 (d, J=7.0 Hz, 2H), 3.15 (t, J=8.5 Hz, 2H), 3.12-3.05 (m, 4H), 3.01 (dd, J=7.7, 3.9 Hz, 1H), 2.58 (dd, J=7.3, 3.1 Hz, 1H), 2.19 (ddd, J=11.2, 7.5, 3.3 Hz, 1H), 2.10 (d, J=15.3 Hz, 2H), 1.87-1.75 (m, 2H), 1.64-1.52 (m, 3H), 1.38 (dd, J=14.3, 6.8 Hz, 1H), 1.03 (t, J=7.5 Hz, 3H). mp 187-191° C. LRMS [M+H]$^+$: 378.2.

Example 42 trans-N-(piperidin-4-ylmethyl)-2-(1-(trifluoromethanesulfonyl)indolin-5-yl)cyclopropylamine (A42)

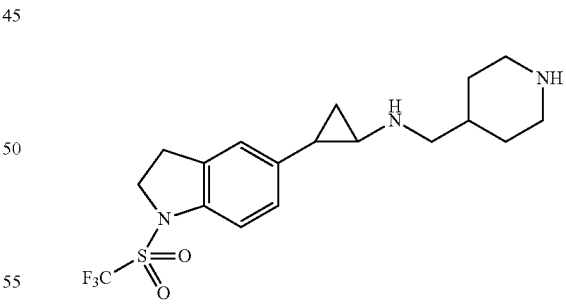

The preparation was carried out by the same manner as in Example 32 to give the product A42, yield 41%. $^1$H NMR (400 MHz, MeOD) δ 7.34 (d, J=8.4 Hz, 1H), 7.20 (s, 1H), 7.12 (d, J=8.4 Hz, 1H), 4.25 (t, J=8.3 Hz, 2H), 3.47 (d, J=13.0 Hz, 2H), 3.27-3.19 (m, 4H), 3.12-3.01 (m, 3H), 2.63 (ddd, J=10.3, 6.5, 3.5 Hz, 1H), 2.26-2.15 (m, 1H), 2.10 (d, J=14.5 Hz, 2H), 1.68-1.53 (m, 3H), 1.41 (dd, J=14.4, 6.9 Hz, 1H). mp 227-230° C. LRMS [M+H]$^+$: 404.2.

Example 43 trans-2-(1-(cyclohexylsulfonyl)indolin-5-yl)-N-(piperidin-4-ylmethyl)cyclopropylamine (A43)

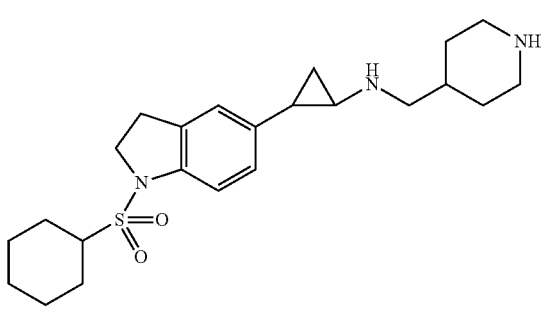 [SMILES: O=S(=O)(C1CCCCC1)N1CCc2cc(C3CC3NCC3CCNCC3)ccc21]

The preparation was carried out by the same manner as in Example 32 to give the product A43, yield 40%. $^1$H NMR (400 MHz, MeOD) δ 7.27 (d, J=8.3 Hz, 1H), 7.10 (s, 1H), 7.02 (d, J=8.4 Hz, 1H), 4.07 (t, J=8.6 Hz, 2H), 3.47 (d, J=13.2 Hz, 3H), 3.21 (d, J=7.0 Hz, 2H), 3.16 (t, J=8.6 Hz, 2H), 3.07 (t, J=11.6 Hz, 3H), 3.02-2.97 (m, 1H), 2.58 (ddd, J=10.3, 6.6, 3.6 Hz, 1H), 2.23-2.17 (m, 1H), 2.10 (d, J=14.2 Hz, 2H), 2.03 (d, J=12.9 Hz, 2H), 1.84 (d, J=13.2 Hz, 2H), 1.69 (d, J=11.8 Hz, 1H), 1.57 (ddd, J=12.0, 7.2, 2.5 Hz, 5H), 1.37 (dd, J=14.4, 6.8 Hz, 1H), 1.29 (dd, J=7.7, 4.6 Hz, 2H). mp 205-206° C. LRMS [M+H]$^+$: 418.3.

Example 44 trans-2-(1-(tert-butylsulfonyl)indolin-5-yl)-N-(piperidin-4-ylmethyl)cyclopropylamine (A44)

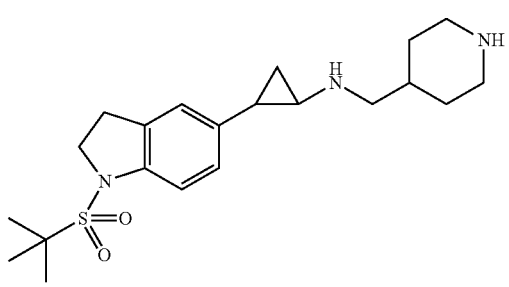 [SMILES: CC(C)(C)S(=O)(=O)N1CCc2cc(C3CC3NCC3CCNCC3)ccc21]

The preparation was carried out by the same manner as in Example 32 to give the product A44, yield 40%. $^1$H NMR (500 MHz, Deuterium Oxide) δ 7.01-6.93 (m, 2H), 6.58 (d, J=7.5 Hz, 1H), 4.70 (s, 2H), 4.49 (ddd, J=12.5, 9.7, 8.1 Hz, 1H), 4.27 (ddd, J=12.5, 8.3, 1.3 Hz, 1H), 3.24-3.10 (m, 3H), 2.91 (ddd, J=18.3, 9.7, 8.4 Hz, 1H), 2.80-2.68 (m, 3H), 2.47 (d, J=6.8 Hz, 2H), 1.99 (q, J=7.0 Hz, 2H), 1.74-1.63 (m, 2H), 1.49 (s, 9H), 1.39-1.31 (m, 2H), 1.33-1.22 (m, 2H), 1.01 (td, J=7.0, 4.9 Hz, 1H), 0.79 (td, J=7.0, 4.9 Hz, 1H). LRMS [M+H]$^+$: 392.2.

Example 45 trans-phenyl (5-(2-(piperidin-4-ylmethylamino)cyclopropyl)indolin-1-yl)methanone (A45)

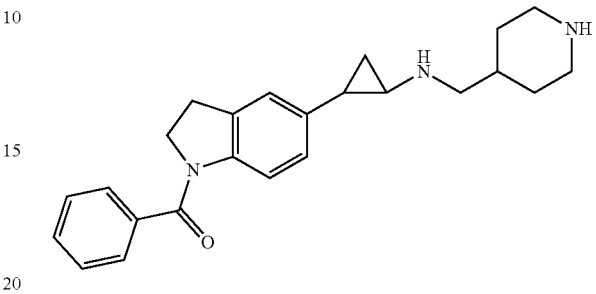

The preparation was carried out by the same manner as in Example 32 to give the product A45, yield 39%. $^1$H NMR (400 MHz, DMSO) δ 9.70 (s, 2H), 9.06 (s, 1H), 8.94 (s, 1H), 8.20-7.92 (m, 1H), 7.63-7.42 (m, 5H), 7.14-6.93 (m, 2H), 4.00 (t, J=8.1 Hz, 2H), 3.26 (d, J=11.9 Hz, 2H), 3.05 (t, J=8.1 Hz, 2H), 2.99 (s, 1H), 2.92-2.76 (m, 3H), 2.61 (s, 1H), 2.08 (s, 1H), 1.97 (d, J=14.1 Hz, 2H), 1.61 (s, 1H), 1.45 (dd, J=22.6, 10.3 Hz, 2H), 1.27-1.10 (m, 2H). mp 202-204° C. LRMS [M+H]$^+$: 376.1.

Example 46 Trans-naphthalen-2-yl (5-(2-(piperidin-4-ylmethylamino)cyclopropyl)indolin-1-yl)methanone (A46)

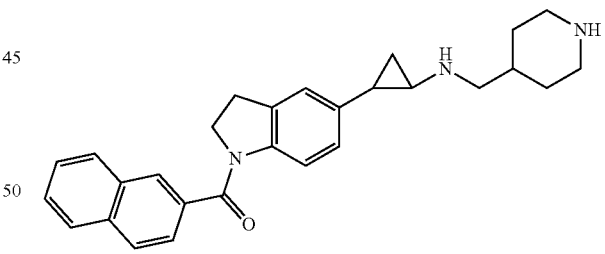

The preparation was carried out by the same manner as in Example 32 to give the product A46, yield 41%. $^1$H NMR (500 MHz, Deuterium Oxide) δ 8.19 (t, J=1.5 Hz, 1H), 7.97 (dd, J=7.5, 1.6 Hz, 1H), 7.88 (ddt, J=7.3, 3.1, 1.5 Hz, 2H), 7.66-7.49 (m, 4H), 7.16-7.09 (m, 2H), 4.70 (s, 2H), 4.16 (ddd, J=12.5, 8.3, 5.0 Hz, 1H), 3.90 (ddd, J=12.6, 9.0, 7.1 Hz, 1H), 3.26 (ddd, J=8.8, 6.0, 3.8 Hz, 2H), 3.15 (dt, J=12.5, 7.0 Hz, 2H), 2.82-2.69 (m, 3H), 2.47 (d, J=6.8 Hz, 2H), 1.97 (q, J=7.0 Hz, 1H), 1.70 (dq, J=13.7, 6.9 Hz, 2H), 1.39-1.21 (m, 3H), 1.05 (td, J=6.9, 4.9 Hz, 1H), 0.79 (td, J=7.0, 4.9 Hz, 1H). LRMS [M+H]$^+$: 426.2.

Example 47 Trans-biphenyl-4-yl(5-(2-(piperidin-4-ylmethylamino)cyclopropyl)indolin-1-yl)methanone (A47)

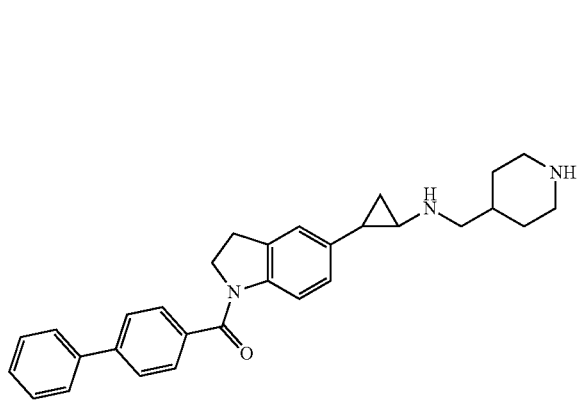 [SMILES: O=C(c1ccc(-c2ccccc2)cc1)N1CCc2cc(C3CC3NCC3CCNCC3)ccc21]

The preparation was carried out by the same manner as in Example 32 to give the product A47, yield 42%. $^1$H NMR (400 MHz, DMSO) δ 9.65 (s, 2H), 9.00 (s, 1H), 8.85 (s, 1H), 7.79 (d, J=8.0 Hz, 2H), 7.74 (d, J=7.5 Hz, 2H), 7.67 (d, J=7.1 Hz, 2H), 7.51 (t, J=7.5 Hz, 2H), 7.42 (t, J=7.4 Hz, 1H), 7.06 (M, 2H), 4.07 (t, J=8.1 Hz, 2H), 3.26 (d, J=13.1 Hz, 3H), 3.07 (t, J=8.0 Hz, 2H), 2.99 (d, J=4.4 Hz, 2H), 2.91-2.80 (m, 3H), 2.60 (s, 1H), 2.07 (s, 1H), 1.97 (d, J=13.2 Hz, 2H), 1.65-1.56 (m, 1H), 1.44 (dd, J=24.9, 13.2 Hz, 3H). mp 179-180° C. LRMS [M+H]$^+$: 452.3.

Example 48 Trans-(5-(2-(piperidin-4-ylmethylamino)cyclopropyl)indolin-1-yl)(3-(trifluoromethyl)phenyl) methanone (A48)

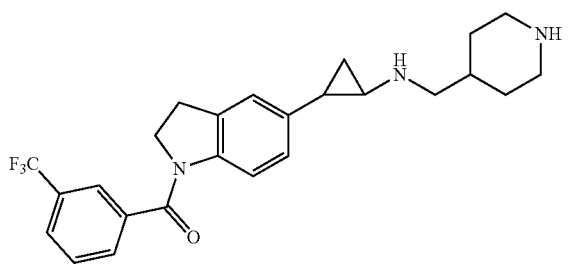 [SMILES: O=C(c1cccc(C(F)(F)F)c1)N1CCc2cc(C3CC3NCC3CCNCC3)ccc21]

The preparation was carried out by the same manner as in Example 32 to give the product A48, yield 43%. $^1$H NMR (400 MHz, DMSO) δ 8.08 (s, 1H), 7.94-7.78 (m, 3H), 7.71 (t, J=7.8 Hz, 1H), 7.15-7.00 (m, 2H), 4.05 (s,2H), 3.44 (d, J=13.0 Hz, 2H), 3.19 (d, J=6.8 Hz, 2H), 3.14 (t, J=8.2 Hz, 2H), 3.04 (t, J=12.0 Hz, 3H), 2.59 (s, 1H), 2.22-2.12 (m, 1H), 2.09 (s, 2H), 1.64-1.49 (m, 3H), 1.38 (dd, J=12.2, 5.9 Hz, 1H). mp 230-232° C. LRMS [M+H]$^+$: 444.1.

Example 49 Trans-2-phenyl-1-(5-(2-(piperidin-4-ylmethylamino)cyclopropyl)indolin-1-yl)ethanone (A49)

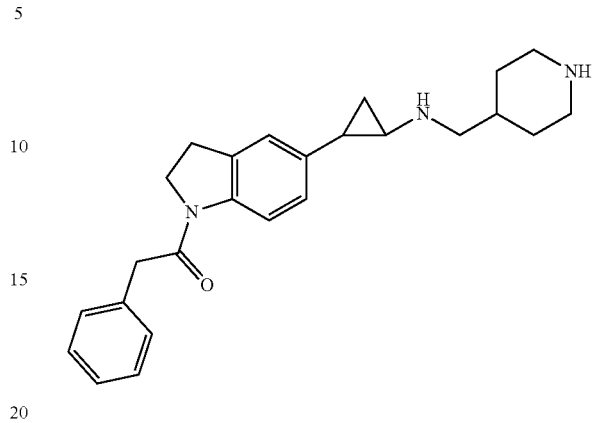

The preparation was carried out by the same manner as in Example 32 to give the product A49, yield 42%. $^1$H NMR (400 MHz, MeOD) δ 8.07 (d, J=8.3 Hz, 1H), 7.39-7.24 (m, 5H), 7.09 (s, 1H), 7.03 (d, J=8.4 Hz, 1H), 4.17 (t, J=8.4 Hz, 2H), 3.89 (s, 2H), 3.46 (d, J=13.0 Hz, 2H), 3.23-3.14 (m, 4H), 3.10-2.98 (m, 3H), 2.59 (ddd, J=10.3, 6.4, 3.5 Hz, 1H), 2.24-2.15 (m, 1H), 2.09 (d, J=14.8 Hz, 2H), 1.65-1.52 (m, 3H), 1.38 (dd, J=14.1, 6.9 Hz, 1H). mp 234-237° C. LRMS [M+H]$^+$: 390.1.

Example 50 Trans-benzyl-5-(2-(piperidin-4-ylmethylamino)cyclopropyl)Indoline-1-carboxylate (A50)

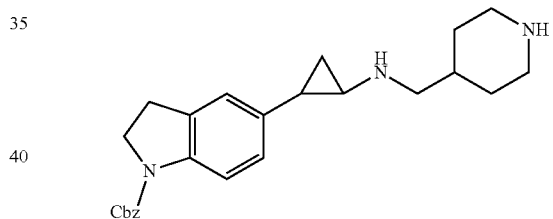

The preparation was carried out by the same manner as in Example 32 to give the product A50, yield 43%. $^1$H NMR (400 MHz, CD$_3$OD) δ 7.45-7.28 (m, 6H), 7.07-6.93 (m, 2H), 5.22 (s, 2H), 4.02 (t, J=7.70 Hz, 2H), 3.44 (d, J=10.2 Hz, 2H), 3.18 (s, 2H), 3.10 (t, J=7.69 Hz, 2H), 3.05-2.90 (m, 3H), 2.55 (s, 1H), 2.18 (s, 1H), 2.07 (d, J=12.6 Hz, 2H), 1.56 (s, 3H), 1.34 (s, 1H). mp 215-218° C. LRMS [M+H]$^+$: 406.2.

Example 51 Trans-1-(5-(2-(piperidin-4-ylmethylamino)cyclopropyl)indolin-1-yl)ethanone (A51)

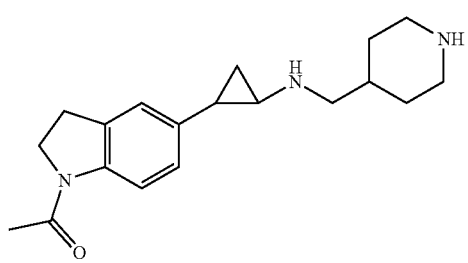 [SMILES: CC(=O)N1CCc2cc(C3CC3NCC3CCNCC3)ccc21]

The preparation was carried out by the same manner as in Example 32 to give the product A51, yield 43%. $^1$H NMR (500 MHz, Deuterium Oxide) δ 7.08 (dq, J=4.1, 2.0 Hz, 2H), 4.70 (s, 2H), 4.19 (td, J=7.5, 2.3 Hz, 2H), 3.32 (ddd, J=9.1, 6.3, 2.0 Hz, 2H), 3.15 (dt, J=12.6, 7.1 Hz, 2H), 2.80-2.68 (m, 3H), 2.47 (d, J=6.8 Hz, 2H), 1.97 (s, 3H), 1.96 (q, J=7.0 Hz, 1H), 1.69 (dq, J=13.6, 6.9 Hz, 2H), 1.39-1.20 (m, 3H), 1.04 (td, J=7.0, 5.0 Hz, 1H), 0.78 (td, J=7.1, 5.0 Hz, 1H). LRMS [M+H]$^+$: 314.2.

Example 52 Trans-2,2,2-trifluoro-1-(5-(2-(piperidin-4-ylmethylamino)cyclopropyl)indolin-1-yl)ethanone (A52)

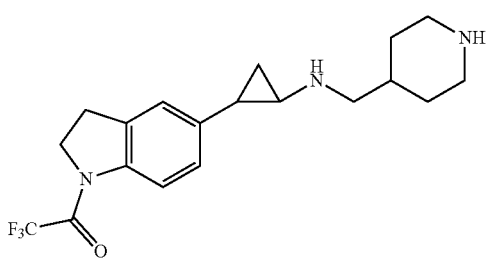 [SMILES: O=C(N1CCc2cc(C3CC3NCC3CCNCC3)ccc21)C(F)(F)F]

The preparation was carried out by the same manner as in Example 32 to give the product A52, yield 34%. $^1$H NMR (500 MHz, Deuterium Oxide) δ 7.47-7.41 (m, 1H), 7.09 (dq, J=3.5, 2.0 Hz, 2H), 4.70 (s, 2H), 4.54 (ddd, J=8.2, 6.5, 3.3 Hz, 2H), 3.41-3.32 (m, 2H), 3.15 (dt, J=12.6, 6.9 Hz, 2H), 2.83-2.68 (m, 3H), 2.47 (d, J=6.4 Hz, 2H), 1.96 (q, J=7.0 Hz, 1H), 1.71 (q, J=6.8 Hz, 2H), 1.39-1.26 (m, 3H), 1.04 (td, J=7.0, 5.0 Hz, 1H), 0.78 (td, J=6.9, 5.0 Hz, 1H). LRMS [M+H]$^+$: 368.2.

Example 53 Trans-1-(5-(2-(piperidin-4-ylmethylamino)cyclopropyl)indolin-1-yl)propan-1-one (A53)

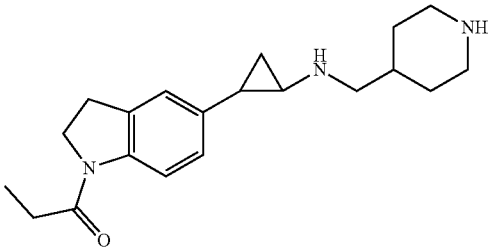 [SMILES: CCC(=O)N1CCc2cc(C3CC3NCC3CCNCC3)ccc21]

The preparation was carried out by the same manner as in Example 32 to give the product A53, yield 48%. $^1$H NMR (400 MHz, MeOD) δ 8.07 (d, J=8.4 Hz, 1H), 7.10 (s, 1H), 7.03 (d, J=8.4 Hz, 1H), 4.13 (t, J=8.5 Hz, 2H), 3.47 (d, J=13.3 Hz, 2H), 3.21 (d, J=7.0 Hz, 3H), 3.11-2.90 (m, 4H), 2.61-2.50 (m, 3H), 2.18 (s, 1H), 2.09 (d, J=14.2 Hz, 2H), 1.65-1.51 (m, 3H), 1.39 (dd, J=14.3, 6.8 Hz, 1H), 1.20 (t, J=7.4 Hz, 3H). mp 250-252° C. LRMS [M+H]$^+$: 328.2.

Example 54 Trans-1-(5-(2-(piperidin-4-ylmethylamino)cyclopropyl)indolin-1-yl)butan-1-one (A54)

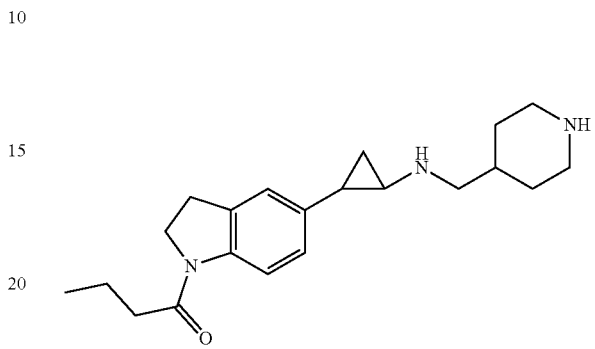

The preparation was carried out by the same manner as in Example 32 to give the product A54, yield 38%. $^1$H NMR (400 MHz, MeOD) δ 8.06 (d, J=8.4 Hz, 1H), 7.10 (s, 1H), 7.03 (d, J=8.1 Hz, 1H), 4.15 (t, J=8.4 Hz, 2H), 3.47 (d, J=12.7 Hz, 2H), 3.21 (d, J=7.3 Hz, 3H), 3.11-2.93 (m, 4H), 2.58 (s, 1H), 2.51 (t, J=7.5 Hz, 2H), 2.19 (s, 1H), 2.09 (d, J=15.0 Hz, 2H), 1.69 (dt, J=15.2, 7.6 Hz, 2H), 1.64-1.51 (m, 3H), 1.45 (dd, J=15.0, 7.5 Hz, 2H), 1.38 (dd, J=13.2, 6.1 Hz, 1H), 0.99 (t, J=7.3 Hz, 3H). mp 215-217° C. LRMS [M+H]$^+$: 342.2.

Example 55 Trans-1-(5-(2-(piperidin-4-ylmethylamino)cyclopropyl)indolin-1-yl)pentan-1-one (A55)

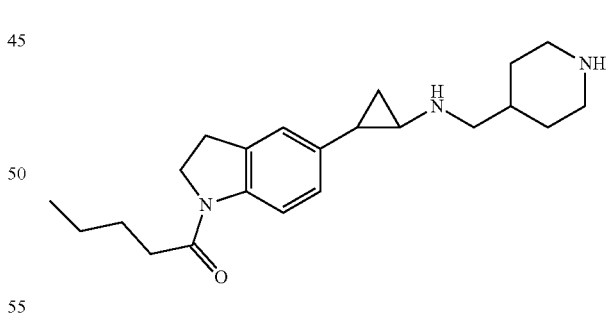

The preparation was carried out by the same manner as in Example 32 to give the product A55, yield 48%. $^1$H NMR (400 MHz, MeOD) δ 8.06 (d, J=8.4 Hz, 1H), 7.10 (s, 1H), 7.03 (d, J=8.1 Hz, 1H), 4.15 (t, J=8.4 Hz, 2H), 3.47 (d, J=12.7 Hz, 2H), 3.21 (d, J=7.3 Hz, 3H), 3.11-2.93 (m, 4H), 2.58 (s, 1H), 2.51 (t, J=7.5 Hz, 2H), 2.19 (s, 1H), 2.09 (d, J=15.0 Hz, 2H), 1.69 (dt, J=15.2, 7.6 Hz, 2H), 1.64-1.51 (m, 3H), 1.45 (dd, J=15.0, 7.5 Hz, 2H), 1.38 (dd, J=13.2, 6.1 Hz, 1H), 0.99 (t, J=7.3 Hz, 3H). mp 216-219° C. LRMS [M+H]$^+$: 356.3.

Example 56 Trans-3-methoxy-1-(5-(2-(piperidin-4-ylmethylamino)cyclopropyl)indolin-1-yl)propan-1-one (A56)

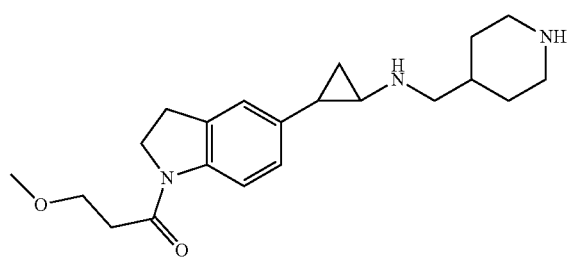 [SMILES: COCCC(=O)N1CCc2cc(C3CC3NCC3CCNCC3)ccc21]

The preparation was carried out by the same manner as in Example 32 to give the product A56, yield 42%. ¹H NMR (400 MHz, MeOD) δ 8.08 (d, J=8.3 Hz, 1H), 7.12 (s, 1H), 7.05 (d, J=8.1 Hz, 1H), 4.25 (s, 2H), 4.08 (t, J=8.4 Hz, 2H), 3.50-3.45 (m, 5H), 3.25-3.19 (m, 4H), 3.11-3.01 (m, 3H), 2.59 (ddd, J=10.3, 6.6, 3.7 Hz, 1H), 2.26-2.15 (m, 1H), 2.10 (d, J=14.6 Hz, 2H), 1.65-1.55 (m, 3H), 1.39 (dd, J=14.4, 6.8 Hz, 1H). mp>300° C. LRMS [M+H]⁺: 344.2.

Example 57 Trans-2-methyl-1-(5-(2-(piperidin-4-ylmethylamino)cyclopropyl)indolin-1-yl)propan-1-one (A57)

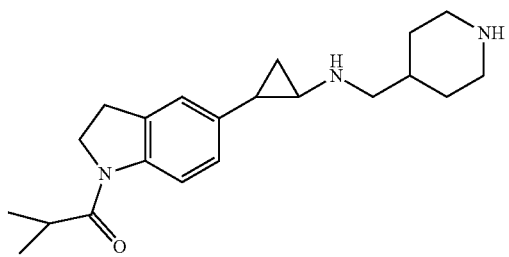

The preparation was carried out by the same manner as in Example 32 to give the product A57, yield 41%. ¹H NMR (500 MHz, Deuterium Oxide) δ 7.45 (d, J=7.4 Hz, 1H), 7.10-7.02 (m, 2H), 4.70 (s, 2H), 4.35 (ddd, J=12.6, 9.2, 7.7 Hz, 1H), 3.97 (ddd, J=12.4, 9.2, 3.0 Hz, 1H), 3.42-3.22 (m, 2H), 3.15 (dt, J=12.4, 7.1 Hz, 2H), 3.05 (hept, J=6.8 Hz, 1H), 2.81-2.68 (m, 3H), 2.47 (d, J=6.9 Hz, 2H), 1.98 (q, J=7.0 Hz, 1H), 1.70 (dq, J=13.8, 7.0 Hz, 2H), 1.40-1.31 (m, 2H), 1.33-1.14 (m, 7H), 1.03 (td, J=7.0, 4.9 Hz, 1H), 0.80 (td, J=7.0, 5.0 Hz, 1H). LRMS [M+H]⁺: 342.2.

Example 58 Trans-2,2-dimethyl-1-(5-(2-(piperidin-4-ylmethylamino)cyclopropyl)indolin-1-yl)propan-1-one (A58)

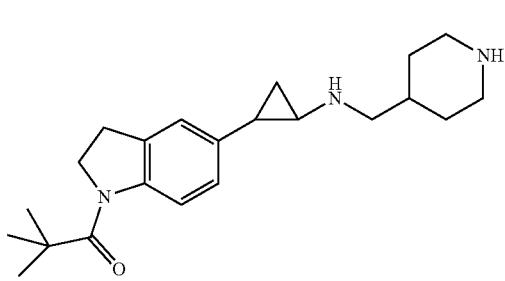 [SMILES: CC(C)(C)C(=O)N1CCc2cc(C3CC3NCC3CCNCC3)ccc21]

The preparation was carried out by the same manner as in Example 32 to give the product A58, yield 44%. ¹H NMR (400 MHz, CD₃OD) δ 8.01 (d, J=8.4 Hz, 1H), 7.08 (s, 1H), 7.00 (d, J=8.4 Hz, 1H), 4.29 (t, J=8.1 Hz, 2H), 3.44 (d, J=13.2 Hz, 2H), 3.18 (d, J=6.9 Hz, 2H), 3.12 (t, J=8.1 Hz, 2H), 3.05-2.96 (m, 3H), 2.58-2.52 (m, 1H), 2.20-2.11 (m, 1H), 2.06 (d, J=14.5 Hz, 2H), 1.60-1.50 (m, 3H), 1.37-1.35 (m, 10H). mp 231-232° C. LRMS [M+H]⁺: 356.2.

Example 59 Trans-cyclohexyl (5-(2-(piperidin-4-ylmethylamino)cyclopropyl)indolin-1-yl)methanone (A59)

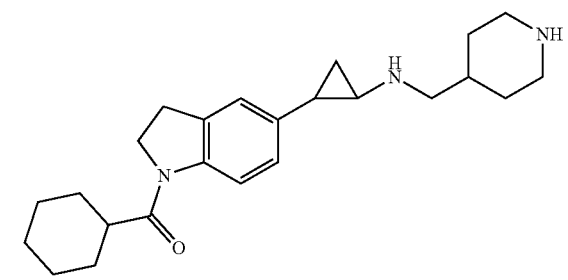

The preparation was carried out by the same manner as in Example 32 to give the product A59, yield 50%. ¹H NMR (400 MHz, CD₃OD) δ 8.05 (d, J=8.4 Hz, 1H), 7.07 (s, 1H), 7.00 (d, J=8.0 Hz, 1H), 4.19 (t, J=8.3 Hz, 2H), 3.45 (d, J=13.1 Hz, 2H), 3.17 (t, J=7.9 Hz, 2H), 3.05 (d, J=12.6 Hz, 2H), 3.02-2.96 (m, 2H), 2.92 (d, J=6.2 Hz, 1H), 2.05 (t, J=14.6 Hz, 3H), 1.90-1.81 (m, 6H), 1.74 (d, J=12.8 Hz, 2H), 1.53 (s, 2H), 1.50 (s, 1H), 1.42-1.37 (m, 4H), 1.34 (d, J=6.7 Hz, 1H). mp 166-168° C. LRMS [M+H]⁺: 382.3

Example 60 Trans-cycloheptyl (5-(2-(piperidin-4-ylmethylamino)cyclopropyl)indolin-1-yl)methanone (A60)

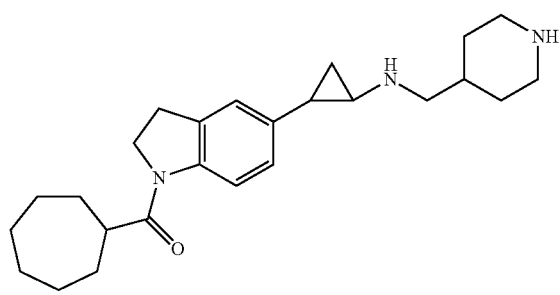 [SMILES: O=C(C1CCCCCC1)N1CCc2cc(C3CC3NCC3CCNCC3)ccc21]

The preparation was carried out by the same manner as in Example 32 to give the product A60, yield 41%. $^1$H NMR (500 MHz, Deuterium Oxide) δ 7.08 (dq, J=3.7, 2.0 Hz, 2H), 4.70 (s, 2H), 4.15 (t, J=7.5 Hz, 2H), 3.40-3.25 (m, 2H), 3.15 (dt, J=12.4, 7.1 Hz, 2H), 2.83 (q, J=7.1 Hz, 1H), 2.73 (dt, J=12.5, 7.1 Hz, 2H), 2.63 (p, J=6.9 Hz, 1H), 2.57-2.44 (m, 4H), 2.15 (dq, J=13.9, 7.1 Hz, 2H), 1.95 (q, J=7.0 Hz, 1H), 1.74 (dq, J=14.1, 7.1 Hz, 2H), 1.55-1.27 (m, 10H), 0.78 (td, J=7.0, 4.9 Hz, 1H). LRMS [M+H]$^+$: 396.2.

Example 61 trans-cyclopentyl (5-(2-(piperidin-4-ylmethylamino)cyclopropyl)indolin-1-yl)methanone (A61)

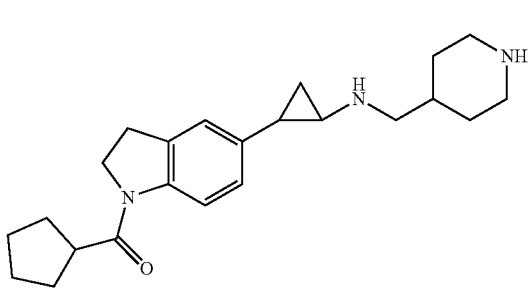 [SMILES: O=C(C1CCCC1)N1CCc2cc(C3CC3NCC3CCNCC3)ccc21]

The preparation was carried out by the same manner as in Example 32 to give the product A61, yield 45%. $^1$H NMR (500 MHz, Deuterium Oxide) δ 7.42 (d, J=7.4 Hz, 1H), 7.10-7.02 (m, 2H), 4.70 (s, 2H), 4.15 (t, J=7.6 Hz, 2H), 3.32 (qt, J=19.0, 7.6 Hz, 2H), 3.20-3.05 (m, 3H), 2.85-2.69 (m, 3H), 2.47 (d, J=6.8 Hz, 2H), 2.10-1.92 (m, 3H), 1.81-1.66 (m, 4H), 1.57-1.27 (m, 7H), 1.03 (td, J=7.0, 4.9 Hz, 1H), 0.78 (td, J=7.0, 4.9 Hz, 1H). LRMS [M+H]$^+$: 368.2.

Example 62 trans-cyclobutyl (5-(2-(piperidin-4-ylmethylamino)cyclopropyl)indolin-1-yl)methanone (A62)

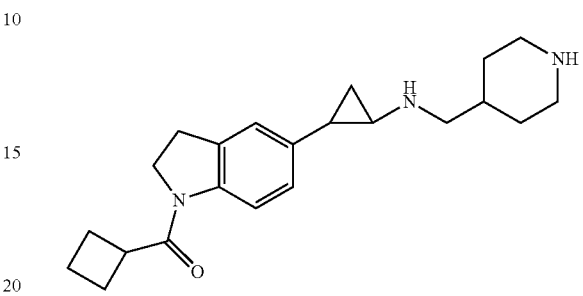

The preparation was carried out by the same manner as in Example 32 to give the product A62, yield 43%. $^1$H NMR (500 MHz, Deuterium Oxide) δ 7.08 (dq, J=3.6, 2.0 Hz, 2H), 4.70 (s, 2H), 4.15 (t, J=7.7 Hz, 2H), 3.43 (p, J=7.0 Hz, 1H), 3.36-3.28 (m, 2H), 3.14 (dt, J=12.5, 7.0 Hz, 2H), 2.80-2.68 (m, 3H), 2.55-2.44 (m, 4H), 2.20-2.09 (m, 2H), 2.06-1.84 (m, 3H), 1.69 (dq, J=13.7, 6.9 Hz, 2H), 1.38-1.19 (m, 3H), 1.04 (td, J=7.0, 5.0 Hz, 1H), 0.78 (td, J=7.0, 5.0 Hz, 1H). LRMS [M+H]$^+$: 354.2.

Example 63 trans-cyclopropyl(5-(2-(piperidin-4-ylmethylamino(cyclopropyl)indolin-1-yl)methanone (A63)

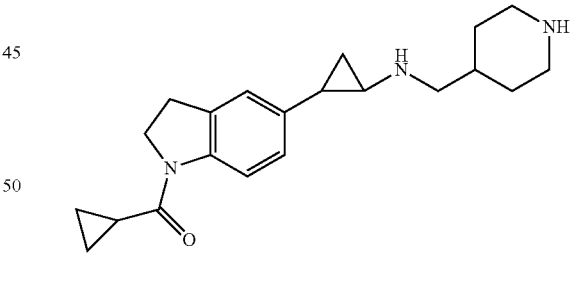

The preparation was carried out by the same manner as in Example 32 to give the product A63, yield 41%. $^1$H NMR (500 MHz, Deuterium Oxide) δ 7.40 (d, J=7.5 Hz, 1H), 7.11-7.02 (m, 2H), 4.70 (s, 2H), 4.15 (t, J=7.6 Hz, 2H), 3.36 (t, J=7.6 Hz, 2H), 3.15 (dt, J=12.5, 7.1 Hz, 2H), 2.82-2.68 (m, 3H), 2.47 (d, J=6.9 Hz, 2H), 1.98 (q, J=6.9 Hz, 1H), 1.77-1.63 (m, 3H), 1.40-1.29 (m, 2H), 1.24 (hept, J=6.9 Hz, 1H), 1.16-1.08 (m, 2H), 1.02 (td, J=6.9, 5.0 Hz, 1H), 0.93 (tt, J=7.2, 4.2 Hz, 2H), 0.80 (td, J=7.0, 4.9 Hz, 1H). LRMS [M+H]$^+$: 340.2.

Example 64 trans-N-(2-(1-(phenylsulfonyl)-1,2,3,4-tetrahydroquinolin-6-yl)cyclopropyl)aniline (A64)

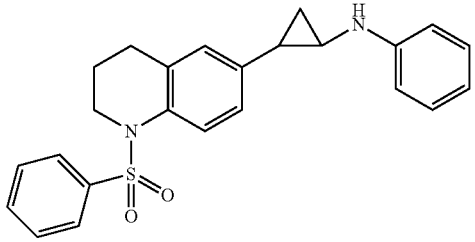 [SMILES: O=S(=O)(c1ccccc1)N1CCCc2cc(C3CC3Nc3ccccc3)ccc21]

The preparation was carried out by the same manner as in Example 2 to give the product A64, yield 41%. $^1$H NMR (500 MHz, Deuterium Oxide) δ 7.66-7.58 (m, 1H), 7.60-7.49 (m, 4H), 7.23-7.09 (m, 3H), 6.92-6.87 (m, 1H), 6.85-6.78 (m, 2H), 6.71 (tt, J=7.5, 2.0 Hz, 1H), 6.58 (d, J=7.5 Hz, 1H), 4.70 (s, 1H), 4.48 (td, J=12.4, 3.4 Hz, 1H), 4.04 (ddt, J=12.4, 4.5, 1.6 Hz, 1H), 2.86 (q, J=7.0 Hz, 1H), 2.77 (dtd, J=15.5, 2.9, 1.4 Hz, 1H), 2.53 (ddd, J=16.0, 13.0, 3.0 Hz, 1H), 2.09 (q, J=7.0 Hz, 1H), 1.93-1.79 (m, 1H), 1.68 (dqd, J=13.2, 3.0, 1.6 Hz, 1H), 1.09 (td, J=6.9, 5.0 Hz, 1H), 0.76 (td, J=7.0, 5.0 Hz, 1H). LRMS [M+H]$^+$: 405.2.

Example 65 trans-N-benzyl-2-(1-(phenylsulfonyl)-1,2,3,4-tetrahydroquinolin-6-yl)cyclopropylamine (A65)

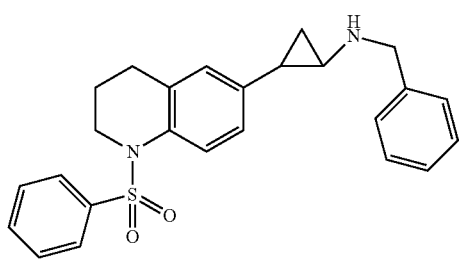 [SMILES: O=S(=O)(c1ccccc1)N1CCCc2cc(C3CC3NCc3ccccc3)ccc21]

The preparation was carried out by the same manner as in Example 3 to give the product A65, yield 39%. LRMS [M+H]$^+$: 419.2.

Example 66 trans-N-(2-(1-(phenylsulfonyl)-1,2,3,4-tetrahydroquinolin-6-yl)cyclopropyl)piperidin-4-amine (A66)

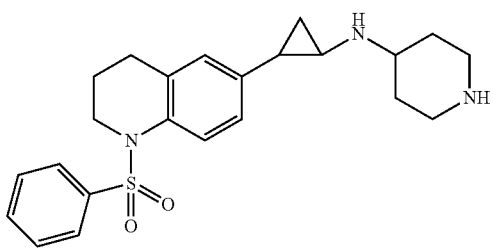 [SMILES: O=S(=O)(c1ccccc1)N1CCCc2cc(C3CC3NC3CCNCC3)ccc21]

The preparation was carried out by the same manner as in Example 15 to give the product A66, yield 41%. $^1$H NMR (500 MHz, Deuterium Oxide) δ 7.80 (dd, J=7.5, 2.0 Hz, 2H), 7.66-7.52 (m, 3H), 7.00-6.93 (m, 2H), 6.58 (d, J=7.4 Hz, 1H), 4.70 (s, 2H), 4.26 (dt, J=12.5, 2.9 Hz, 1H), 3.80-3.70 (m, 1H), 3.13 (dt, J=12.4, 7.1 Hz, 2H), 2.95-2.85 (m, 4H), 2.81 (q, J=7.0 Hz, 1H), 2.72 (p, J=7.0 Hz, 1H), 2.08-1.94 (m, 3H), 1.93-1.82 (m, 2H), 1.57 (dq, J=14.0, 7.1 Hz, 2H), 1.02 (td, J=6.9, 4.9 Hz, 1H), 0.81 (td, J=7.0, 5.0 Hz, 1H). LRMS [M+H]$^+$: 412.2.

Example 67 Trans-2-(1-(phenylsulfonyl)-1,2,3,4-tetrahydroquinolin-6-yl)-N-(piperidin-4-ylmethyl)cyclopropylamine (A67)

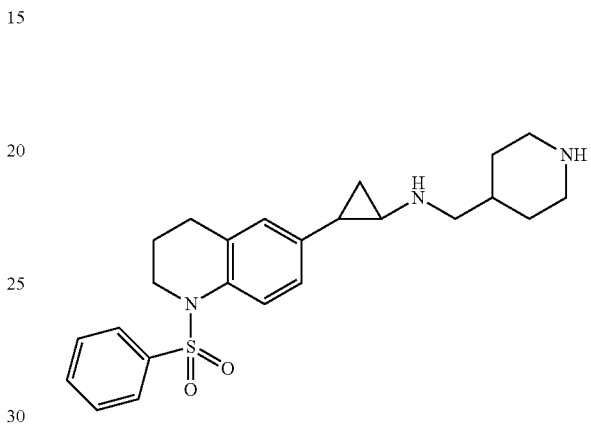

The preparation was carried out by the same manner as in Example 14 to give the product A67, yield 41%. $^1$H NMR (500 MHz, Deuterium Oxide) δ 7.80 (dd, J=7.6, 2.0 Hz, 2H), 7.66-7.52 (m, 3H), 7.01-6.93 (m, 2H), 6.58 (d, J=7.4 Hz, 1H), 4.70 (s, 2H), 4.25 (dt, J=12.3, 2.8 Hz, 1H), 3.78-3.69 (m, 1H), 3.16 (dt, J=12.5, 7.1 Hz, 2H), 2.92-2.71 (m, 5H), 2.47 (d, J=6.9 Hz, 2H), 2.02-1.93 (m, 1H), 1.92-1.82 (m, 2H), 1.74 (dq, J=13.9, 7.0 Hz, 2H), 1.46 (hept, J=6.9 Hz, 1H), 1.34 (dq, J=14.0, 7.1 Hz, 2H), 1.02 (td, J=6.9, 4.9 Hz, 1H), 0.82 (td, J=7.0, 5.0 Hz, 1H). LRMS [M+H]$^+$: 426.2.

Example 68 trans-N-(piperidin-4-ylmethyl)-2-(1-(propylsulfonyl)-1,2,3,4-tetrahydroquinolin-6-yl)cyclopropylamine (A68)

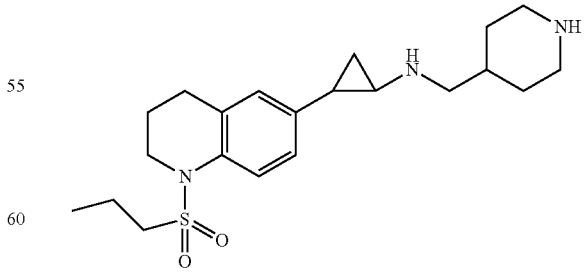

The preparation was carried out by the same manner as in Example 32 to give the product A68, yield 41%. $^1$H NMR (500 MHz, Deuterium Oxide) δ 6.97-6.91 (m, 2H), 4.70 (s, 2H), 4.18 (ddt, J=12.6, 4.0, 1.6 Hz, 1H), 4.08 (td, J=12.3, 3.2

Hz, 1H), 3.14 (dt, J=12.5, 7.1 Hz, 2H), 3.04 (td, J=12.5, 3.6 Hz, 1H), 2.97-2.81 (m, 2H), 2.84-2.65 (m, 4H), 2.47 (d, J=6.9 Hz, 2H), 2.18 (ddtd, J=20.6, 12.7, 8.0, 3.6 Hz, 1H), 2.01-1.93 (m, 2H), 1.93-1.79 (m, 2H), 1.68 (dq, J=13.8, 7.0 Hz, 2H), 1.38-1.17 (m, 3H), 1.04-0.91 (m, 4H), 0.81 (td, J=7.1, 5.0 Hz, 1H). LRMS [M+H]+: 392.2.

Example 69 trans-2-(1-(cyclohexylsulfonyl)-1,2,3,4-tetrahydroquinolin-6-yl)-N-(piperidin-4-ylmethyl)cyclopropylamine (A69)

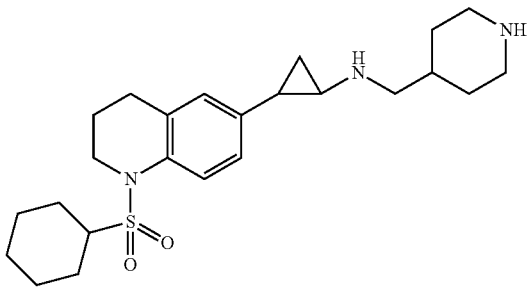 [SMILES: O=S(=O)(C1CCCCC1)N1CCCc2cc(C3CC3NCC3CCNCC3)ccc21]

The preparation was carried out by the same manner as in Example 32 to give the product A69, yield 38%. 1H NMR (500 MHz, Deuterium Oxide) δ 6.94 (t, J=3.8 Hz, 2H), 6.58 (d, J=7.5 Hz, 1H), 4.70 (s, 2H), 3.42 (s, 2H), 3.14 (dt, J=12.4, 7.1 Hz, 2H), 2.94 (d, J=15.0 Hz, 1H), 2.83 (d, J=15.0 Hz, 1H), 2.79-2.69 (m, 3H), 2.47 (s, 2H), 2.37 (dd, J=12.4, 5.9 Hz, 2H), 1.98 (d, J=12.6 Hz, 2H), 1.88 (s, 2H), 1.81-1.68 (m, 4H), 1.72-1.63 (m, 2H), 1.45-1.28 (m, 5H), 1.24 (s, 1H), 1.00 (s, 1H), 0.81 (s, 1H). LRMS [M+H]+: 432.2.

Example 70 trans-phenyl (6-(2-(piperidin-4-ylmethylamino)cyclopropyl)-3,4-dihydroquinolin-1(2H)-yl)methanone (A70)

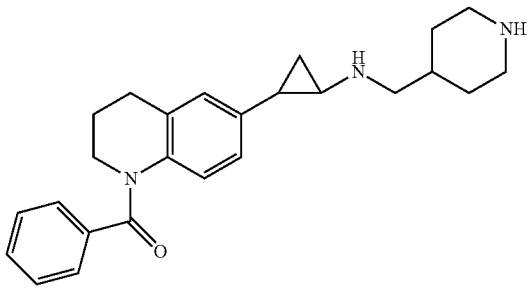 [SMILES: O=C(c1ccccc1)N1CCCc2cc(C3CC3NCC3CCNCC3)ccc21]

The preparation was carried out by the same manner as in Example 32 to give the product A70, yield 32%. 1H NMR (500 MHz, Deuterium Oxide) δ 7.63 (d, J=7.3 Hz, 1H), 7.35-7.21 (m, 5H), 7.12-7.04 (m, 2H), 4.70 (s, 2H), 3.85-3.75 (m, 2H), 3.15 (dt, J=12.4, 7.1 Hz, 2H), 3.00-2.92 (m, 1H), 2.84 (q, J=7.1 Hz, 1H), 2.73 (dt, J=12.4, 7.1 Hz, 2H), 2.47 (d, J=6.9 Hz, 2H), 2.02-1.81 (m, 3H), 1.74 (dq, J=13.9, 7.0 Hz, 2H), 1.46 (hept, J=6.9 Hz, 1H), 1.34 (dt, J=13.2, 7.0 Hz, 2H), 1.02 (td, J=7.0, 5.0 Hz, 1H), 0.79 (td, J=7.0, 4.9 Hz, 1H). LRMS [M+H]+: 390.2.

Example 71 trans-1-(6-(2-(piperidin-4-ylmethylamino)cyclopropyl)-3,4-dihydroquinolin-1(2H)-yl)butan-1-one (A71)

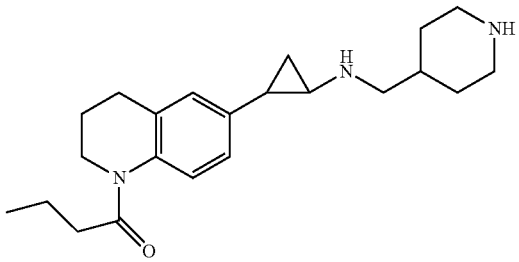 [SMILES: CCCC(=O)N1CCCc2cc(C3CC3NCC3CCNCC3)ccc21]

The preparation was carried out by the same manner as in Example 32 to give the product A71, yield 42%. 1H NMR (500 MHz, Deuterium Oxide) δ 7.33 (d, J=7.3 Hz, 1H), 7.07-7.01 (m, 2H), 4.70 (s, 2H), 3.67-3.56 (m, 1H), 3.19-3.03 (m, 3H), 2.98 (dddd, J=18.3, 3.6, 2.4, 1.2 Hz, 1H), 2.79-2.65 (m, 4H), 2.60 (td, J=12.6, 2.8 Hz, 1H), 2.47 (d, J=6.9 Hz, 2H), 2.03-1.95 (m, 2H), 1.98-1.85 (m, 2H), 1.69 (dq, J=13.9, 7.0 Hz, 2H), 1.41-1.27 (m, 3H), 1.22 (hept, J=6.9 Hz, 1H), 1.07-0.94 (m, 4H), 0.77 (td, J=7.1, 5.0 Hz, 1H). LRMS [M+H]+: 356.2.

Example 72 trans-cyclohexyl(6-(2-(piperidin-4-ylmethylamino)cyclopropyl)-3,4-dihydroquinolin-1(2H)-yl)methanone (A72)

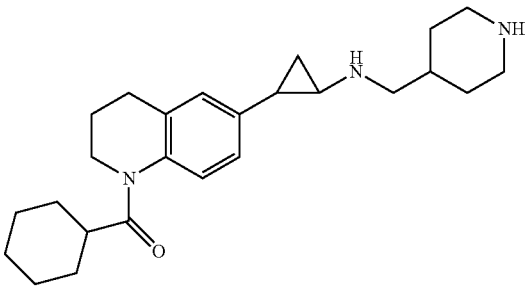 [SMILES: O=C(C1CCCCC1)N1CCCc2cc(C3CC3NCC3CCNCC3)ccc21]

The preparation was carried out by the same manner as in Example 32 to give the product A72, yield 38%. 1H NMR (500 MHz, Deuterium Oxide) δ 7.14 (d, J=7.5 Hz, 1H), 7.05-6.99 (m, 2H), 4.70 (s, 2H), 4.45 (s, 2H), 3.15 (dt, J=12.4, 7.1 Hz, 2H), 3.06 (d, J=16.9 Hz, 1H), 2.96 (d, J=16.9 Hz, 1H), 2.79-2.68 (m, 3H), 2.47 (s, 2H), 2.36 (s, 1H), 2.17-2.09 (m, 2H), 2.10 (s, 2H), 1.95 (s, 1H), 1.87-1.64 (m, 7H), 1.52-1.30 (m, 5H), 1.22 (s, 1H), 1.03 (s, 1H), 0.77 (s, 1H). LRMS [M+H]+: 396.3.

Example 73 Activity Test on Molecular Level

1. LSD1 in vitro activity assay
Screening method: lysine-specific demethylase 1 (LSD1) activity screening
Instrument: enzyme-labeled instrument Envision™ (PerkinElmer, USA).
MATERIALS: Human recombinant LSD1, the obtained LSD1 protein fragment (aa158-end) fused with GST was expressed by *E. coli* expression system and purified.

LSD1 Activity Detection Kit, LANCE Ultra LSD1 Histone H3-Lysine 4 Demethylase Assay was purchased from Perkin Elmer;

The H3 polypeptide substrate ARTK(me1)QTARKSTGGKAPRKQLA-GG-K(Biotin)-NH2 was synthesized by Jill Biochemical Company.

Principle: LSD1 specifically removes the methylation modification at K4 lysine on H3 polypeptide substrate, making it a substrate without methylation. The method employed histone H3 methylated polypeptide (1-24) as a substrate and introduces a biotin label in the C segment of the substrate. When LSD1 was initiated with the participation of FAD, the methylation modification on the substrate H3K4 can be removed. The Eu-labeled H3K4 background antibody binded to the substrate by antigen-antibody reaction, while the streptavidin-labeled receptor binded together by the specific interaction of streptavidin and biotin, thereby the Eu-labeled donor interacting with the streptavidin-labeled receptor. In fluorescence resonance energy transfer, when two fluorophores were brought close due to biomolecular interaction, part of the energy captured by the cryptate when excited would be released, the emission wavelength of which is 620 nm; the other part of the energy was transferred to the acceptor, the emission wavelength of which is 665 nm. The 665 nm emission can only produce by FRET caused by the donor. Therefore, when biomolecules interact, there were two excited lights at 620 nm and 665 nm; when there was no interaction, there was only one excited light at 620 nm. The LSD1 demethylation activity can be reflected by detecting the ratio between the fluorescence signals at the two emission wavelengths of 665 nm and 620 nm. Meanwhile, a blank control was set to determine the strength of the enzyme activity. In the experiment, GSK-2879552 was used as a positive inhibitor; and the structure of GSK-2879552 was as follows:

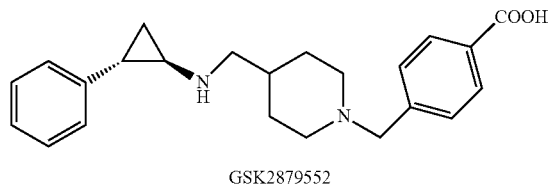 [SMILES: O=C(O)c1ccc(CN2CCC(CN[C@@H]3C[C@H]3c3ccccc3)CC2)cc1]

GSK2879552

Sample treatment: The sample was dissolved in DMSO, and stored at low temperature. The concentration of DMSO in the final system was controlled to a range which would not affect the determined activity.

In the initial screening, the activity of the sample was tested at a single concentration, for example 20 μM. For samples that exhibit activity under certain conditions, for example, the inhibition rate % Inhibition was greater than 50, the active dose-dependent relationship, i.e., the IC50 value, was obtained by nonlinearly fitting the activity of the sample vs the concentration of the sample. The software used for the calculation was Graphpad Prism 5, and the model used for fitting was sigmoidal dose-response (varible slope). For most inhibitor screening models, the bottom and top of the fitted curve were set to 0 and 100.

Experimental Results

| Compound | $IC_{50}$ (nM) |
|---|---|
| A1 | 1792.50 ± 88.39 |
| A3 | 164.00 ± 46.95 |
| A5 | 353.80 ± 31.54 |
| A6 | 261.05 ± 15.77 |
| A7 | 334.50 ± 13.29 |
| A8 | 85.07 ± 5.61 |
| A10 | 222.90 ± 23.90 |
| A14 | 24.43 ± 1.08 |
| A15 | 22.75 ± 0.37 |
| A16 | 38.85 ± 13.32 |
| A17 | 62.21 ± 6.09 |
| A18 | 68.15 ± 0.37 |
| A19 | 62.92 ± 0.11 |
| A20 | 25.01 ± 4.82 |
| A21 | 17.10 ± 1.30 |
| A24 | 48.64 ± 4.19 |
| A25 | 534.40 ± 383.68 |
| A26 | 460.65 ± 31.89 |
| A27 | 71.35 ± 4.30 |
| A28 | 264.70 ± 80.75 |
| A29 | 1692.50 ± 449.01 |
| A32 | 28.17 ± 0.23 |
| A33 | 33.61 ± 2.17 |
| A34 | 43.34 ± 5.09 |
| A35 | 39.49 ± 2.20 |
| A38 | 28.81 ± 0.01 |
| A39 | 38.24 ± 2.96 |
| A40 | 42.53 ± 4.91 |
| A41 | 33.63 ± 3.04 |
| A42 | 41.57 ± 1.05 |
| A43 | 47.54 ± 0.17 |
| A45 | 15.25 ± 1.20 |
| A47 | 10.24 ± 1.59 |
| A48 | 25.57 ± 0.11 |
| A49 | 43.60 ± 2.31 |
| A50 | 35.27 ± 3.48 |
| A53 | 29.90 ± 1.00 |
| A54 | 15.64 ± 1.44 |
| A55 | 50.28 ± 11.75 |
| A56 | 26.95 ± 22.05 |
| A58 | 8.72 ± 0.04 |
| GSK2879552 | 403.90 ± 30.83 |

2. MAOA and MAOB in vitro activity experiments

Screening method: Monoamine oxidase MAOA and MAOB activity screening

Instrument: enzyme-labeled instrument Envision™ (PerkinElmer, USA).

MATERIALS: Human recombinant MAOA was purchased from Promega; human recombinant MAOB was purchased from Sigma;

The MAOA and MAOB activity assay kit, MAO-Glo was purchased from Promega.

Principle: A specific luciferin derivative was used as a substrate. MAOA or MAOB can catalyze the conversion of substrate to luciferin methyl ester. The product luciferin methyl ester can produce fluorescent light under the action of luciferase, so that the activity of MAOA or MAOB can be reflected by the intensity of the fluorescent signal. Meanwhile, a blank control was set to determine the strength of the enzyme activity. Tranylcypromine was used as a positive inhibitor in the experiment.

Sample treatment: The sample was dissolved in DMSO, and stored at low temperature. The concentration of DMSO in the final system was controlled to a range which would not affect the determined activity.

In the initial screening, the activity of the sample was tested at a single concentration, for example 100 μM. For samples exhibiting activity under certain conditions, for example, the inhibition rate % Inhibition is greater than 50, the active dose-dependent relationship, i.e., the IC50 value was obtained by nonlinearly fitting the activity of the sample vs the concentration of the sample, and the software used for the calculation was Graphpad Prism 5. The model used for fitting was sigmoidal dose-response (varible slope), and for most inhibitor screening models, the bottom and top of the fitted curve were set to 0 and 100.

Experimental Results

| Compound | MAO-A IC$_{50}$ (μM) | MAOB IC$_{50}$ (μM) |
|---|---|---|
| A8 | 81.73 ± 0.45 | >100 |
| A14 | >100 | >100 |
| A15 | >100 | >100 |
| A16 | >100 | >100 |
| A17 | 16.18 ± 0.31 | 9.22 ± 0.98 |
| A18 | 96.34 ± 2.05 | >100 |
| A19 | >100 | >100 |
| A20 | >100 | >100 |
| A21 | >100 | >100 |
| A24 | 15.91 ± 2.00 | >100 |
| A27 | >100 | >100 |
| A32 | >100 | 89.38 ± 2.05 |
| A33 | 35.50 ± 0.87 | 81.98 ± 1.39 |
| A34 | >100 | >100 |
| A35 | 49.83 ± 20.92 | 86.16 ± 18.67 |
| A38 | 73.92 ± 1.34 | 40.87 ± 1.41 |
| A39 | 38.57 ± 5.23 | >100 |
| A40 | >100 | >100 |
| A41 | >100 | >100 |
| A42 | 86.57 ± 1.05 | 3.14 ± 0.15 |
| A43 | >100 | >100 |
| A45 | >100 | 32.88 ± 1.24 |
| A47 | >100 | 7.33 ± 0.11 |
| A48 | >100 | 42.55 ± 0.78 |
| A49 | >100 | >100 |
| A50 | >100 | 10.7 ± 1.22 |
| A53 | >100 | >100 |
| A54 | >100 | >100 |
| A55 | >100 | >100 |
| A56 | >100 | >100 |
| A58 | >100 | 70.68 ± 12.62 |
| GSK2879552 | >100 | >100 |

Example 74 Testing Growth-Inhibitory Activity of Compound by MTS Method

Experimental Principle

MTS assay was used to detect the growth inhibitory effect of tested compounds on leukemia cell MV (4:11), the principle of which was that succinate dehydrogenase in mitochondria in living cells can reduce exogenous thiazole blue to insoluble Blue crystalline Formazan.

MATERIALS: Leukemia cell line MV4-11: pediatric acute lymphocytic leukemia, immunological double phenotype, AF4-MLL fusion t (4,11), is a cell growth inhibitory cell line of LSD1 inhibitor (Cancer cell. 2012, 17; 21(4): 473-487).

Experimental Method

1. MV4-11 cells in the logarithmic growth phase were taken, accurately counted 16000 cells/mL, and the diluted cell solution was added to a 96-well plate at 90 μL per well.
2. Fresh medium was taken and sequentially added to a 96-well plate with cell fluid, 90 μL per well.
3. In the compound plate, the compound to be tested at a concentration of 10 mM and the positive compounds ORY-1001 and GSK2879552 were taken and subjected to a 3-fold concentration gradient dilution with DMSO, 8 points for each.
4. 2 μL of the diluted compound was separately added to a 96-well plate containing 98 μL of blank medium, and DMSO group was added with 2 μL of DMSO into 98 μL of blank medium, and mixed for use.
5. The compound homogeneously mixed with the medium was separately added to a 96-well plate in which cells were plated in triplicate, 20 μL per well, and well mixed. In the blank group, 200 μL of IMDM medium was added, and in the DMSO group, 180 μL of the cell-containing medium in DMSO diluted with the medium was added.
6. Incubated for 10 days in an incubator at 37° C., 5% CO$_2$;
7. After 10 days, MTS was added and the values were read after 2.5 h of incubation.

Experimental Results

| Compound | MTS | |
|---|---|---|
| | 3 D (μM) | 10 D (μM) |
| GSK-2879552 | >20 | 1.81 |
| A8 | 1.25 ± 0.51 | 0.6 ± 0.13 |
| A14 | 7.91 ± 1.61 | 1.36 ± 0.92 |
| A15 | 3.40 ± 1.64 | 0.18 ± 0.49 |
| A16 | 8.25 ± 1.70 | 1.21 ± 0.40 |
| A19 | 8.55 ± 1.84 | 1.16 ± 0.26 |
| A45 | >20 | 4.14 ± 3.47 |
| A49 | >20 | 3.23 ± 3.64 |
| A58 | >20 | 1.23 ± 1.13 |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of the following formula I, or a enantiomer, diastereomer, racemate or mixture thereof, or a pharmaceutically acceptable salt, crystalline hydrate, or solvate thereof:

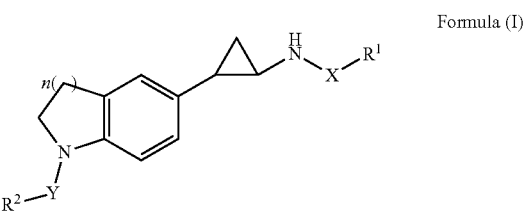

Formula (I)

wherein:

n=1 or 2;

X is none or —(CH$_2$)$_{1-4}$, —CH(Ra)(CH$_2$)$_{0-3}$, —C(Ra)$_2$ (CH$_2$)$_{0-3}$, C3-C6 cycloalkane, carbonyl, or carbonyl-oxo, wherein each Ra of X is independently C1-C4 alkyl;

Y is sulfonyl, carbonyl or carbonyl-oxo;

R$^1$ is selected from —H, substituted or unsubstituted C1-C12 alkyl, substituted or unsubstituted C3-C12 cycloalkyl, substituted or unsubstituted 3-12 membered heterocyclic group (which comprises monocyclic, cyclo, spiro or bridged ring), substituted or unsubstituted C6-C10 aryl, substituted or unsubstituted 5-12 membered aromatic heterocyclic group, wherein R1 has 0, 1, 2, or 3 substituents selected from the group consisting of halogen, aryl, heteroaryl, C1-C6 alkyl, —SO₂Ra, —NC(O)Ra, —CH₂C(O)ORa, —C(O)ORa, —C(O)Ra, —C(O)NRaRb, substituted amino, amino, carbamido, amide, sulfonamide, aralkyl and heteroarylalkyl, wherein said heterocyclic group comprises 1-3 heteroatoms selected from the group consisting of N, O and S, wherein each Ra of $R^1$ is independently hydrogen, phenyl, phenylmethyl, 3,5-dimethylisoxazol-4-yl, 1,2-dimethyl-1H-imidazol-4-yl, C3-C7 cycloalkyl, C1-C6 alkyl, C1-C4 alkoxy, C1-C3 alkylamino or —NHPh, Rb is hydrogen or C1-C3 alkyl, or when Ra and Rb are attached to the same atom, Ra and Rb together form 5- or 6-membered heterocycloalkyl ring;

$R^2$ is selected from substituted or unsubstituted C1-C8 alkyl, substituted or unsubstituted C3-C12 cycloalkyl, substituted or unsubstituted C6-C10 aromatic ring or substituted or unsubstituted 3-12 membered aromatic heterocyclic ring containing 1-4 hetero atoms selected from oxygen, sulfur or nitrogen;

wherein the substituents is/are selected from the group consisting of deuterium, tritium, halogen, C1-C12 alkyl which is unsubstituted or substituted by 1-3 halogen, C1-C12 alkoxy which is unsubstituted or substituted by 1-3 halogens or phenyls, C2-C12 alkenyl which is unsubstituted or substituted by 1-3 halogens, C3-C6 cycloalkyl which is unsubstituted or substituted by 1-3 halogens, C1-C6 alkyl which is substituted by C1-C6 alkoxy, C1-C6 alkyl substituted by C3-C6 cycloalkyl, hydroxy, cyano, nitro, C1-C6 straight or branched hydroxyalkyl, amino group which is unsubstituted or substituted by 1 or 2 C1-C6 alkyls, carboxyl, hydrosulfuryl, or benzyl group which is unsubstituted or substituted by one or more substituents selected from the group consisting of carboxyl, C2-C6 ester group; or any two substituents on the substituted or unsubstituted alkyl, substituted or unsubstituted cycloalkyl, substituted benzene ring or substituted aromatic heterocyclic ring may be bonded together with the adjacent carbon or hetero atom to form a 5-7 membered heterocyclic ring comprising 1 to 3 heteroatoms selected from the group consisting of N, O and S, and the 5-7 membered heterocyclic ring is optionally substituted with a substituent selected from the group consisting of hydrogen, hydrogen isotopes, halogen, trifluoromethyl, methoxy, C1-C6 straight or branched alkyl which is unsubstituted or substituted with 1-3 halogen, C1-C6 straight or branched alkoxy which is unsubstituted or substituted with 1-3 halogen, or hydroxy, wherein the halogen is F, Cl, Br or I.

2. The compound of claim 1, wherein $R^1$ is selected from substituted or unsubstituted C3-C12 cycloalkyl, substituted or unsubstituted 3-10 membered heterocyclic group (which comprises monocyclic, cyclo, spiro or bridged ring), substituted or unsubstituted C6-C10 aryl, wherein R1 has 0, 1, 2, or 3 substituents selected from the group consisting of halogen, aryl, heteroaryl, C1-C6 alkyl, —SO₂Ra, —NC(O)Ra, —CH₂C(O)ORa, —C(O)ORa, —C(O)Ra, —C(O)NRaRb, substituted amino, amino, carbamido, amide, sulfonamide, aralkyl and heteroarylalkyl; wherein said heterocyclic ring comprises 1-3 heteroatoms selected from N or O.

3. The compound of claim 1 wherein $R^2$ is selected from the group consisting of substituted or unsubstituted phenyl, substituted or unsubstituted naphthyl, substituted or unsubstituted 3-7 membered cycloalkyl; wherein when substituted one or more hydrogen atoms are substituted with a substituent selected from the group consisting of halogen, C1-4 alkyl, fluoro C1-4 alkyl and C1-4 alkoxy.

4. The compound of claim 1, wherein Y is sulfonyl or carbonyl.

5. The compound of claim 1, wherein the compound is selected from the following group:

| No. | Name | Structure |
|---|---|---|
| A1 | Trans-2-(1-(phenylsulfonyl)indolin-5-yl)cyclopropylamine | 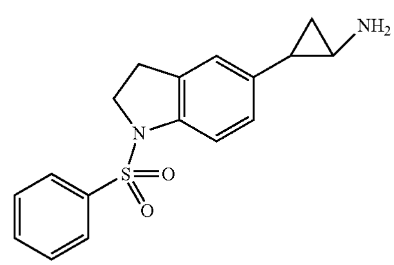 [SMILES: NC1CC1c1ccc2c(c1)CCN2S(=O)(=O)c1ccccc1] |
| A2 | trans-N-phenyl-2-(1-(phenylsulfonyl)indolin-5-yl)cyclopropylamine | 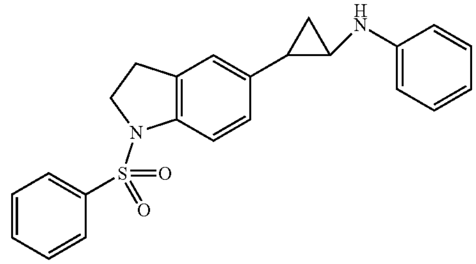 [SMILES: O=S(=O)(c1ccccc1)N1CCc2cc(C3CC3Nc3ccccc3)ccc21] |

-continued

| No. | Name | Structure |
|---|---|---|
| A3 | trans-N-benzyl-2-(1-(phenylsulfonyl)indolin-5-yl)cyclopropylamine | 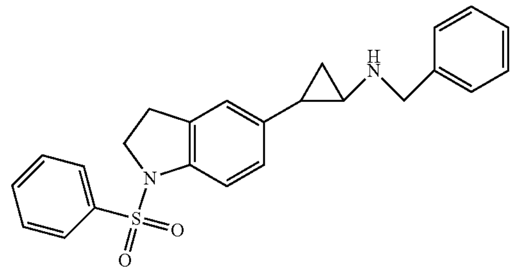 [SMILES: O=S(=O)(c1ccccc1)N1CCc2cc(C3CC3NCc3ccccc3)ccc21] |
| A4 | trans-N-(1-phenylethyl)-2-(1-(phenylsulfonyl)indolin-5-yl)cyclopropylamine | 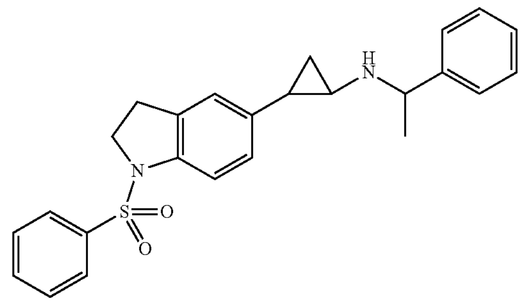 [SMILES: CC(NC1CC1c1ccc2c(c1)CCN2S(=O)(=O)c1ccccc1)c1ccccc1] |
| A5 | trans-N-(4-dimethylamino-benzyl)-2-(1-(phenylsulfonyl)indolin-5-yl)cyclopropylamine | 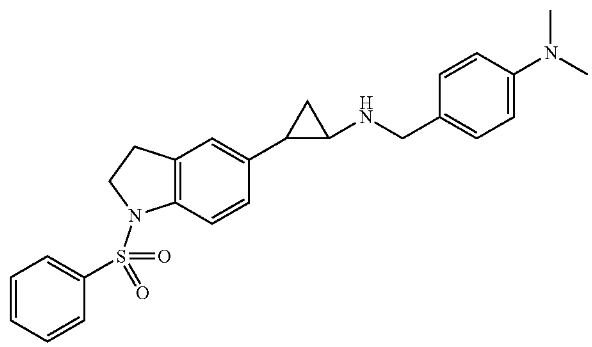 [SMILES: CN(C)c1ccc(CNC2CC2c2ccc3c(c2)CCN3S(=O)(=O)c2ccccc2)cc1] |
| A6 | trans-N-(4-pyridine-methylene)-2-(1-(phenylsulfonyl)indolin-5-yl)cyclopropylamine | 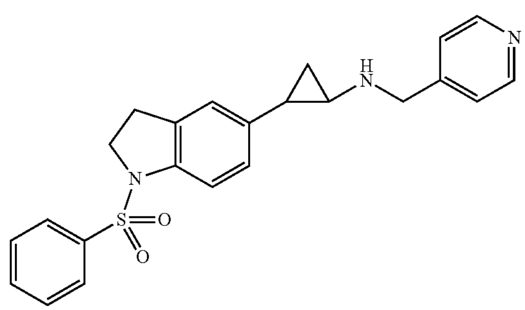 [SMILES: O=S(=O)(c1ccccc1)N1CCc2cc(C3CC3NCc3ccncc3)ccc21] |
| A7 | trans-N-(5-indolylmethylene)-2-(1-(phenylsulfonyl)indolin-5-yl)cyclopropylamine | 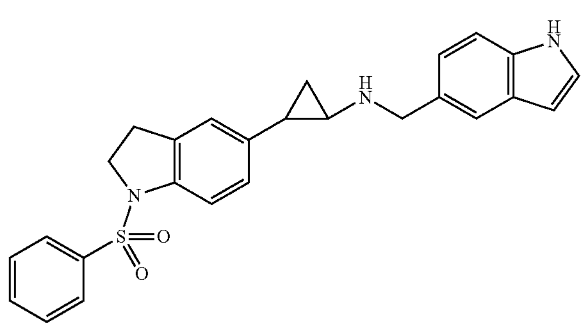 [SMILES: O=S(=O)(c1ccccc1)N1CCc2cc(C3CC3NCc3ccc4[nH]ccc4c3)ccc21] |

-continued

| No. | Name | Structure |
|---|---|---|
| A8 | trans-N-(3-indolylmethylene)-2-(1-(phenylsulfonyl)indolin-5-yl)cyclopropylamine | 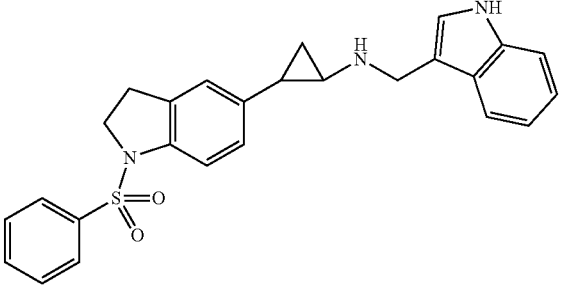 [SMILES: O=S(=O)(c1ccccc1)N1CCc2cc(C3CC3NCc3c[nH]c4ccccc34)ccc21] |
| A9 | trans-N-(2-(1-(phenylsulfonyl)indolin-5-yl)cyclopropyl)cyclohexylamine | 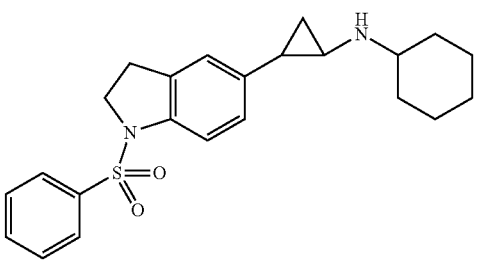 [SMILES: O=S(=O)(c1ccccc1)N1CCc2cc(C3CC3NC3CCCCC3)ccc21] |
| A10 | trans-N-cyclohexamethylene-2-(1-(phenylsulfonyl)indolin-5-yl)cyclopropylamine | 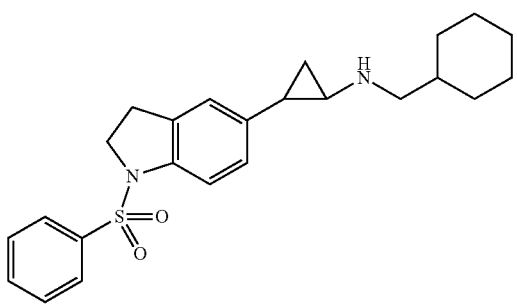 [SMILES: O=S(=O)(c1ccccc1)N1CCc2cc(C3CC3NCC3CCCCC3)ccc21] |
| A11 | trans-N-butyl-2-(1-(phenylsulfonyl)indolin-5-yl)cyclopropylamine | 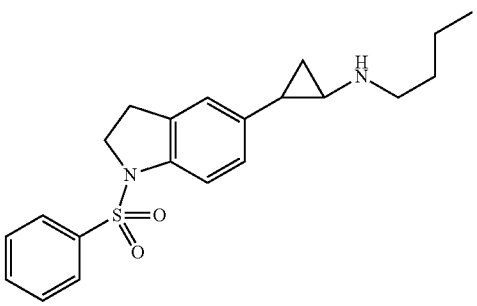 [SMILES: CCCCNC1CC1c1ccc2c(c1)CCN2S(=O)(=O)c1ccccc1] |
| A12 | trans-2-(1-(phenylsulfonyl)indolin-5-yl)-N-((tetrahydro-2H-pyran-4-yl)methyl)cyclopropylamine | 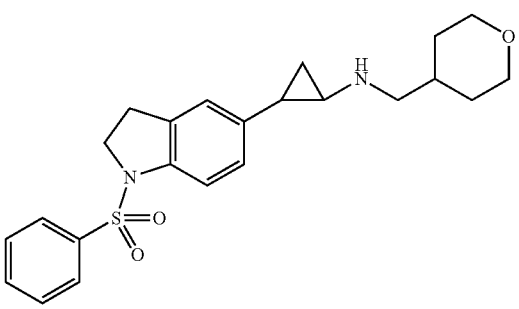 [SMILES: O=S(=O)(c1ccccc1)N1CCc2cc(C3CC3NCC3CCOCC3)ccc21] |

| No. | Name | Structure |
|---|---|---|
| A13 | trans-N-(2-(1-(phenylsulfonyl)indolin-5-yl)cyclopropyl)tetrahydro-2H-pyran-4-amine | 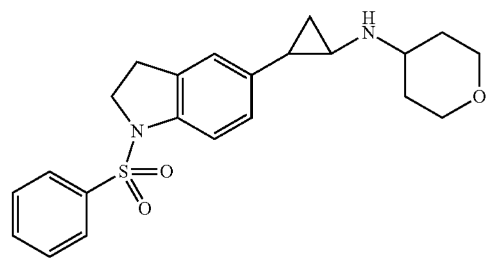 [SMILES: O=S(=O)(c1ccccc1)N1CCc2cc(C3CC3NC3CCOCC3)ccc21] |
| A14 | trans-N-(4-piperidinylmethylene)-2-(1-(phenylsulfonyl)indolin-5-yl)cyclopropylamine | 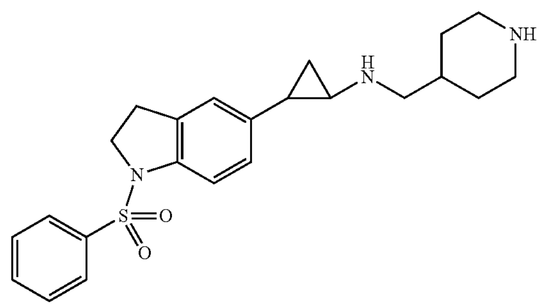 [SMILES: O=S(=O)(c1ccccc1)N1CCc2cc(C3CC3NCC3CCNCC3)ccc21] |
| A15 | trans-N-(4-piperidinyl)-2-(1-(phenylsulfonyl)indolin-5-yl)cyclopropylamine | 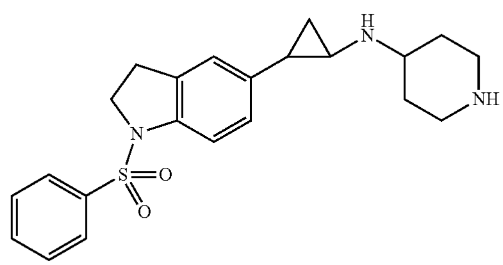 [SMILES: O=S(=O)(c1ccccc1)N1CCc2cc(C3CC3NC3CCNCC3)ccc21] |
| A16 | trans-N-(4-piperidinylethyl)-2-(1-(phenylsulfonyl)porphyrin-5-yl)cyclopropylamine | 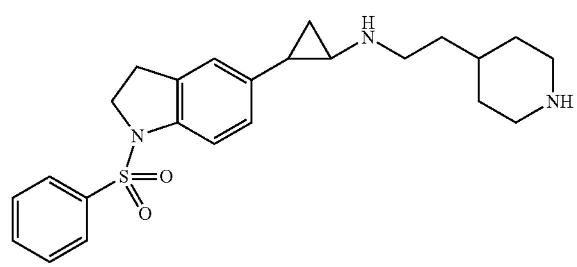 [SMILES: O=S(=O)(c1ccccc1)N1CCc2cc(C3CC3NCCC3CCNCC3)ccc21] |
| A17 | trans-N-(azetidin-3-ylmethyl)-2-(1-(phenylsulfonyl)indolin-5-yl)cyclopropylamine | 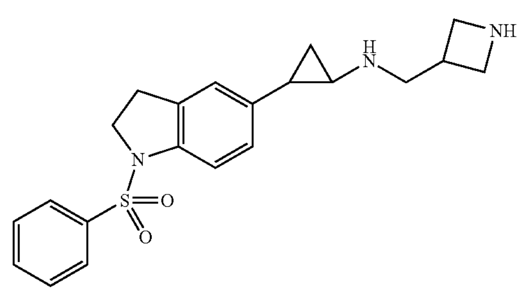 [SMILES: O=S(=O)(c1ccccc1)N1CCc2cc(C3CC3NCC3CNC3)ccc21] |

-continued

| No. | Name | Structure |
|---|---|---|
| A18 | trans-4-((2-(1-(phenylsulfonyl)indolin-5-yl)cyclopropylamino)methyl)cyclohexylamine | 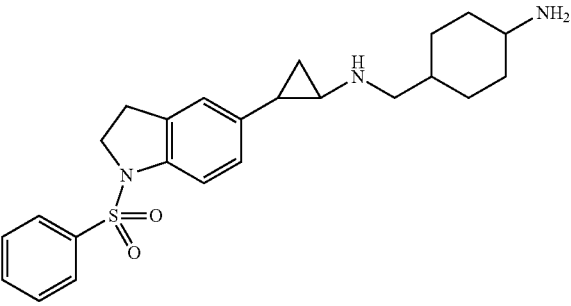 [SMILES: NC1CCC(CNC2CC2c2ccc3c(c2)CCN3S(=O)(=O)c2ccccc2)CC1] |
| A19 | trans-N1-(2-(1-(phenylsulfonyl)indolin-5-yl)cyclopropyl)cyclohexane-1,4-diamine | 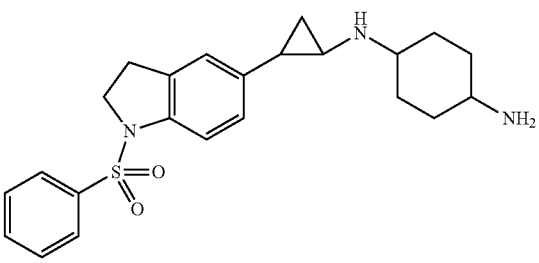 [SMILES: NC1CCC(NC2CC2c2ccc3c(c2)CCN3S(=O)(=O)c2ccccc2)CC1] |
| A20 | trans-N-(2-(1-(phenylsulfonyl)indolin-5-yl)cyclopropyl)-7-azaspiro[3.5]nonane-2-amine | 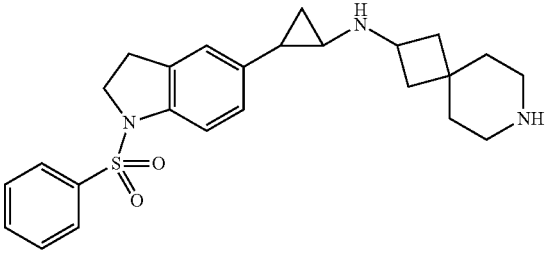 [SMILES: O=S(=O)(c1ccccc1)N1CCc2cc(C3CC3NC3CC4(CCNCC4)C3)ccc21] |
| A21 | trans-N-((4-methylpiperidin-4-yl)methyl)-2-(1-(phenylsulfonyl)indolin-5-yl)cyclopropylamine | 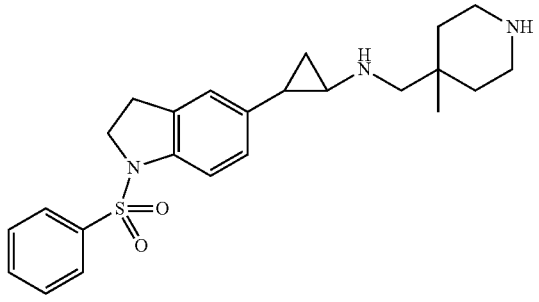 [SMILES: CC1(CNC2CC2c2ccc3c(c2)CCN3S(=O)(=O)c2ccccc2)CCNCC1] |
| A22 | trans-4-((2-(1-(phenylsulfonyl)indolin-5-yl)cyclopropylamino)methyl)piperidine-4-carboxylic acid | 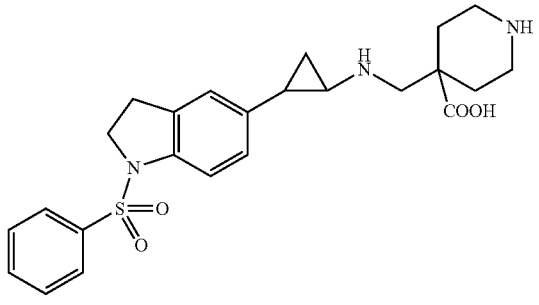 [SMILES: O=C(O)C1(CNC2CC2c2ccc3c(c2)CCN3S(=O)(=O)c2ccccc2)CCNCC1] |

| No. | Name | Structure |
|---|---|---|
| A23 | trans-N-((1-methylpiperidin-4-yl)methyl)-2-(1-(phenylsulfonyl)indolin-5-yl)cyclopropylamine | 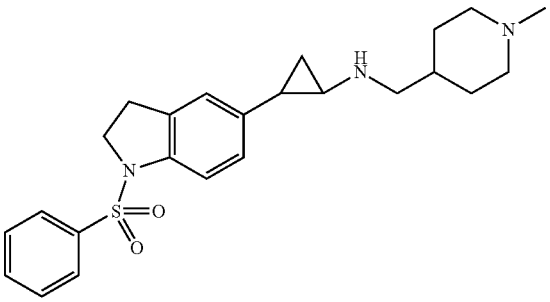 [SMILES: CN1CCC(CNC2CC2c2ccc3c(c2)CCN3S(=O)(=O)c2ccccc2)CC1] |
| A24 | trans-N-((1-benzylpiperidin-4-yl)methyl)-2-(1-(phenylsulfonyl)indolin-5-yl)cyclopropylamine | 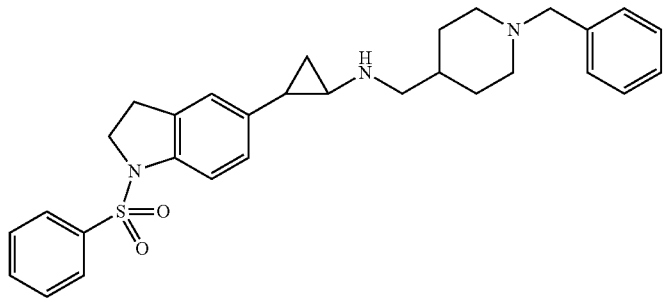 [SMILES: O=S(=O)(c1ccccc1)N1CCc2cc(C3CC3NCC3CCN(Cc4ccccc4)CC3)ccc21] |
| A25 | Trans-tert-butyl 4-((4-((2-(1-(phenylsulfonyl))indolin-5-yl)cyclopropylamino)methyl)piperidin-1-yl)methyl)benzoate | 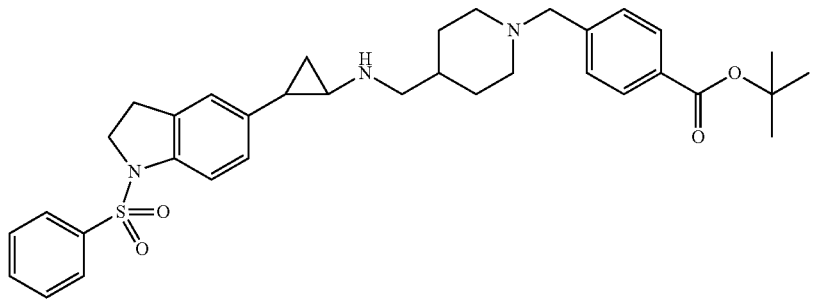 [SMILES: CC(C)(C)OC(=O)c1ccc(CN2CCC(CNC3CC3c3ccc4c(c3)CCN4S(=O)(=O)c3ccccc3)CC2)cc1] |
| A26 | Trans-4-((4-((2-(1-(phenylsulfonyl))indolin-5-yl)cyclopropylamino)methyl)piperidin-1-yl)methyl)benzoic acid | 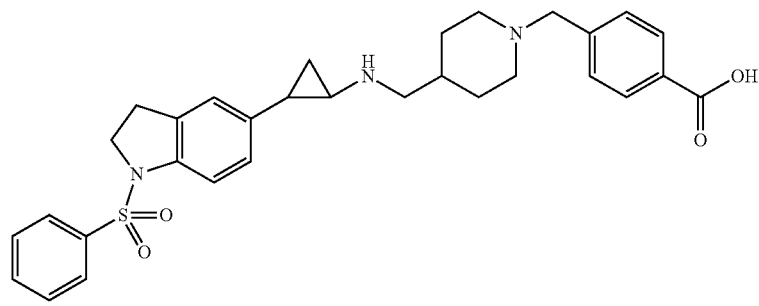 [SMILES: O=C(O)c1ccc(CN2CCC(CNC3CC3c3ccc4c(c3)CCN4S(=O)(=O)c3ccccc3)CC2)cc1] |
| A27 | Trans-tert-butyl 4-((2-(1-(phenylsulfonyl)indolin-5-yl)cyclopropylamino)methyl)piperidine-1-carboxylate | 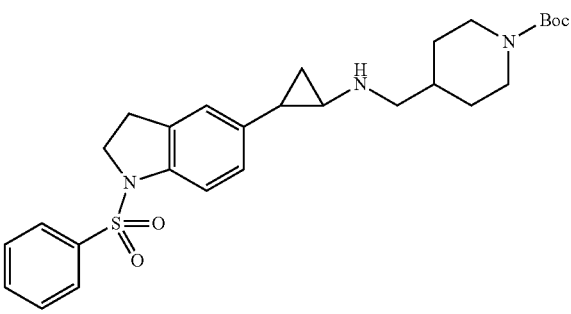 |

-continued

| No. | Name | Structure |
|---|---|---|
| A28 | Trans-benzyl 4-((2-(1-(phenylsulfonyl)indolin-5-yl)cyclopropylamino)methyl)piperidine-1-carboxylate | 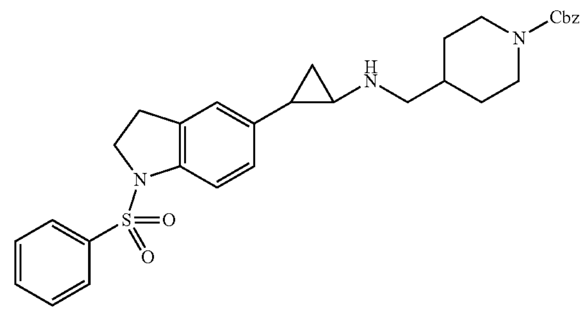 [SMILES: CC(C)(C)OC(=O)N1CCC(CNC2CC2c2ccc3c(c2)CCN3S(=O)(=O)c2ccccc2)CC1] |
| A29 | Trans-tert-butyl 4-(2-(1-(phenylsulfonyl)indolin-5-yl)cyclopropylcarbamoyl)piperidine-1-carboxylate | 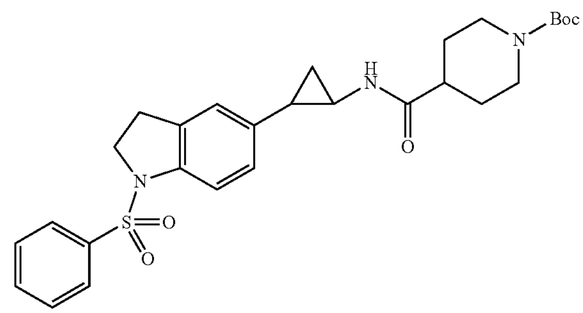 [SMILES: CC(C)(C)OC(=O)N1CCC(C(=O)NC2CC2c2ccc3c(c2)CCN3S(=O)(=O)c2ccccc2)CC1] |
| A30 | Trans-2-(1-(phenylsulfonyl)indolin-5-yl)-N-(1-(piperidin-4-yl)ethyl)cyclopropylamine | 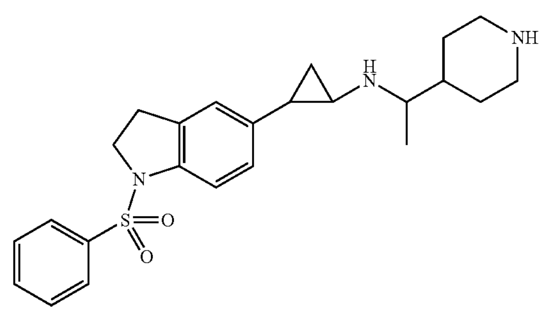 [SMILES: CC(NC1CC1c1ccc2c(c1)CCN2S(=O)(=O)c1ccccc1)C1CCNCC1] |
| A31 | Trans-2-(1-(phenylsulfonyl)indolin-5-yl)-N-(2-(piperidin-4-yl)propan-2-yl)cyclopropylamine | 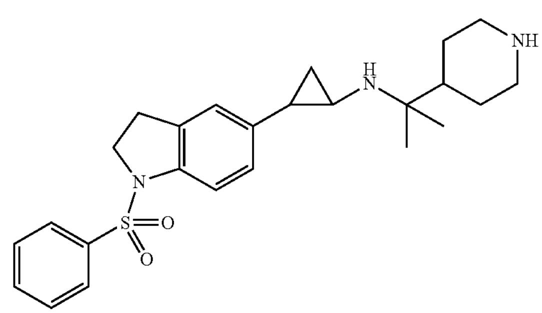 [SMILES: CC(C)(NC1CC1c1ccc2c(c1)CCN2S(=O)(=O)c1ccccc1)C1CCNCC1] |
| A32 | Trans-2-(1-(biphenyl-4-ylsulfonyl)indolin-5-yl)-N-(piperidin-4-ylmethyl)cyclopropylamine | 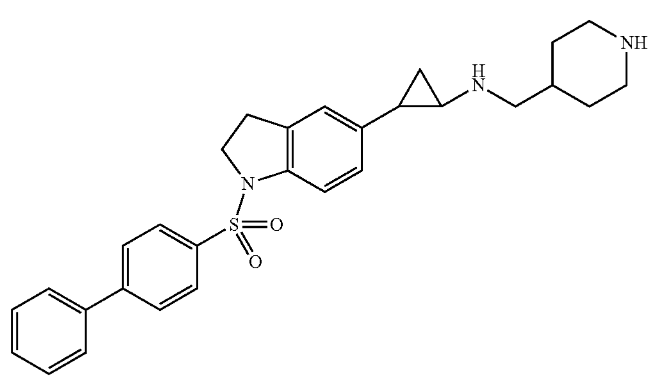 [SMILES: O=S(=O)(c1ccc(-c2ccccc2)cc1)N1CCc2cc(C3CC3NCC3CCNCC3)ccc21] |

-continued

| No. | Name | Structure |
|---|---|---|
| A33 | Trans-2-(1-(naphthalen-2-ylsulfonyl)indolin-5-yl)-N-(piperidin-4-ylmethyl)cyclopropylamine | 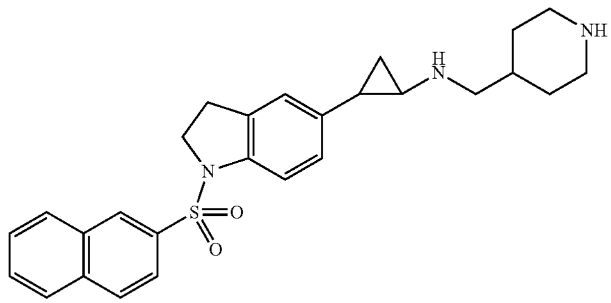 [SMILES: O=S(=O)(c1ccc2ccccc2c1)N1CCc2cc(C3CC3NCC3CCNCC3)ccc21] |
| A34 | trans-N-(piperidin-4-ylmethyl)-2-(1-(4-(trifluoromethyl)benzenesulfonyl)indolin-5-yl)cyclopropylamine | 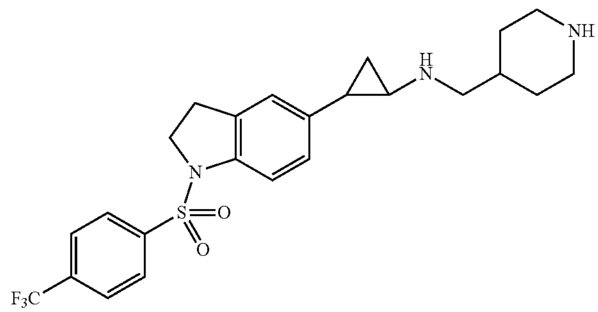 [SMILES: O=S(=O)(c1ccc(C(F)(F)F)cc1)N1CCc2cc(C3CC3NCC3CCNCC3)ccc21] |
| A35 | trans-N-(piperidin-4-ylmethyl)-2-(1-(3-(trifluoromethyl)benzenesulfonyl)indolin-5-yl)cyclopropylamine | 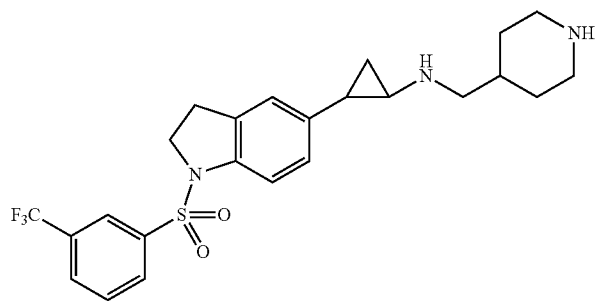 [SMILES: O=S(=O)(c1cccc(C(F)(F)F)c1)N1CCc2cc(C3CC3NCC3CCNCC3)ccc21] |
| A36 | trans-N-(piperidin-4ylmethyl)-2-(1-(2-(trifluoromethyl)benzenesulfonyl)indolin-5-yl)cyclopropylamine | 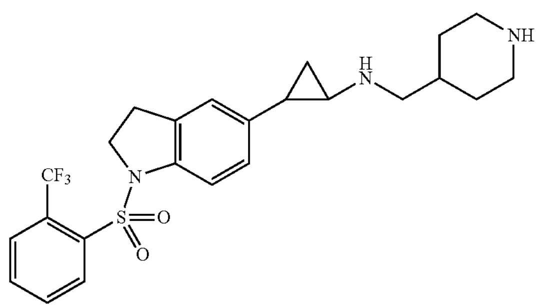 [SMILES: O=S(=O)(c1ccccc1C(F)(F)F)N1CCc2cc(C3CC3NCC3CCNCC3)ccc21] |
| A37 | trans-N-(piperidin-4-ylmethyl)-2-(1-(m-toluenesulfonyl)indolin-5-yl)cyclopropylamine | 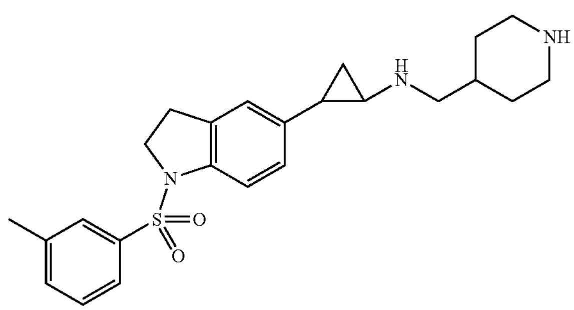 [SMILES: Cc1cccc(S(=O)(=O)N2CCc3cc(C4CC4NCC4CCNCC4)ccc32)c1] |

-continued

| No. | Name | Structure |
|---|---|---|
| A38 | trans-2-(1-(3-chlorobenzenesulfonyl)indolin-5-yl)-N-(piperidin-4-ylmethyl)cyclopropylamine | 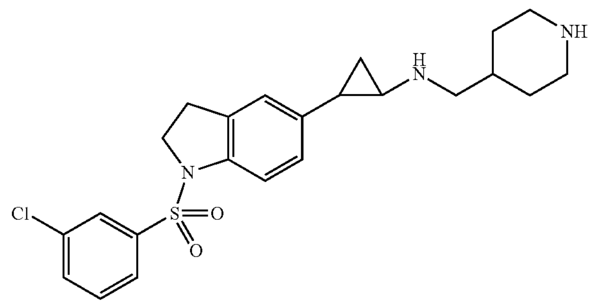 [SMILES: O=S(=O)(c1cccc(Cl)c1)N1CCc2cc(C3CC3NCC3CCNCC3)ccc21] |
| A39 | trans-2-(1-(3-methoxybenzenesulfonyl)indolin-5-yl)-N-(piperidin-4-ylmethyl)cyclopropylamine | 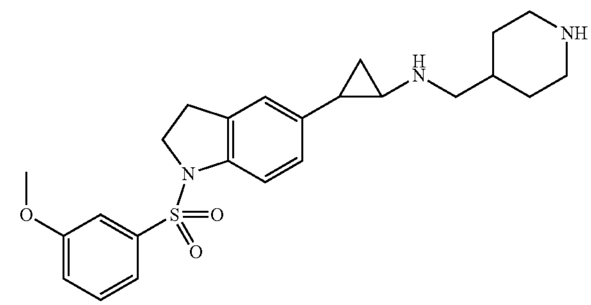 [SMILES: COc1cccc(S(=O)(=O)N2CCc3cc(C4CC4NCC4CCNCC4)ccc32)c1] |
| A40 | Trans-2-(1-(methylsulfonyl)indolin-5-yl)-N-(piperidin-4-ylmethyl)cyclopropylamine | 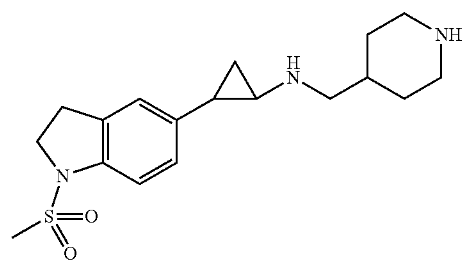 [SMILES: CS(=O)(=O)N1CCc2cc(C3CC3NCC3CCNCC3)ccc21] |
| A41 | trans-N-(piperidin-4-ylmethyl)-2-(1-(propylsulfonyl)indolin-5-yl)cyclopropylamine | 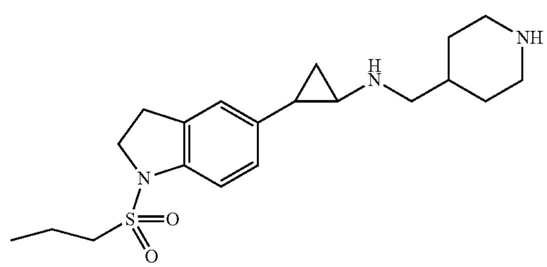 [SMILES: CCCS(=O)(=O)N1CCc2cc(C3CC3NCC3CCNCC3)ccc21] |
| A42 | trans-N-(piperidin-4-ylmethyl)-2-(1-(trifluoromethanesulfonyl)indolin-5-yl)cyclopropylamine | 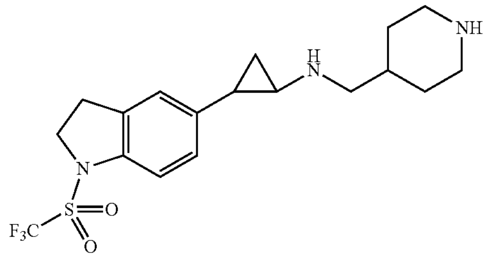 [SMILES: O=S(=O)(N1CCc2cc(C3CC3NCC3CCNCC3)ccc21)C(F)(F)F] |

-continued

| No. | Name | Structure |
|---|---|---|
| A43 | trans-2-(1-(cyclohexylsulfonyl)indolin-5-yl)-N-(piperidin-4-ylmethyl)cyclopropylamine | 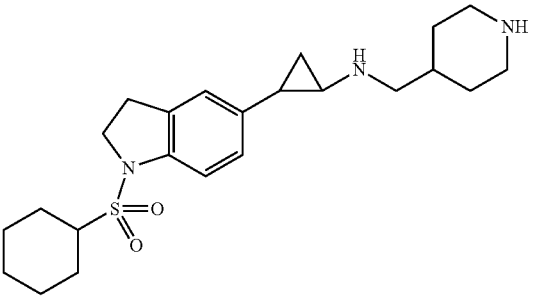 [SMILES: O=S(=O)(C1CCCCC1)N1CCc2cc(C3CC3NCC3CCNCC3)ccc21] |
| A44 | trans-2-(1-(tert-butylsulfonyl)indolin-5-yl)-N-(piperidin-4-ylmethyl)cyclopropylamine | 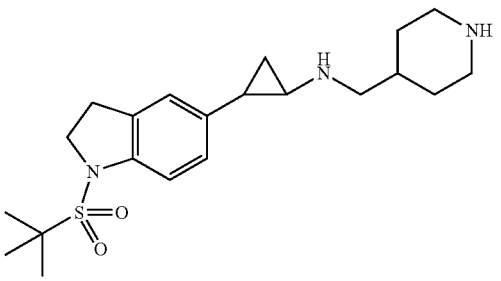 [SMILES: CC(C)(C)S(=O)(=O)N1CCc2cc(C3CC3NCC3CCNCC3)ccc21] |
| A45 | trans-phenyl (5-(2-(piperidin-4-ylmethylamino)cyclopropyl)indolin-1-yl)methanone | 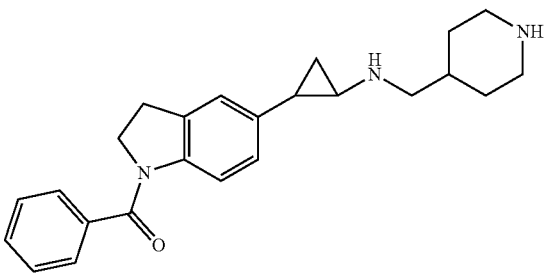 [SMILES: O=C(c1ccccc1)N1CCc2cc(C3CC3NCC3CCNCC3)ccc21] |
| A46 | Trans-naphthalen-2-yl(5-(2-(piperidin-4-ylmethylamino)cyclopropyl)indolin-1-yl)methanone | 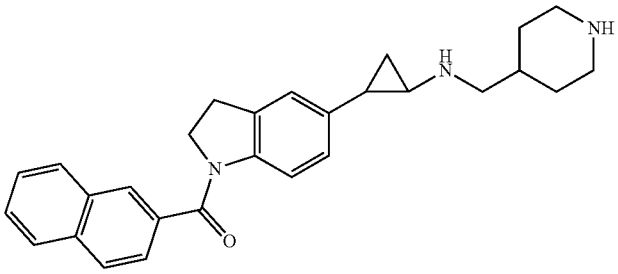 [SMILES: O=C(c1ccc2ccccc2c1)N1CCc2cc(C3CC3NCC3CCNCC3)ccc21] |
| A47 | Trans-biphenyl-4-yl(5-(2-(piperidin-4-ylmethylamino)cyclopropyl)indolin-1-yl)methanone | 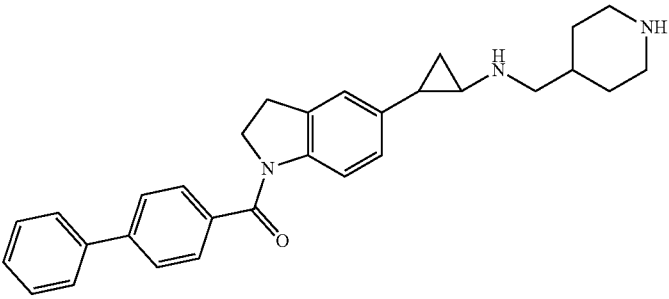 [SMILES: O=C(c1ccc(-c2ccccc2)cc1)N1CCc2cc(C3CC3NCC3CCNCC3)ccc21] |

-continued

| No. | Name | Structure |
|---|---|---|
| A48 | Trans-(5-(2-(piperidin-4-ylmethylamino)cyclopropyl)indolin-1-yl)(3-(trifluoromethyl)phenyl)methanone | 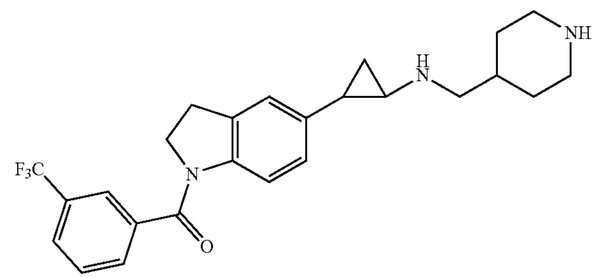 [SMILES: O=C(c1cccc(C(F)(F)F)c1)N1CCc2cc(C3CC3NCC3CCNCC3)ccc21] |
| A49 | Trans-2-phenyl-1-(5-(2-(piperidin-4-ylmethylamino)cyclopropyl)indolin-1-yl)ethanone | 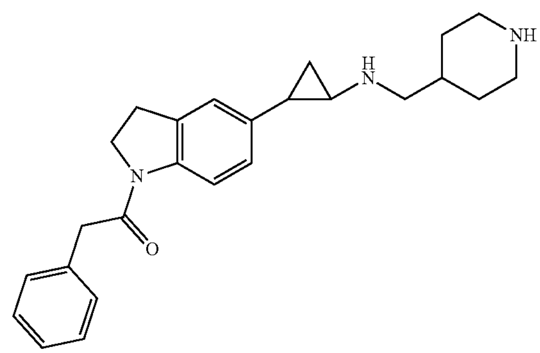 [SMILES: O=C(Cc1ccccc1)N1CCc2cc(C3CC3NCC3CCNCC3)ccc21] |
| A50 | Trans-benzyl-5-(2-(piperidin-4-ylmethylamino)cyclopropyl)indoline-1-carboxylate | 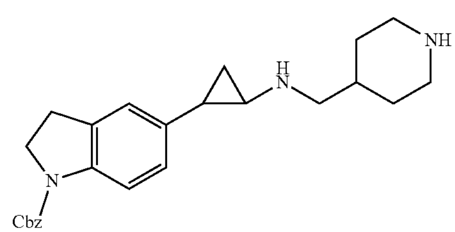 [SMILES: O=C(OCc1ccccc1)N1CCc2cc(C3CC3NCC3CCNCC3)ccc21] |
| A51 | Trans-1-(5-(2-(piperidin-4-ylmethylamino)cyclopropyl)indolin-1-yl)ethanone | 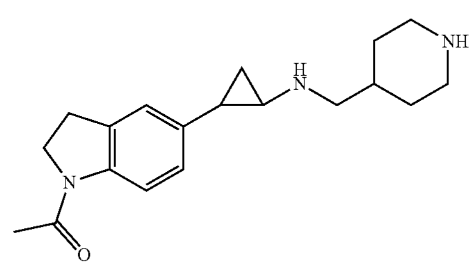 [SMILES: CC(=O)N1CCc2cc(C3CC3NCC3CCNCC3)ccc21] |
| A52 | Trans-2,2,2-trifluoro-1-(5-(2-(piperidin-4-ylmethylamino)cyclopropyl)indolin-1-yl)ethanone | 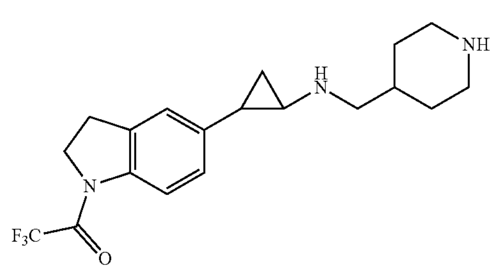 [SMILES: O=C(N1CCc2cc(C3CC3NCC3CCNCC3)ccc21)C(F)(F)F] |

-continued

| No. | Name | Structure |
|---|---|---|
| A53 | Trans-1-(5-(2-(piperidin-4-ylmethylamino)cyclopropyl)indolin-1-yl)propan-1-one | 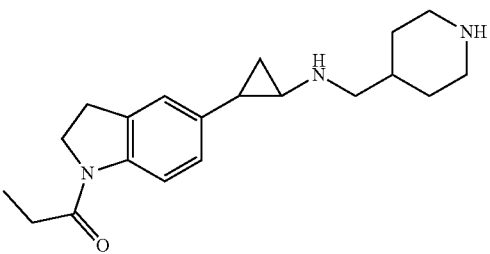 [SMILES: CCC(=O)N1CCc2cc(C3CC3NCC3CCNCC3)ccc21] |
| A54 | Trans-1-(5-(2-(piperidin-4-ylmethylamino)cyclopropyl)indolin-1-yl)butan-1-one | 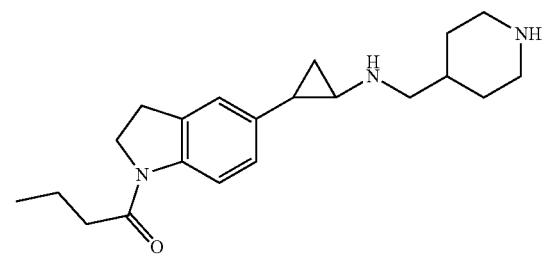 [SMILES: CCCC(=O)N1CCc2cc(C3CC3NCC3CCNCC3)ccc21] |
| A55 | Trans-1-(5-(2-(piperidin-4-ylmethylamino)cyclopropyl)indolin-1-yl)pentan-1-one | 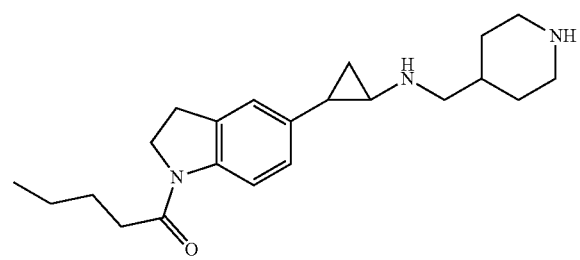 [SMILES: CCCCC(=O)N1CCc2cc(C3CC3NCC3CCNCC3)ccc21] |
| A56 | Trans-3-methoxy-1-(5-(2-(piperidin-4-ylmethylamino)cyclopropyl)indolin-1-yl)propan-1-one | 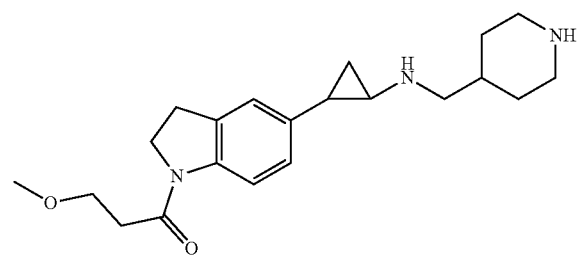 [SMILES: COCCC(=O)N1CCc2cc(C3CC3NCC3CCNCC3)ccc21] |
| A57 | Trans-2-methyl-1-(5-(2-(piperidin-4-ylmethylamino)cyclopropyl)indolin-1-yl)propan-1-one | 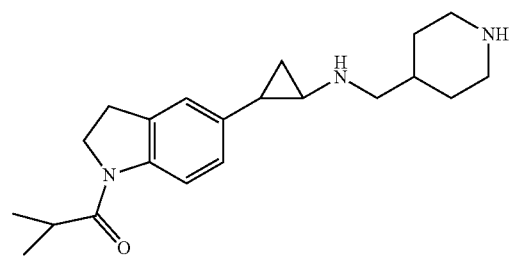 [SMILES: CC(C)C(=O)N1CCc2cc(C3CC3NCC3CCNCC3)ccc21] |
| A58 | Trans-2,2-dimethyl-1-(5-(2-(piperidin-4-ylmethylamino)cyclopropyl)indolin-1-yl)propan-1-one | 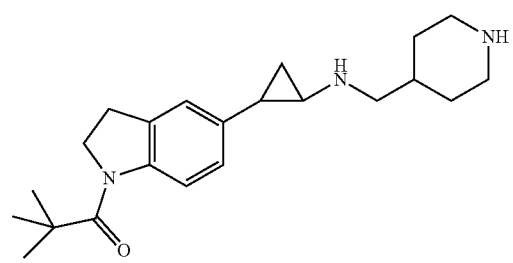 |

-continued

| No. | Name | Structure |
|---|---|---|
| A59 | Trans-cyclohexyl (5-(2-(piperidin-4-ylmethylamino)cyclopropyl)indolin-1-yl)methanone | 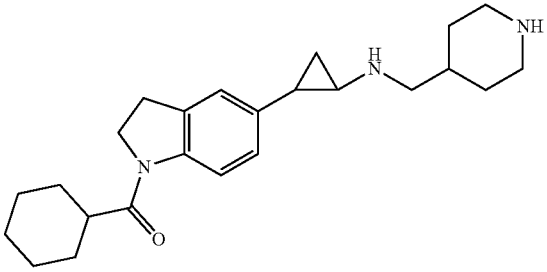 [SMILES: O=C(C1CCCCC1)N1CCc2cc(C3CC3NCC3CCNCC3)ccc21] |
| A60 | Trans-cycloheptyl (5-(2-(piperidin-4-ylmethylamino)cyclopropyl)indolin-1-yl)methanone | 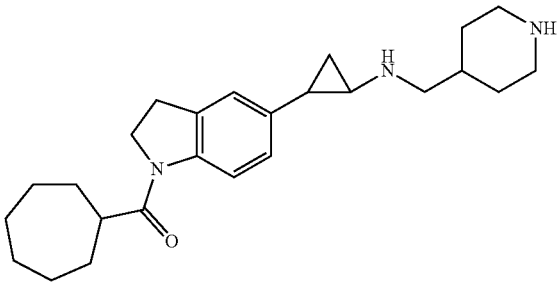 [SMILES: O=C(C1CCCCCC1)N1CCc2cc(C3CC3NCC3CCNCC3)ccc21] |
| A61 | Trans-cyclopentyl (5-(2-(piperidin-4-ylmethylamino)cyclopropyl)indolin-1-yl)methanone | 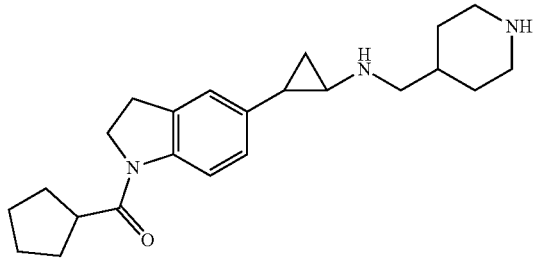 [SMILES: O=C(C1CCCC1)N1CCc2cc(C3CC3NCC3CCNCC3)ccc21] |
| A62 | Trans-cyclobutyl (5-(2-(piperidin-4-ylmethylamino)cyclopropyl)indolin-1-yl)methanone | 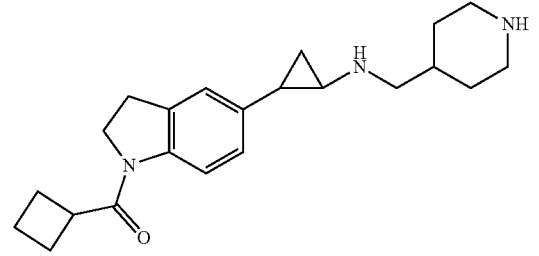 [SMILES: O=C(C1CCC1)N1CCc2cc(C3CC3NCC3CCNCC3)ccc21] |
| A63 | Trans-cyclopropyl (5-(2-(piperidin-4-ylmethylamino)cyclopropyl)indolin-1-yl)methanone | 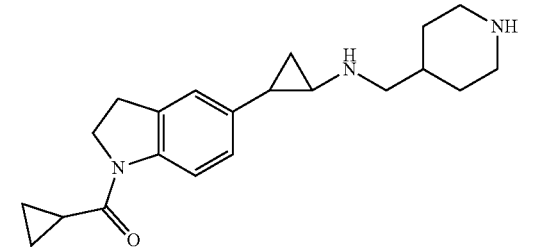 [SMILES: O=C(C1CC1)N1CCc2cc(C3CC3NCC3CCNCC3)ccc21] |

-continued

| No. | Name | Structure |
|---|---|---|
| A64 | trans-N-(2-(1-(phenylsulfonyl)-1,2,3,4-tetrahydroquinolin-6-yl)cyclopropyl)aniline | 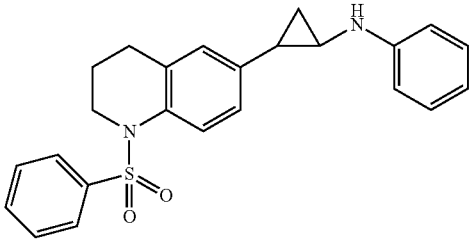 [SMILES: O=S(=O)(c1ccccc1)N1CCCc2cc(C3CC3Nc3ccccc3)ccc21] |
| A65 | trans-N-benzyl-2-(1-(phenylsulfonyl)-1,2,3,4-tetrahydroquinolin-6-yl)cyclopropylamine | 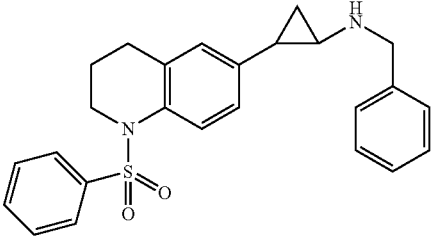 [SMILES: O=S(=O)(c1ccccc1)N1CCCc2cc(C3CC3NCc3ccccc3)ccc21] |
| A66 | trans-N-(2-(1-(phenylsulfonyl)-1,2,3,4-tetrahydroquinolin-6-yl)cyclopropyl)piperidin-4-amine | 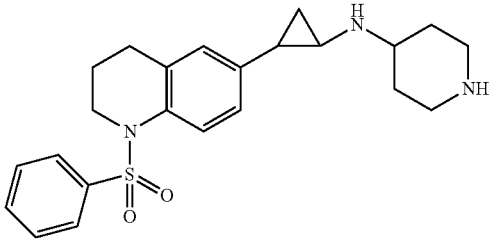 [SMILES: O=S(=O)(c1ccccc1)N1CCCc2cc(C3CC3NC3CCNCC3)ccc21] |
| A67 | Trans-2-(1-(phenylsulfonyl)-1,2,3,4-tetrahydroquinolin-6-yl)-N-(piperidin-4-ylmethyl)cyclopropylamine | 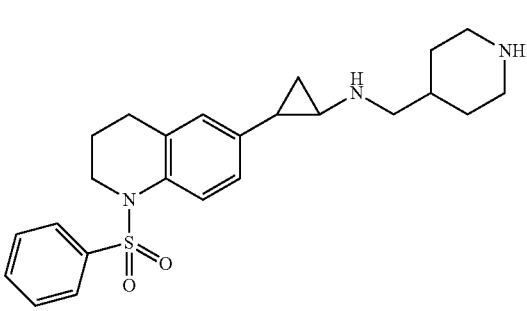 [SMILES: O=S(=O)(c1ccccc1)N1CCCc2cc(C3CC3NCC3CCNCC3)ccc21] |
| A68 | trans-N-(piperidin-4-ylmethyl)-2-(1-(propylsulfonyl)-1,2,3,4-tetrahydroquinolin-6-yl)cyclopropylamine | 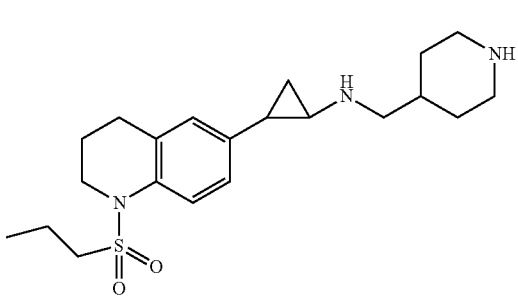 [SMILES: CCCS(=O)(=O)N1CCCc2cc(C3CC3NCC3CCNCC3)ccc21] |

| No. | Name | Structure |
|---|---|---|
| A69 | trans-2-(1-(cyclohexylsulfonyl)-1,2,3,4-tetrahydroquinolin-6-yl)-N-(piperidin-4-ylmethyl)cyclopropylamine | 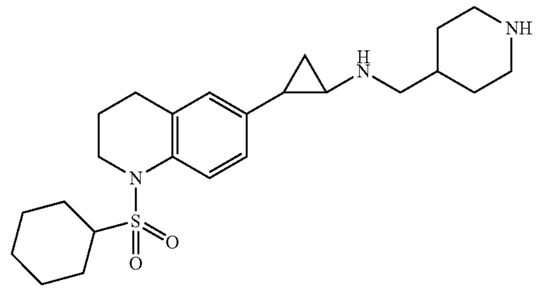 [SMILES: O=S(=O)(C1CCCCC1)N1CCCc2cc(C3CC3NCC3CCNCC3)ccc21] |
| A70 | trans-phenyl(6-(2-(piperidin-4-ylmethylamino)cyclopropyl)-3,4-dihydroquinolin-1(2H)-yl)methanone | 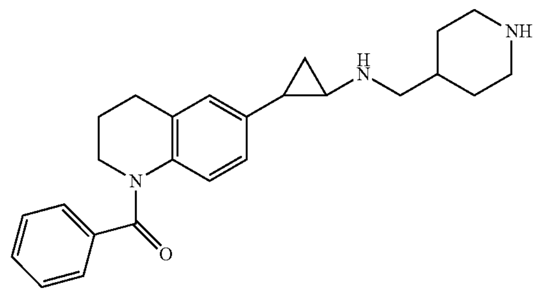 [SMILES: O=C(c1ccccc1)N1CCCc2cc(C3CC3NCC3CCNCC3)ccc21] |
| A71 | trans-1-(6-(2-(piperidin-4-ylmethylamino)cyclopropyl)-3,4-dihydroquinolin-1(2H)-yl)butan-1-one | 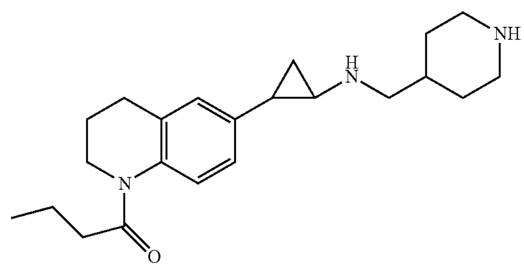 [SMILES: CCCC(=O)N1CCCc2cc(C3CC3NCC3CCNCC3)ccc21] |
| A72 | trans-cyclohexyl (6-(2-(piperidin-4-ylmethylamino)cyclopropyl)-3,4-dihydroquinolin-1(2H)-yl)methanone | 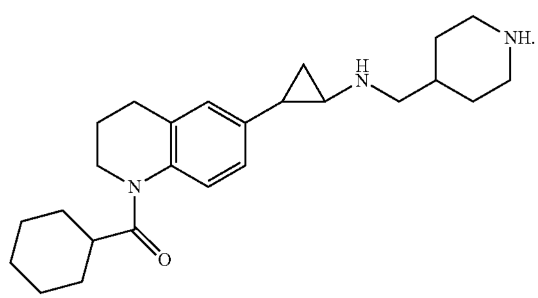 [SMILES: O=C(C1CCCCC1)N1CCCc2cc(C3CC3NCC3CCNCC3)ccc21] |

6. A lysine-specific demethylase 1 (LSD1) inhibitor, wherein the inhibitor comprises a compound according to claim 1, or a enantiomer, diastereomer, racemate or mixture thereof, or a pharmaceutically acceptable salt, crystalline hydrate, or solvate thereof.

7. A preparation method for the compound of formula (I) of claim 1, wherein the method comprises the following steps:

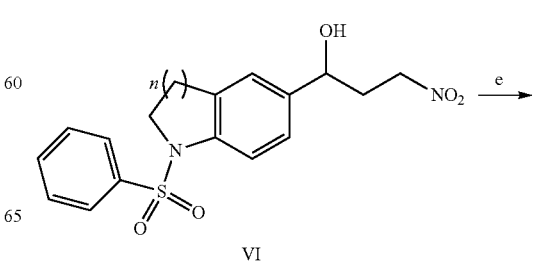

VI

-continued

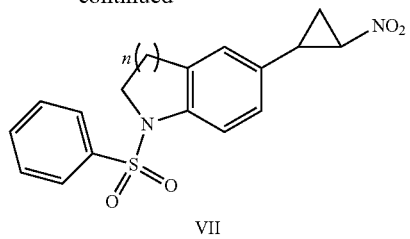

VII (e) in an inert solvent, using alcohol intermediate (VI) to carry out Mitsunobu reaction with nucleophilic reagent to give the compound of formula (VII); and
preparing compound of formula (I) with a compound of formula (VII);
wherein each group is defined as in claim 1.

8. A preparation method for the compound of formula (I) of claim 1, wherein the method comprises the following steps:

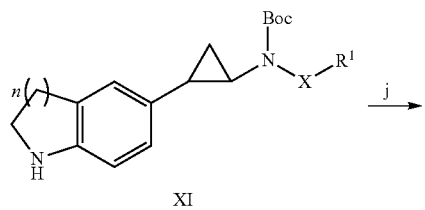

XI

-continued

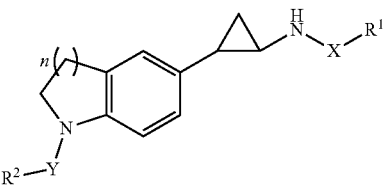

(j) in an inert solvent, reacting formula (XI) compound with acid chloride, and removing the protecting group to give the target product (I);
wherein each group is defined as in claim 1.

9. A pharmaceutical composition comprising (A) a therapeutically effective amount of a compound according to claim 1, or a enantiomer, diastereomer, racemate, or mixture thereof, or a pharmaceutically acceptable salt, crystalline hydrate or solvate thereof; and (B) a pharmaceutically acceptable carrier.

10. A method for treating a malignant tumor disease associated with lysine-specific demethylase 1 (LSD1) comprising administering a therapeutically effective amount of a compound according to claim 1, or a enantiomer, diastereomer, racemate, or mixture thereof, or a pharmaceutically acceptable salt, crystalline hydrate or solvate thereof.

\* \* \* \* \*